US011399761B2

(12) United States Patent
Intrator

(10) Patent No.: US 11,399,761 B2
(45) Date of Patent: *Aug. 2, 2022

(54) SYSTEMS AND METHODS FOR ANALYZING BRAIN ACTIVITY AND APPLICATIONS THEREOF

(71) Applicant: NeuroSteer, Ltd., New York, NY (US)

(72) Inventor: Nathan Intrator, New York, NY (US)

(73) Assignee: NEUROSTEER INC., New York, NY (US)

( * ) Notice: Subject to any disclaimer, the term of this patent is extended or adjusted under 35 U.S.C. 154(b) by 389 days.

This patent is subject to a terminal disclaimer.

(21) Appl. No.: 16/673,864

(22) Filed: Nov. 4, 2019

(65) Prior Publication Data

US 2020/0138323 A1 May 7, 2020

Related U.S. Application Data

(63) Continuation of application No. 15/616,503, filed on Jun. 7, 2017, now Pat. No. 10,463,271.

(Continued)

(51) Int. Cl.
*A61B 5/00* (2006.01)
*A61B 5/372* (2021.01)
(Continued)

(52) U.S. Cl.
CPC .............. *A61B 5/291* (2021.01); *A61B 5/316* (2021.01); *A61B 5/369* (2021.01); *A61B 5/375* (2021.01);
(Continued)

(58) Field of Classification Search
CPC combination set(s) only.
See application file for complete search history.

(56) References Cited

U.S. PATENT DOCUMENTS

2002/0107454 A1* 8/2002 Collura ................. G16H 40/67
600/544
2004/0028264 A1* 2/2004 Kalita ................... G06T 11/008
382/131

(Continued)

FOREIGN PATENT DOCUMENTS

WO 2008057365 A2 5/2008
WO 2016132228 A2 8/2016

OTHER PUBLICATIONS

Supplementary European Search Report to corresponding EP Application No. 17809796 dated Jan. 21, 2020 (6 pages).

*Primary Examiner* — Etsub D Berhanu
(74) *Attorney, Agent, or Firm* — Greenberg Traurig, LLP

(57) ABSTRACT

In some embodiments, the present invention provides an exemplary inventive system that includes: an apparatus to record: individual's brain electrical activity, a physiological parameter of the individual, and iii) an environmental parameter; a computer processor configured to perform: obtaining a recording of the electrical signal data; projecting the obtained recording of electrical signal data onto a pre-determined ordering of a denoised optimal set wavelet packet atoms to obtain a set of projections; normalizing the particular set of projections of the individual using a pre-determined set of normalization factors to form a set of normalized projections; determining a personalized mental state of the individual by assigning a brain state; determining a relationship between: the physiological parameter, the environmental parameter, and the personalized mental state; generating an output, including: a visual indication, representative of the personalized mental state, and) a feedback output configured to affect the personalized mental state of the individual.

27 Claims, 22 Drawing Sheets
(14 of 22 Drawing Sheet(s) Filed in Color)

Related U.S. Application Data

(60) Provisional application No. 62/375,004, filed on Aug. 15, 2016, provisional application No. 62/346,626, filed on Jun. 7, 2016.

(51) Int. Cl.
*A61B 5/377* (2021.01)
*A61B 5/291* (2021.01)
*A61B 5/316* (2021.01)
*A61B 5/369* (2021.01)
*A61B 5/375* (2021.01)
*A61B 5/0205* (2006.01)
*A61B 5/055* (2006.01)

(52) U.S. Cl.
CPC ............ *A61B 5/6803* (2013.01); *A61B 5/726* (2013.01); *A61B 5/7264* (2013.01); *A61B 5/0205* (2013.01); *A61B 5/055* (2013.01); *A61B 5/4064* (2013.01); *A61B 5/7246* (2013.01)

(56) References Cited

U.S. PATENT DOCUMENTS

| | | | |
|---|---|---|---|
| 2007/0287930 A1* | 12/2007 | Sutton | A61M 21/00 600/544 |
| 2008/0161712 A1* | 7/2008 | Leyde | A61B 5/0006 600/544 |
| 2010/0114813 A1* | 5/2010 | Zalay | A61B 5/374 706/58 |
| 2011/0092837 A1 | 4/2011 | Lee et al. | |
| 2011/0288424 A1* | 11/2011 | Kanai | A61B 5/369 600/500 |
| 2011/0301433 A1 | 12/2011 | Sadowsky et al. | |
| 2011/0301487 A1* | 12/2011 | Abeyratne | G16H 50/50 600/544 |
| 2012/0150010 A1 | 6/2012 | Hayes-Gill et al. | |
| 2013/0310701 A1 | 11/2013 | Kobayashi et al. | |
| 2015/0265201 A1* | 9/2015 | Arbas | A61B 5/082 600/301 |
| 2015/0338917 A1* | 11/2015 | Steiner | A61B 5/316 345/156 |
| 2016/0077547 A1 | 3/2016 | Aimone et al. | |
| 2016/0270718 A1* | 9/2016 | Heneghan | A61B 5/4815 |
| 2018/0296156 A1 | 10/2018 | Penders et al. | |

\* cited by examiner

SYSTEMS AND METHODS FOR ANALYZING BRAIN ACTIVITY AND APPLICATIONS THEREOF

RELATED APPLICATIONS

This application is a continuation of U.S. patent application Ser. No. 15/616,503, filed Jun. 7, 2017, entitled "SYSTEMS AND METHODS FOR ANALYZING BRAIN ACTIVITY AND APPLICATIONS THEREOF," which claims the priority of U.S. Provisional Application No. 62/346,626, filed Jun. 7, 2016, entitled "SYSTEMS AND METHODS FOR BRAIN ACTIVITY INTERPRETATION," and U.S. Provisional Application No. 62/375,004, filed Aug. 15, 2016, entitled "SYSTEMS AND METHODS FOR BRAIN ACTIVITY MONITORING," the content of each of which is incorporated herein by reference in its entirety for all purposes.

FIELD OF THE INVENTION

The present invention relates to a method and system for monitoring the brain state, the health and wellness of individuals. In particular, the present invention relates to a system for monitoring an individual's brain activity, and other physiological parameters, and environmental parameters, correlating the monitored brain activity with the physiological and environmental parameters, and from the correlation, detecting changes in the individual's cognitive ability and/or brain state.

BACKGROUND OF THE INVENTION

Electroencephalography (EEG) is one method to monitor electrical activity of the brain. It is typically noninvasive, with the electrodes placed along the scalp, however, invasive electrodes may be used in specific applications. EEG measures voltage fluctuations resulting from ionic current within the neurons of the brain. However, the sensitivity of the EEG electrodes limits detection to small regions of the brain, close to each electrode, thus limiting the spatial resolution of EEG.

Functional magnetic resonance imaging (fMRI) is another method to monitor activity of the brain. However, a magnetic resonance imager is a large and expensive clinical device which can neither be used outside of the clinic, nor in a continuous manner.

SUMMARY OF THE INVENTION

In some embodiments, the present invention provides an exemplary inventive system that includes at least the following components: an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; a specifically programmed computer system; where the specifically programmed computer system includes: i) a non-transient memory, electronically storing particular computer executable program code; and ii) at least one computer processor which, when executing the particular program code, becomes a specifically programmed computer processor configured to perform at least the following operations: continuously obtaining a recording of electrical signal data representative of the individual's brain electrical activity; continuously projecting, in real time, the obtained recording of electrical signal data onto a pre-determined ordering of a denoised optimal set wavelet packet atoms, to obtain a particular set of projections of the individual; continuously normalizing, in real time, the particular set of projections of the individual using a pre-determined set of normalization factors to form a set of normalized projections of the individual; continuously determining, in real time, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition; continuously determining a relationship between: i) the at least one physiological parameter, ii) the at least one environmental parameter, and iii) the at least one personalized mental state; continuously generating, in real time, an output, including: 1) a visual indication, where the visual indication is representative of the at least one personalized mental state, and 2) a feedback output which is configured to affect, based on the relationship, the at least one personalized mental state of the individual.

In some embodiments, the feedback output is selected from the group consisting of: an audible signal, a visual signal, a physically-sensed signal, and any combination thereof.

In some embodiments, the physically-sensed signal is a vibration that is physically sensed by the individual.

In some embodiments, the generating of the feedback output includes: determining a change beyond a pre-determined threshold in at least one of: i) the at least one physiological parameter, ii) the at least one environmental parameter, and iii) the at least one personalized mental state.

In some embodiments, the specifically programmed computer processor is further configured to determine the pre-determined ordering of the denoised optimal set wavelet packet atoms based on: obtaining from a plurality of individuals at least 100 recordings of electrical signal data representative of brain activity; obtaining an optimal set of wavelet packet atoms from the recorded electrical signal data from the recordings from the plurality of individuals, by: 1) selecting a mother wavelet selected from the group consisting of: Haar, Coiflet Daubehies, and Meyer wavelet families; 2) determining, by the specifically programmed processor, an optimal set of wavelet packet atoms, by: a) causing the at least one plurality of electrical signal data to be deconstructed into a plurality of wavelet packet atoms, using the selected mother wavelet; b) storing the plurality of wavelet packet atoms in at least one first computer data object; c) determining the optimal set of wavelet packet atoms using the pre-determined mother wavelet, and storing the optimal set of wavelet packet atoms in at least one second computer data object, where the determining is via utilizing a Coifman-Wickerhauser Best Basis algorithm; i) denoising the obtained optimal set of wavelet packet atoms from the recordings from the plurality of individuals; ii) reordering, the denoised optimal set of wavelet packet atoms from the recorded electrical signal data from the recordings from the plurality of individuals, to obtain a pre-determined ordering of the denoised optimal set of wavelet packet atoms from the recordings from the plurality of the individuals, by determining a minimum path, by: 1) projecting the at least one plurality of electrical signal data on to the denoised optimal set of wavelet packet atoms, to obtain a set of projections, where a projection is a result of a convolution of an electrical signal in each time window of the signal and a wavelet packet atom; 2) determining a collection of wire lengths for every data point within the set of projections, where each wire length is determined by a correlation of every two projections; 3) storing the collection of wire lengths for the set of projections in at least one third computer data object; 4) iteratively, determining, by the specifically programmed processor, a plurality of (i) orders of projections, and (ii) respective wire lengths, by i) determining the wire length for every data point in the projection by determining either the mean or sum of absolute distance of the statistical measure of the projections of different channels from their adjacent channels; and ii) storing the wire length data in at least one fourth computer data object; 5) determining, from the plurality of respective wire lengths, a particular order of projections that minimizes either the mean or sum of the wire lengths across the projections, across each 4 second window, and across all individuals within the plurality of individuals so as to identify the pre-determined ordered denoised optimal set of wavelet packet atoms; and creating the set of pre-determined normalization factors, and storing the pre-determined normalization factors in at least one fifth computer data object.

In some embodiments, the visual indication includes a visual map, generated by: calculating a standard deviation of a time window of each normalized projection of the particular set of normalized projections of the particular individual, and assigning a color to each normalized projection of the particular set of normalized projections of the particular individual, based on the standard deviation of the time window of the respective projection.

In some embodiments, the correlation of every two projections is selected from the group consisting of: the mean of the sum of the absolute differences of the wavelet packet atoms, and a mean of the sum of (1−correlation) of the wavelet packet atoms.

In some embodiments, the apparatus includes two electrodes configured to record the electrical signal data representative of the individual's brain activity.

In some embodiments, when the individual is a child between years of 0 and 12; the at least one personalized mental state is representative of a response of the child to at least one first musical stimulus; and the feedback output is at least one second musical stimulus.

In some embodiments, when the individual is a minimally conscious subject; the at least one personalized mental state is representative of a response of the minimally conscious subject to at least one stimulus; and the feedback output is at least one second stimulus configured to affect the minimally conscious subject.

In some embodiments, the least one environmental parameter is selected from the group consisting of: temperature, humidity, pressure, allergen level, and any combination thereof.

In some embodiments, the at least one machine learning algorithm is one of: logistic regression modeling algorithm, support vector machine modeling algorithm, and a deep learning modeling algorithm.

In some embodiments, the specifically programmed computer processor is further configured to perform at least the following operations: a) determining a first personalized mental state of the individual; b) generating a first visual indication, where the first visual indication is representative of the first personalized mental state; c) generating a first feedback output which is configured to affect, based on a first relationship, the first personalized mental state of the individual; where the first relationship is determined based on: i) at least one first physiological parameter, ii) at least one first environmental parameter, and iii) a first personalized mental state; d) determining, after subjecting the individual to the first feedback output, a second personalized mental state of the individual; e) generating a second visual indication, where the second visual indication is representative of the second personalized mental state; f) comparing the first visual indication and the second visual indication; g) generating a second feedback output which is configured to affect, based on a second relationship and a result of the comparing step, the second personalized mental state of the individual; where the second relationship is determined based on: i) at least one second physiological parameter, ii) at least one second environmental parameter, and iii) a second personalized mental state; repeating the steps a-g until at least one of: 1) a desired personalized mental state is obtained, 2) a first coherent response to the first feedback output is obtained, 3) a second coherent response to the second feedback output is obtained; and 4) any combination thereof.

In some embodiments, the first feedback output is at least one first reward.

In some embodiments, the second feedback output is at least one second reward.

In some embodiments, the present invention provides an exemplary inventive method that includes at least the following steps of: continuously obtaining, by a specifically programmed computer processor, a recording of electrical signal data representative of an individual's brain electrical activity; where the recording the electrical signal data representative of individual's brain electrical activity is received from an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; continuously projecting, in real time, by the specifically programmed computer processor, the obtained recording of electrical signal data onto a pre-determined ordering of a denoised optimal set wavelet packet atoms, to obtain a particular set of projections of the individual; continuously normalizing, in real time, by the specifically programmed computer processor, the particular set of projections of the individual using a pre-determined set of normalization factors to form a set of normalized projections of the individual; continuously determining, in real time, by the specifically programmed computer processor, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition;

continuously determining, by the specifically programmed computer processor, a relationship between: i) the at least one physiological parameter, ii) the at least one environmental parameter, and iii) the at least one personalized mental state; continuously generating, in real time, by the specifically programmed computer processor, an output, including: 1) a visual indication, where the visual indication is representative of the at least one personalized mental state, and 2) a feedback output which is configured to affect, based on the relationship, the at least one personalized mental state of the individual.

BRIEF DESCRIPTION OF THE FIGURES

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION OF THE INVENTION

Figure 1:
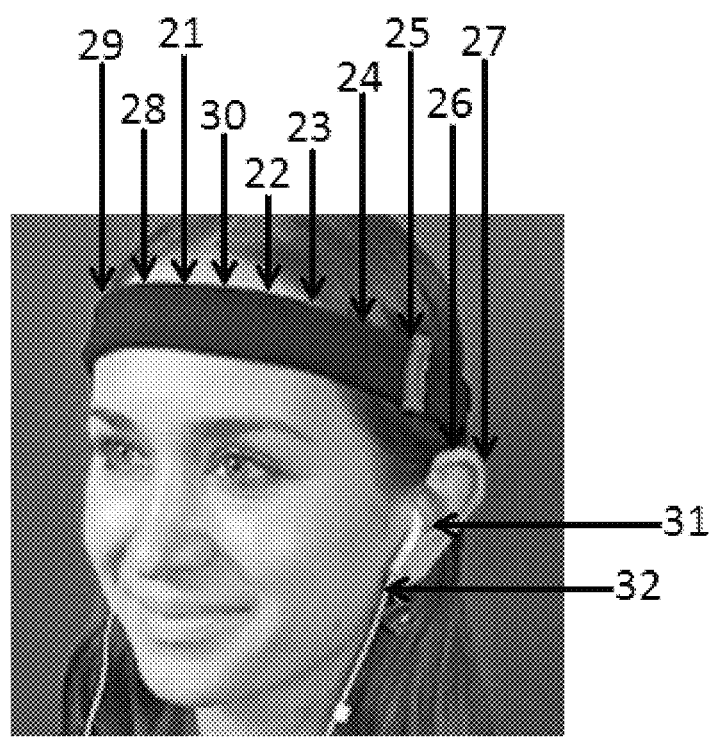
FIG. 1 shows an apparatus according to some embodiments of the present invention.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. In some embodiments, the terms "instantaneous," "instantaneously," "instantly," and "in real time" refer to a condition where a time difference between a first time when a search request is transmitted and a second time when a response to the request is received is no more than 1 second. In some embodiments, the time difference between the request and the response is between less than 1 second and several seconds.

As used herein, the term "dynamic(ly)" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

Apparatus for Monitoring Brain Activity, Physiological Parameters, and Environmental Parameters In some embodiments, the present invention provides a system and method for monitoring detailed brain activity in an individual concurrently with monitoring the sensory environment so as to create a rich input/output relationship between the sensory environment and the related brain activity so as to detect states relating to normal and stimulated brain activity and brain malfunction.

In some embodiments, the apparatus is configured to be worn continuously. In some embodiments, the apparatus is configured to be worn while the individual is asleep. In some embodiments, the apparatus is configured to be worn while the individual is awake.

In one embodiment, the present invention provides a system comprising:
 a. an apparatus configured to be worn on an individual's head, and record:
  i. the individual's brain electrical activity;
  ii. at least one physiological parameter of the individual, selected from the group consisting of: heart rate, blood oxygen and/or carbon dioxide levels, body temperature, respiration rate, skin temperature, skin conductivity, and movement; and iii. at least one environmental parameter, selected but not limited to the group consisting of: temperature, humidity, pressure, and allergen level;
 b. a specifically programmed computer system, configured to (i) receive and process data corresponding to the individual's recorded brain activity, at least one recorded physiological parameter, and at least one recorded environmental parameter, and output, based on the processing, a visual indication of at least one personalized mental state of the particular individual, at least one personalized neurological condition of the particular individual, or both, wherein the visual indication of at least one personalized mental state of the particular individual, at least one personalized neurological condition of the particular individual, or both, is used to identify an underlying mental state, an underlying neurological condition, or a combination of an underlying mental state and an underlying neurological condition, wherein the system is configured to issue an alert if at least one of the underlying mental state, the underlying neurological condition, the combination of the underlying mental state and the underlying neurological condition, the at least one physiological condition, or the at least one environmental parameters changes beyond a pre-determined threshold.

In one embodiment, present invention provides a specifically programmed computer system including:
 a. at least one specialized computer machine including:
  i. a non-transient memory, electronically storing particular computer executable program code; and
  ii. at least one computer processor which, when executing the particular program code, becomes a specifically programmed computer processor configured to perform at least the following operations:
   1. obtaining, in real-time, by a specifically programmed processor, electrical signal data representative of brain activity of a particular individual;
   2. processing, in real-time the electrical signal data representative of brain activity of a particular individual based upon an individual pre-determined predictor associated with a particular brain state, selected from a library of predictors containing a plurality of pre-determined predictors, wherein each individual pre-determined predictor is associated with a unique brain state,
    wherein the pre-determined predictor associated with a particular brain state comprises:
     i. a pre-determined mother wavelet,
     ii. a pre-determined representative set of wavelet packet atoms,
     iii. a pre-determined ordering of wavelet packet atoms, created from the pre-determined mother wavelet, and
     iv. a pre-determined set of normalization factors,
    wherein the processing comprises:
     i. causing, by the specifically programmed processor, the electrical signal data to be deconstructed into a plurality of pre-determined deconstructed wavelet packet atoms, utilizing the pre-determined representative set of wavelet packet atoms,
      wherein time windows of the electrical signal data are projected onto the pre-determined representative set of wavelet packet atoms
      wherein the projection is via convolution or inner product, and
      wherein each pre-determined representative wavelet packet atom corresponds to a particular pre-determined brain activity feature from a library of a plurality of pre-determined brain activity features;
     ii. storing the plurality of pre-determined deconstructed wavelet packet atoms in at least one computer data object;
     iii. causing, by the specifically programmed processor, the stored plurality of pre-determined deconstructed wavelet packet atoms to be re-ordered within the computer data object, based on utilizing a pre-determined order;
     iv. obtaining a statistical measure of the activity of each of the re-ordered plurality of pre-determined deconstructed wavelet packet atoms; and
     v. normalizing the re-ordered plurality of pre-determined wavelet packet atoms, based on utilizing a pre-determined normalization factor; and
   3. outputting, a visual indication of at least one personalized mental state of the particular individual, at least one personalized neurological condition of the particular individual, or both, based on the processing,
    wherein an individual pre-determined predictor associated with a particular brain state within the plurality of pre-determined predictors is generated by the steps consisting of:
     i. obtaining the pre-determined representative set of wavelet packet atoms by:
      1. obtaining from a plurality of individuals, by the specifically programmed processor, at least one plurality of electrical signal data representative of a brain activity of a particular brain state;
      2. selecting a mother wavelet from a plurality of mother wavelets, wherein mother wavelet is selected from a wavelet family selected from the group consisting of: Haar, Coiflet Daubehies, and Mayer wavelet families;

3. causing, by the specifically programmed processor, the at least one plurality electrical signal data to be deconstructed into a plurality of wavelet packet atoms, using the selected mother wavelet;

4. storing the plurality of wavelet packet atoms in at least one computer data object;

5. determining, an optimal set of wavelet packet atoms using the pre-determined mother wavelet, and storing the optimal set of wavelet packet atoms in at least one computer data object, wherein the determining is via utilizing a Best Basis algorithm; and 6. applying, by the specifically programmed processor, wavelet denoising to the number of wavelet packet atoms in the optimal set;

ii. obtaining the pre-determined ordering of wavelet packet atoms by:

1. projecting, by the specifically programmed processor, the at least one plurality of electrical signal data representative of a brain activity for each 4 second window of the data onto the pre-determined representative set of wavelet packet atoms;

2. storing the projections in at least one computer data object;

3. determining, by the specifically programmed processor, the wire length for every data point in the projection by determining the mean absolute distance of the statistical measure of the projections of different channels from their adjacent channels;

4. storing the wire length data in at least one computer data object; and 5. re-ordering the stored projections, by the specifically programmed computer to minimize a statistical value of the wire length value across each time window, and across all individuals within the plurality of individuals, and across the projections; and iii. obtaining the pre-determined set of normalization factors by:

1. determining, by the specifically programmed computer, the mean and standard deviation of the values of the stored projections.

In one embodiment, the present invention provides a computer implemented method including:

a. obtaining, in real-time, by a specifically programmed processor, electrical signal data representative of brain activity of a particular individual;

b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state, wherein the pre-determined predictor associated with a particular brain state includes:
i. a pre-determined mother wavelet,
ii. a pre-determined representative set of wavelet packet atoms, created from the pre-determined mother wavelet,
iii. a pre-determined ordering of wavelet packet atoms, and
iv. a pre-determined set of normalization factors, wherein the processing includes:
i. causing, by the specifically programmed processor, the electrical signal data to be deconstructed into a plurality of pre-determined deconstructed wavelet packet atoms, utilizing the pre-determined representative set of wavelet packet atoms,
wherein time windows of the electrical signal data are projected onto the pre-determined representative set of wavelet packet atoms
wherein the projection is via convolution or inner product, and
wherein each pre-determined representative wavelet packet atom corresponds to a particular pre-determined brain activity feature from a library of a plurality of pre-determined brain activity features;
ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and c. outputting, a visual indication of at least one personalized mental state of the particular individual, at least one personalized neurological condition of the particular individual, or both, based on the processing, wherein the individual pre-determined predictor associated with a particular brain state from within the plurality of pre-determined predictors is generated by the steps including:
i. obtaining the pre-determined representative set of wavelet packet atoms by:
a. obtaining from a plurality of individuals, by the specifically programmed processor, at least one plurality of electrical signal data representative of a brain activity of a particular brain state;
b. selecting a mother wavelet from a plurality of mother wavelets,
wherein the mother wavelet is a member of a wavelet family selected from the group consisting of: Haar, Coiflet Daubehies, and Mayer wavelet families;
c. causing, by the specifically programmed processor, the at least one plurality electrical signal data to be deconstructed into a plurality of wavelet packet atoms, using the selected mother wavelet;
d. storing the plurality of wavelet packet atoms in at least one computer data object;
e. determining, an optimal set of wavelet packet atoms using the pre-determined mother wavelet, and storing the optimal set of wavelet packet atoms in at least one computer data object,
wherein the determining is via utilizing analysis Best Basis algorithm; and
f. applying, by the specifically programmed processor, wavelet denoising to the number of wavelet packet atoms in the optimal set;
ii. obtaining the pre-determined ordering of wavelet packet atoms by:
a. projecting, by the specifically programmed processor, the at least one plurality of electrical signal data representative of a brain activity for each 4 second window of the data onto the pre-determined representative set of wavelet packet atoms;
b. storing the projections in at least one computer data object;
c. determining, by the specifically programmed processor, the wire length for every data point in the projection by determining the mean absolute distance of the statistical measure of the projections of different channels from their adjacent channels;
d. storing the wire length data in at least one computer data object; and
e. re-ordering the stored projections, by the specifically programmed computer to minimize a statistical value of the wire length value across each time window, and across all individuals within the plurality of individuals, and across the projections; and
iii. obtaining the pre-determined set of normalization factors by:
a. determining, by the specifically programmed computer, the mean and standard deviation of the values of the stored projections.

In one embodiment, the computer implemented method further comprises:
a. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
b. determining a relationship between the obtained data and the visual indication of at least one personalized mental state of the particular individual, at least one personalized neurological condition of the particular individual, or both.

In one embodiment, each time window is a four second time window.

In one embodiment, the statistical value for the re-ordering is the mean of the sum of the absolute differences of the wavelet packet atoms or a mean of the sum of (1−correlation) of the wavelet packet atoms.

In one embodiment, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm, which includes, but is not limited to logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In one embodiment, the assignment of at least one specific brain state to the visual indication of at least one personalized mental state of the particular individual identifies an abnormality in at least one neural network in the brain of the particular individual associated with a particular neurological condition.

In one embodiment, the abnormality in at least one neural network in the brain of the particular individual is used to diagnose the particular individual having a neurological condition.

In one embodiment, the neurological condition is selected from the group consisting of, Alzheimer's disease, dementia, stress, fatigue, anxiety, epilepsy, traumatic brain injury, loss of cognitive function, migraine, chronic pain, perceived pain (e.g., such as that associated with phantom limb pain), post-traumatic stress disorder (PTSD), acute pain, coma, a lack of response, or inappropriate response to external stimuli associated with autism, or autism spectrum disorders, obsessive compulsive disorders (e.g., bulimia and anorexia nervosa), a lack of concentration, and sleep disorders.

In one embodiment, the at least one specific brain state is used to determine the emotional state of the particular individual.

In one embodiment, the particular individual is receiving a therapy, and the visual indication of at least one personalized mental state of the particular individual is used to determine the effectiveness of the therapy.

In one embodiment, the particular individual is receiving a therapy, and the visual indication of at least one personalized mental state of the particular individual is used to determine the nature of the therapy to be administered.

In one embodiment, the particular individual is receiving a therapy, and the visual indication of at least one personalized mental state of the particular individual is used to determine the duration of the therapy.

In one embodiment, the particular individual is receiving a therapy, and the visual indication of at least one personalized mental state of the particular individual is used to determine the dosing regimen of the therapy.

In one embodiment, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In one embodiment, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In one embodiment, the particular individual is performing a specific cognitive task.

In one embodiment, the specific cognitive task is selected from the group including short and/or long term memory recall, e-learning, meditation, and concentration.

In one embodiment, the particular individual has a particular brain state at a certain time.

In one embodiment, the present invention provides a method,
wherein the method induces a change in the mental state, neurological condition, or both of a subject from a first mental state, first neurological condition, or both, to a desired mental state, desired neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. determining if the second visual indication of a second mental state, second neurological condition, or both, of the subject is indicative of the desired mental state, second neurological condition, or both, and if not;
d. iteratively,
  i. applying at least one subsequent stimulus to the subject,
    wherein each at least one subsequent stimulus is different from the preceding at least one stimulus;
  ii. obtaining a subsequent visual indication of a mental state, neurological condition, or both, of the subject;
  iii. determining if the subsequent visual indication of the mental state, neurological condition, or both, of the subject is indicative of the desired mental state, desired neurological condition, or both,
    wherein steps i to iii are performed until the desired mental state, desired neurological condition, or both, is obtained.

In one embodiment, the present invention provides a method,
wherein the method induces a change in the mental state, neurological condition, or both, of a subject from a first mental state, first neurological condition, or both, to a desired mental state, desired neurological condition, or both, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and if not;
d. iteratively,
  i. comparing the first visual indication of a first mental state, first neurological condition, or both of the subject to the second visual indication of a second mental state, second neurological condition, or both of the subject;
  ii. based on the comparison, selecting a subsequent stimulus and applying the selected subsequent stimulus to the subject,
    wherein each at least one subsequent selected stimulus is different from the preceding at least one stimulus;
  iii. obtaining a subsequent visual indication of a mental state, neurological condition, or both of the subject;
  iv. determining if the subsequent visual indication of the mental state, neurological condition, or both of the subject is indicative of the desired mental state, desired neurological condition, or both,
    wherein steps i to iv are performed until the desired mental state, desired neurological condition, or both, is obtained.

In some embodiments, BAF representations are further analyzed to identify features that are repeatedly observed in a subject's visual representation of brain activity in response to an at least one stimulus. For example, Let $B(j,t)$ be a matrix of BAF where the rows j go from 1 to 121 in case of 121 BAFs, and the columns t represent time with steps of one second, namely the BAF vectors is being updated every 1 sec. In some embodiments, the rows that are more correlated are ordered geographically closer to one another, so the brain activity values in row j are more correlated to those in row j+1 than to those in row j+2, under some measure of correlation over a large data set that was used to determine the BAFs.

There is also a labeling $L(t)$ which labels what happened during the recording of each time column. Thus, it is possible to build predictors to specific events that occurred during the time the BAF data was collected, and it is possible to cluster the columns of the matrix in a supervised (looking at the labels) or unsupervised way, like in k-means clustering. Furthermore, it is possible to cluster only part of the matrix namely only several of the BAFs. This enables to find those channels that produce a more coherent set of clusters from the data, namely they produce a set of cluster centers where the activity in a specific set of channels often falls into one of the cluster centers, namely the actual activity is not far (by some measure such as Euclidian distance) from the activity represented by the cluster center.

In some embodiments, the clusters are named, to indicate the BAF channels where they came from, and the actual cluster center that was found in those channel: for example, one feature, by way of illustration can be named 1320_15, to indicate that the cluster corresponds to channels 13 to 20 and it is ordinal cluster 15 that was found in that set of BAFs. This actual name can be considered a certain letter in a novel alphabet that can be found in brain activity after the interpretation into BAFs.

Given this alphabet, in some embodiments, one can then look at letters which are highly correlated, namely clusters from different channels which co-occur at high probability. Then such letters can be combined into a single letter. This is done after building a covariance matrix of all letters found, and then based on then combining letters with a correlation above a preset threshold.

In some embodiments, once a minimal alphabet is found (after combining highly correlated letters) one can look at words that are being formed, namely a collection of several letters that occur together. Also, in some embodiments, grammatical rules can be inferred using, for example, Markov modeling, namely inference of letters/words which occur in a sequence at high probability. Bayesian modeling, or graphical modeling may be used in some embodiments for inference of hidden structures of letter/words.

All said inference can now be used together with the labeling to determine a correlation of the inferenced brain response and he events that occurred while the BAFs were recorded. Once such correlation is found, we assume that there was a coherent brain response to the stimulus and can then record the stimuli which produced a coherent brain response.

Based on the coherent response, we can determine the response to the stimuli which we term RtS.

In one specific embodiment, RtS can help indicate the type of stimuli that a person that is in a Minimal Conscious State (MCS) responds to. For example, it can help determine whether the person responds in a consistent way to visual stimuli, auditory stimuli, other sensory stimuli, commands etc.

In some embodiments, RtS can indicate the degree of minimal consciousness the person is in, can help optimize medical intervention that aims to increase response to various stimuli. In the case of a person in MCS, in some embodiments, one can look at the entropy of the said alphabet and produce a single number which determines the total entropy of the alphabet (just based on letters or also based on more sophisticated grammatical rules that are inferred and length of words that are inferred.

In one specific embodiment, the said alphabet can be used to create music. This is to enable a MCS subject to produce some means of communication and to obtain neural feedback on its brain activity. Specifically, different letters can produce different musical notes with different musical instruments or can be used to change tempo and other musical parameters. The result would be a melody that is produced from an MCS or a baby's brain and can provide a means of communication. A MCS subject can learn to operate external devices once a control on the production of these letters is achieved. Using the musical feedback, subjects can train to produce the desired response. A reduced version of this, for example, to subjects who have difficulty hearing, or when in a place with a lot of noise, is a Bluetooth operated ball that can move in the XY direction and can also change its colors. These parameters can be tied to some of the BAF, or channels as described below in the caption of FIG. 19.

In a specific embodiment, the group of channels 34-38 which have been found to be missing in MCS can be used as a neural feedback to encourage MCS subjects to increase the activity of these channels.

In another embodiment, the creation of an alphabet and entropy inference from the alphabet can be done in a totally unlabeled (unsupervised) manner. This can be useful when determining the degree of brain damage, such as, for example, of a baby that was born during an ischemic episode, namely a baby that was born while the mother suffered a transient ischemic attack.

Figure 19:
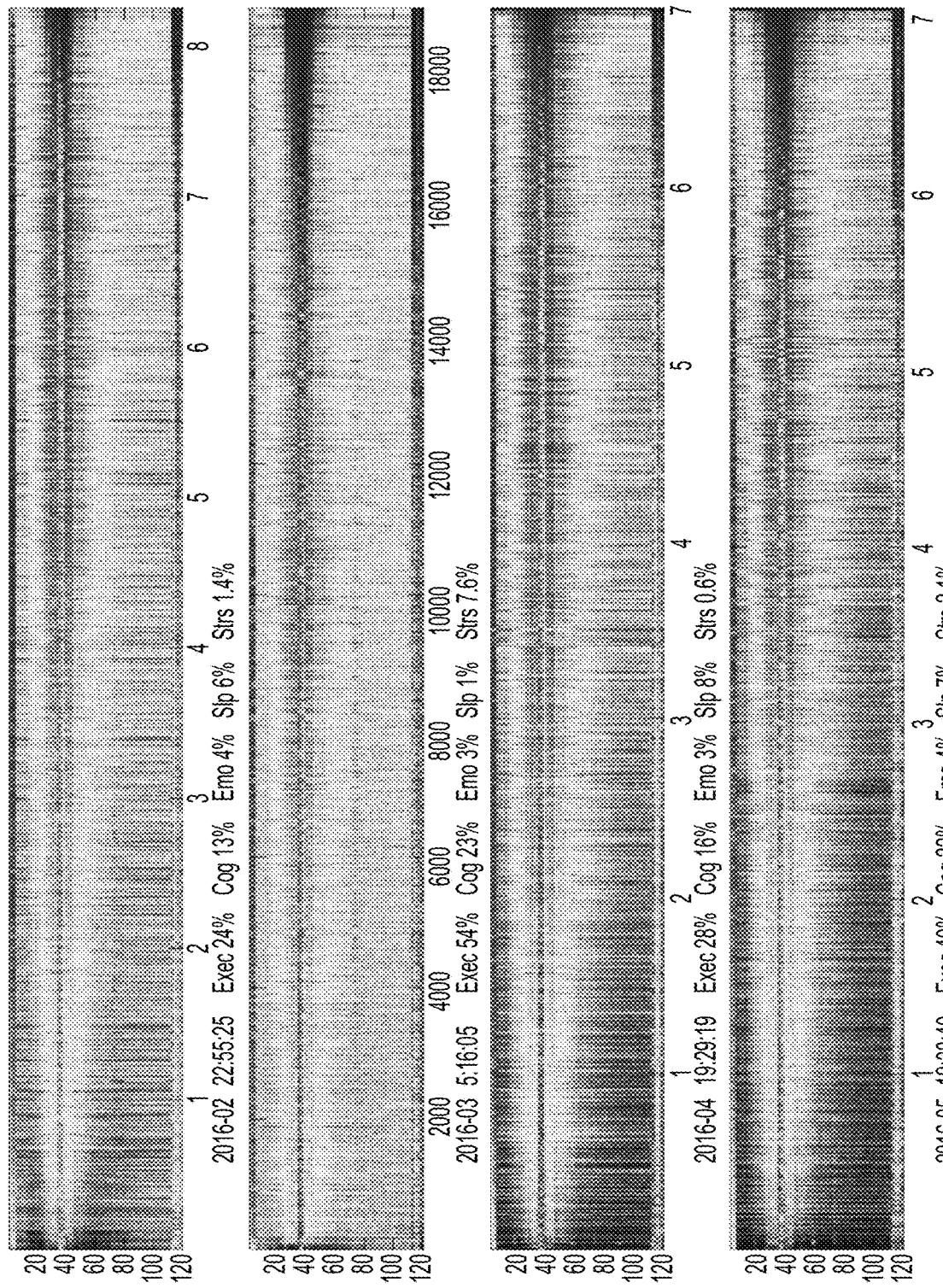
FIG. 19 shows a screenshot of an example of a brain activity features (BAFs) representation of a minimally conscious subject according to some embodiments of the present invention.

In one specific embodiment, a simpler statistical inference can be performed: as several channels were already found to correspond to some general brain activity, for example, there are channels that are associated with emotion brain activity and executive brain activity and are depicted in FIG. 19.

In one embodiment, a temporal structure probabilistic model is applied to the BAF's to determine the correlation between the at least one stimulus applied and the observed brain activity. In some embodiments, a strong correlation indicates a coherent response to the at least one stimulus.

In some embodiments, the apparatus is configured to be worn for up to 24 hours. In some embodiments, the apparatus is configured to be worn for up to 23 hours. In some embodiments, the apparatus is configured to be worn for up to 22 hours. In some embodiments, the apparatus is configured to be worn for up to 21 hours. In some embodiments, the apparatus is configured to be worn for up to 20 hours. In some embodiments, the apparatus is configured to be worn for up to 19 hours. In some embodiments, the apparatus is configured to be worn for up to 18 hours. In some embodiments, the apparatus is configured to be worn for up to 17 hours. In some embodiments, the apparatus is configured to be worn for up to 16 hours. In some embodiments, the apparatus is configured to be worn for up to 15 hours. In some embodiments, the apparatus is configured to be worn for up to 14 hours. In some embodiments, the apparatus is configured to be worn for up to 13 hours. In some embodiments, the apparatus is configured to be worn for up to 12 hours. In some embodiments, the apparatus is configured to be worn for up to 11 hours. In some embodiments, the apparatus is configured to be worn for up to 10 hours. In some embodiments, the apparatus is configured to be worn for up to 9 hours. In some embodiments, the apparatus is configured to be worn for up to 8 hours. In some embodiments, the apparatus is configured to be worn for up to 7 hours. In some embodiments, the apparatus is configured to be worn for up to 6 hours. In some embodiments, the apparatus is configured to be worn for up to 5 hours. In some embodiments, the apparatus is configured to be worn for up to 4 hours. In some embodiments, the apparatus is configured to be worn for up to 3 hours. In some embodiments, the apparatus is configured to be worn for up to 2 hours. In some embodiments, the apparatus is configured to be worn for up to 1 hour.

In some embodiments, the data collected by the apparatus can alert the individual or, alternatively, a caregiver in real time.

In some embodiments, the data collected by the apparatus is stored for offline data analysis.

Without intending to be limited to any particular theory, detecting changes in cognitive abilities, as well as changes in emotional status at home can provide early indications on such changes, which can lead to quick intervention. Without intending to be limited to any particular theory, the earlier the intervention is, the better results can be obtained from the intervention and the lower the cost of the intervention.

In some embodiments, the present invention provides a system comprising:

a. an apparatus configured to be worn on an individual's head, and record:
        i. the individual's brain electrical activity;
        ii. at least one physiological parameter of the individual, selected from the group consisting of: heart rate, blood oxygen and/or carbon dioxide levels, body temperature, respiration rate, skin temperature, skin conductivity, and movement; and
        iii. at least one environmental parameter;
    b. a specifically programmed computer system, configured to (i) receive and process data corresponding to the individual's recorded brain activity, at least one recorded physiological parameter, and at least one recorded environmental parameter, and output, based on the processing, a visual indication of at least one personalized mental state of the particular individual, at least one personalized neurological condition of the particular individual, or both,
        wherein the visual indication of at least one personalized mental state of the particular individual, at least one personalized neurological condition of the particular individual, or both, is used to identify an underlying mental state, an underlying neurological condition, or a combination of an underlying mental state and an underlying neurological condition,
        wherein the system is configured to issue an alert if at least one of the underlying mental state, the underlying neurological condition, the combination of the underlying mental state and the underlying neurological condition, the at least one physiological condition, or the at least one environmental parameters changes beyond as pre-determined threshold.

In some embodiments, the at least one physiological parameter includes, but is not limited to: heart rate, blood oxygen and/or carbon dioxide levels, body temperature, respiration rate, skin temperature, skin conductivity, and movement.

In some embodiments, the at least one physiological parameter is galvanic skin response.

In some embodiments, the apparatus includes a potential pulse oximeter.

In some embodiments, the apparatus includes a 3-D accelerometer.

In some embodiments, the at least one environmental parameter includes, but is not limited to: oxygen concentration, temperature, humidity, carbon monoxide levels, carbon dioxide levels, and the like.

In some embodiments, the apparatus is configured to record alt least one of the following physiological and cognitive parameters from the individual:
1. Sleep level;
2. Sleep stage;
3. Heart rate;
4. Heart rate variability;
5. Cardiac arrhythmia;
6. Cardiac Contractility and cardiac output
7. Blood oxygen and/or carbon dioxide levels;
8. Temporal pulse wave morphology with indications of blood pressure changes (Future);
9. Bit to bit respiration timing and overall respiration rate;
10. Skin temperature and conductivity; or
11. Posture position, movement level, walking and climbing on stairs, sudden fall, lack of movement FIG. 1 shows an apparatus according to some embodiments of the present invention. The following elements indicated on the apparatus are:
21 EEG and/or EOG sensors
22 EEG reference sensor, there are two such sensors above the two eyes
23 Temperature sensor
24 Pulse wave pressure sensor touching the frontal branch of the superficial temporal artery
25 3D Accelerometers
26 Pulse or pulse oximeter (infrared) sensor
27 Battery, electronic circuitry and wireless communication behind the ear
28 Pressure sensor
29 Skin conductance sensor
30 EMG and/or EOG
31 Ear phone
32 Microphone
33 Environmental monitors to provide sensory information in the immediate vicinity of the subject. These include but are not limited to temperature, pressure, humidity which are attached to the sensor suite but are not touching the subject's head.

In some embodiments, the apparatus includes all or some of the above mentioned sensors mounted on the strap or around the ear. In some embodiments, the data collected from the sensors is stored and analyzed on a processor on the sensor which includes cellular communication capabilities. The main processor may be on a nearby cellphone, for example. In some embodiments, the collective sensory information is fused with additional information collected by the cellular processor. Such information includes geographic location, communication with nearby smart devices such as car, home, school or office environment.

In some embodiments, analysis of the data is performed in real-time to obtain:
1) Detection of anomalies, namely activity outside the regular area of activity of the collection of sensors and sensory environment, for a certain part of the sensory input data, e.g. brain malfunction during driving at high temperature;
2) Creation of an organ activity profile from the collection of sensory information. This includes the pulse and hemodynamic activity, as well as vital signs such as temperature and skin conductance. It can be used for statistics collection, or for disease management, such as in sleep or alert time monitoring. Detection of brain malfunctions for a certain sensory environments during other changes such as high blood pressure;
3) Specific patterns which are indicative of specific states, such as concentration, mood, sleep level, certain desire (e.g. to move a limb, or to purchase a product) are calculated from the collective sensory information and are registered. If needed, potential alerts are created, for example, if sleep is detected during driving; and/or
4) Other alerts can be sent to relatives, care givers or other interested parties depending on certain presets of the device. These may include but are not limited to medical alerts of falls, a condition which may pose medical risk, such as epileptic seizure, or sleep at a certain time of day.

Implications of the combined sensory environment and brain activity monitoring relate to mood change detection, attention disorder, or sudden lack of attention, cognitive malfunction and potential medical problems related to hemodynamic parameters such as high or low blood pressure, affecting the said relationship.

In some embodiments, apparatus of the present invention is used to determine the individual's sleep patterns. In some embodiments, changes in an individual's sleep patterns may indicate the onset of a disease or condition. Examples of the disease or condition include, but are not limited to: PTSD, stroke, dementia, Alzheimer's disease, Parkinson's disease, concussion, traumatic brain injury, brain tumor, brain swelling, stress, malnutrition, COPD, sleep apnea, cardiac disease, intoxication, poisoning, hypoxia, and the like.

In some embodiments, the apparatus of the present invention is used in the management of a chronic disease of an individual. Examples of chronic diseases suitable for management using an apparatus according to some embodiments of the present invention include, but are not limited to: epilepsy, depression, Alzheimer's disease, OCS, PTSD, ADD, and the like.

In some embodiments, the apparatus of the present invention is used in the management of an acute disease of an individual. Examples of acute diseases suitable for management using an apparatus according to some embodiments of the present invention include, but are not limited to: concussion, traumatic brain injury, stroke, and the like.

In some embodiments, the apparatus of the present invention is used in the management of post-traumatic stress disorder (PTSD), a condition that afflicts some people following a traumatic experience. It is generally correlated with an inability to recover following a traumatic experience and is typified by ongoing sensations of intense stress and fear, even when considerable time has passed since the traumatic event. PTSD is associated with over-activity of the sympathetic system. PTSD can manifest as a chronic, ongoing condition or a short term, acute condition. Symptoms typically manifest within three months of the traumatic event, but the delay in onset can be years. To be diagnosed with PTSD, an adult must present with all of the following symptoms for at least a month: at least one re-experiencing symptom, at least one avoidance symptom, at least two arousal and reactivity symptoms, and at least two cognition and mood symptoms. Re-experiencing symptoms include flashbacks of the traumatic experience, bad dreams, and frightening thoughts. Avoidance symptoms include avoiding places, events, and/or objects that remind the patient of the traumatic experience and avoiding thoughts or feelings pertaining to the traumatic experience. Arousal and reactivity symptoms include a hyper-active startle reflex, feeling tense or nervous, difficulty sleeping, and a tendency to angry outbursts. Cognition and mood symptoms include difficulty recalling key features of the traumatic event, a negative self-image or overall world image, and distorted feelings like guilt or blame. PTSD is frequently associated with depression, substance abuse, anxiety disorders (e.g., panic disorder), and/or suicidal thoughts and/or attempts.

Treatments implemented for subjects afflicted with PTSD include pharmaceutic intervention, and/or psychotherapy ("talk" therapy). Pharmaceutical intervention may, for example, call for administration of antidepressants to a subject afflicted PTSD. Antidepressants and other medications may be administered in conjunction with psychotherapy. Other medications, such as Prazosin, which is a sympatholytic drug used to treat high blood pressure, anxiety, and panic disorders, have also shown efficacy for the treatment of specific PTSD symptoms. Prazosin is an alpha-adrenergic blocker that is specific for the alpha-1 receptors. Although not currently approved by the Food and Drug Administration (FDA) for the treatment of PTSD, research indicates that Prazosin alleviates sleep problems, particularly nightmares, which are commonly experienced by PTSD patients. Persons of skill in the art refer to the FDA website for the latest information on patient medication guidelines, warnings, and newly approved medications for the treatment of PTSD.

Psychotherapy, which is sometimes referred to as "talk therapy", typically calls for regular and progressive counseling sessions wherein a PTSD patient talks in depth with a mental health professional. Psychotherapy may involve one-on-one or group therapy sessions. Talk therapy treatment for PTSD usually lasts 6 to 12 weeks, but it can last longer as required. Research has, furthermore, shown that support from family and friends can be an important part of recovery.

Some forms of psychotherapy target the symptoms of PTSD directly, while others focus on social, family, and/or job-related problems. A skilled practitioner may choose to combine different therapies depending on each person's needs.

Cognitive behavioral therapy (CBT) has been shown to confer therapeutic benefit to patients afflicted with PTSD. CBT may, for example, include: exposure therapy, whereby patients are trained to face and control their fear; and cognitive restructuring, whereby patients are trained to process and interpret the memories of the traumatizing event. Exposure therapy, for example, gradually exposes them to the trauma they experienced, but in a safe and controlled way. Exposure therapy uses mental visualization, writing, and/or visiting the place where the event happened and, in so doing, the therapist better enables patients with PTSD to cope with their feelings. Cognitive restructuring seeks to assist PTSD patients in more accurately understanding the traumatic event. In many circumstances, PTSD patients ascribe guilt and responsibility for the traumatic event to themselves and thereby amplify the emotional distress associated therewith. Cognitive restructuring helps the PTSD patient revisit the traumatic experience in a more realistic way.

While PTSD is considered as a binary state, namely one either has the condition or not, it is in fact a wide spectrum of disorders in which the cognitive functioning of the brain is distracted by over activity of the emotional part. Detection of such over emotional activity as well as detection of cognitive sub-functioning or distraction is of great importance for various methods of treatment. The spectrum of over activated emotional networks includes stress, anxiety, mood disorders, and attention problems as well as executive commands.

The technology and methods described herein may, for example, be used to track over-activity of the sympathetic system for diagnostic purposes and/or to provide indications as to the therapeutic efficacy of a medical intervention implemented for the treatment of PTSD. The technology and methods described herein may further be used to track over emotional activity as well as detection of cognitive sub-functioning or distraction. The spectrum of over activated emotional networks includes stress, anxiety, mood disorders, and attention problems as well as executive commands. Parameters that may be adjusted using the technology and methods described herein include indications as to the desired duration of therapy, type of therapy or combinations thereof, and assessment of therapeutic efficacy on an ongoing basis.

In some embodiments, the apparatus of the present invention is used in the management of pain, which may for example be general, chronic, acute, perceived, and/or migraine pain. The spectrum of over activated emotional networks includes stress, anxiety, mood disorders, and attention problems as well as executive commands. Parameters that may be adjusted using the technology and methods described herein include indications as to the desired duration of therapy, type of therapy or combinations thereof, and assessment of therapeutic efficacy on an ongoing basis.

In some embodiments, the apparatus of the present invention is used in the management of phantom pain refers to a type of perceived pain that can range from mild to extreme. Phantom pain generally relates to pain that is perceived to emanate from a peripheral body part that has been severed from main body. One example of phantom pain is phantom limb pain, which relates to mild to extreme pain experienced in the area of main body from which the severed limb was excised. Limb amputations may occur via accidental means or may be medically recommended to prolong or preserve a subject's life (e.g., circumstances wherein an amputation is required to remove a limb riddled with cancer cells or to remove a gangrenous limb) or to improve the quality of a subject's life (e.g., circumstances wherein an amputation is required to remove a body part that is a chronic source of pain). Phantom limb pain typically disappears or decreases over time, but when the condition persists for more than six months, the prognosis for improvement is poor.

Phantom limb pain is thought to be caused by the ongoing signaling of nerve endings at the site of the amputation, whereby pain signals continue to be transmitted to the brain such that the brain perceives that the limb is still attached to the main body. The brain's memory of pain may, furthermore, be retained and is interpreted as pain in a manner independent of signals from injured nerves. In addition to pain, some people experience sensations of tingling, cramping, heat, and/or cold that are perceived to emanate from the portion of the limb that was removed.

Medical intervention for the treatment of phantom limb pain is challenging and depends on the subject's level of pain. Treatments include, for example, heat application, biofeedback to reduce muscle tension, relaxation techniques, massage of amputated stump, injections of local anesthetics and/or steroids in the amputated stump, nerve blocks, surgery to remove scar tissue potentially entangling a nerve, physical therapy, transcutaneous electrical nerve stimulation (TENS) of the stump, neurostimulation techniques such as spinal cord stimulation or deep brain stimulation, and/or medications such as pain relievers, neuroleptics, anticonvulsants, antidepressants, beta-blockers, and sodium channel blockers.

The technology and methods described herein may, for example, be used to monitor the amputee's brain activity responsive to ongoing signaling of nerve endings at the site of the amputation and/or the brain's memory of pain for diagnostic purposes and/or to provide indications as to the therapeutic efficacy of a medical intervention implemented for the treatment of, for example, phantom limb pain. Parameters that may be adjusted using the technology and methods described herein include indications as to the desired duration of therapy, type of therapy or combinations thereof, and assessment of therapeutic efficacy on an ongoing basis. The technology can monitor pain, can indicate the onset or strengthening of the feeling of pain and can thus be used to alert the patient and caregiver, initiate or suggest timely usage of drugs or pain releasing stimuli and be part of a system that can alter the lifestyle to reduce the overall feeling of pain. All this accounts for all types of pain, migraine, and anxiety attacks as well as epileptic activity and seizures.

Further to the above, the technology and methods described herein may be used to monitor an individual's brain activity, and other physiological parameters, and environmental parameters, to correlate the monitored brain activity with the physiological and environmental parameters, and from the correlation, to detect changes in the individual's cognitive ability and/or brain state. As described herein, such correlations may be used to diagnose a condition or disorder in a subject and/or to provide indications as to the therapeutic efficacy of a medical intervention implemented for the treatment of the condition or disorder in the subject. Parameters that may be adjusted using the technology and methods described herein include indications as to the desired duration of therapy, type of therapy or combinations thereof, and assessment of therapeutic efficacy on an ongoing basis.

Determination of the Subject's Mental State, Neurological Condition, or Both

Decomposing EEG signals into different components is an effective tool to study brain activity and brain states, and deducing the role of certain functional regions of the brain, or neural networks in the brain for a given brain state. Without being limited by any particular theory, a particular brain state is associated with a particular mental state, a particular neurological condition, or a particular combination of a mental state and a neurological condition.

Without being intended to be limited by any particular theory, brain activity, detected via conventional EEG, is associated with a number of frequency bands from around 0.5 Hz (Delta waves) to Gamma waves which are above 32 Hz. In between are Theta, Alpha, and Beta waves, among others. However, it is assumed EEG electrodes are only sensitive to electrical signals which emanate from a small region of the brain, close to each electrode. Consequently, it is customary to record EEG activity with a large number of electrodes which cover the whole head. The location of the brain responsible for the detected electrical activity is calculated by estimating the phase of the electrical signal as it arrives to different electrodes. The BAFs described above may include these frequency bands as well.

In some embodiments of the present invention, the determining the role of certain regions or neural networks within the brain for a given cognitive function or mental state is not required. In some embodiments, the electrical activity of the brain of a subject is recorded using two electrodes (e.g., Fp1 and Fp2) located on the forehead of the subject. In some embodiments, either the Fp1, or the Fp2 electrode is used as a reference electrode, and the recorded electrical activity is the difference in between the Fp1 and Fp2 electrode. Alternatively, in some embodiments, the FpZ electrode may be used as either the reference, or recording electrode.

In some embodiments, the present invention provides a computer implemented method including:
  a. obtaining, in real-time, by a specifically programmed processor, electrical signal data representative of brain activity of a particular individual;
  b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
    wherein the pre-determined predictor associated with a particular brain state includes:
      i. a pre-determined mother wavelet,
      ii. a pre-determined representative set of wavelet packet atoms, created from the pre-determined mother wavelet,
      iii. a pre-determined ordering of wavelet packet atoms, and
      iv. a pre-determined set of normalization factors,
    wherein the processing includes:
      i. causing, by the specifically programmed processor, the electrical signal data to be deconstructed into a plurality of pre-determined deconstructed wavelet packet atoms, utilizing the pre-determined representative set of wavelet packet atoms,
        wherein time windows of the electrical signal data are projected onto the pre-determined representative set of wavelet packet atoms
        wherein the projection is via convolution or inner product, and
        wherein each pre-determined representative wavelet packet atom corresponds to a particular pre-determined brain activity feature from a library of a plurality of pre-determined brain activity features;
      ii. storing the plurality of pre-determined deconstructed wavelet packet atoms in at least one computer data object;
      iii. optionally causing, by the specifically programmed processor, the stored plurality of pre-determined deconstructed wavelet packet atoms to be re-ordered within the computer data object, based on utilizing a pre-determined order;
      iv. obtaining a statistical measure of the activity of each of the re-ordered plurality of pre-determined deconstructed wavelet packet atoms; and v. normalizing the re-ordered plurality of pre-determined wavelet packet atoms, based on utilizing a pre-determined normalization factor; and
    a. outputting, a visual indication of at least one personalized mental state of the particular individual, at least one personalized neurological condition of the particular individual, or both, based on the processing,
wherein the individual pre-determined predictor associated with a particular brain state from within the plurality of pre-determined predictors is generated by the steps including:
    i. obtaining the pre-determined representative set of wavelet packet atoms by:
        a. obtaining from a plurality of individuals, by the specifically programmed processor, at least one plurality of electrical signal data representative of a brain activity of a particular brain state;
        b. selecting a mother wavelet from a plurality of mother wavelets,
        wherein mother wavelet is selected from an wavelet family selected from the group consisting of: Haar, Coiflet Daubehies, and Mayer wavelet families;
        c. causing, by the specifically programmed processor, the at least one plurality electrical signal data to be deconstructed into a plurality of wavelet packet atoms, using the selected mother wavelet;
        d. storing the plurality of wavelet packet atoms in at least one computer data object;
        e. determining, an optimal set of wavelet packet atoms using the pre-determined mother wavelet, and storing the optimal set of wavelet packet atoms in at least one computer data object,
        wherein the determining is via utilizing a Best Basis algorithm; and
        f. applying, by the specifically programmed processor, wavelet denoising to the number of wavelet packet atoms in the optimal set;
    ii. obtaining the pre-determined ordering of wavelet packet atoms by:
        a. projecting, by the specifically programmed processor, the at least one plurality of electrical signal data representative of a brain activity for each 4 second window of the data onto the pre-determined representative set of wavelet packet atoms;
        b. storing the projections in at least one computer data object;
        c. determining, by the specifically programmed processor, the wire length for every data point in the projection by determining the mean absolute distance of the statistical measure of the projections of different channels from their adjacent channels;
        d. storing the wire length data in at least one computer data object; and
        e. optionally re-ordering the stored projections, by the specifically programmed computer to minimize a statistical value of the wire length value across each time window, and across all individuals within the plurality of individuals, and across the projections; and
    iii. obtaining the pre-determined set of normalization factors by:
        a. determining, by the specifically programmed computer, the mean and standard deviation of the values of the stored projections.

In some embodiments, the computer implemented method further comprises:
    a. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
    b. determining a relationship between the obtained data and the visual indication of at least one personalized mental state of the particular individual, at least one personalized neurological condition of the particular individual, or both.

In some embodiments, the electrical signal data representative of brain activity of a particular individual is recorded using two electrodes located on the forehead of the particular individual.

Figure 2:
FIG. 2 shows a screenshot of recording electrodes according to some embodiments of the present invention.

An example of recording electrodes according to some embodiments of the present invention is shown in FIG. 2. In some embodiments, the electrical activity of the brain of a subject is recorded using between one and three electrodes located on the forehead of the subject. In some embodiments, the electrical activity of the brain of a subject is recorded using between one and three electrodes located at region(s) of the head which is/are other than or in addition to the forehead of the subject. For example, in some embodiments, at least one electrode is located behind or on, or in an ear of the subject. For example, in some embodiments, at least one electrode is part of an item positioned on the head of the subject, where the item is configured for at least one additional function in addition to hosting the at least one electrode. For example, in some embodiments, the item is a headwear piece (e.g., hat). For example, in some embodiments, the item is an electronic device (e.g., headphones).

In some embodiments, the item positioned on the head of the subject further comprises at least one sensor selected from the group consisting of: an accelerometer, a gyroscope, a pulse meter, an oximeter, a pressure sensor, a heart rate monitor, and a temperature sensor.

In some embodiments, the item positioned on the head of the subject is further configured to detect at least one physiological parameter selected from the group consisting of: EEG, fNIRS, GSR, facial expression, muscle tone, temperature, heart rate, blood flow, blood oxygen and/or carbon dioxide levels, blood inflation level, blood coagulation level, heart rate variability, blood flow morphology, and head acceleration.

In some embodiments, the electrical activity of the brain of a subject is recorded according to the methods disclosed in G. Castellani, et al., Frontiers in Genetics Vol 5, pg 1-12 (2014).

In some embodiments, the electrical signal data representative of brain activity of a particular individual is recorded with a sufficiently large sampling rate above 250 and a dynamic range configured to detect sufficient cortical activity in the desired location of the brain. For example, a larger dynamic range is expected to detect more cortical activity than a smaller dynamic range. In one embodiment, the dynamic range is 15 bit resolution of the analog-to-digital (A/D) and above.

In some embodiments, the particular individual is performing a specific cognitive task.

In some embodiments, the specific cognitive task is selected from the group including short and/or long term memory recall, e-learning, meditation, and concentration.

In one embodiment, the particular individual has a particular brain state at a certain time.

Processing the Recorded Electrical Signal Data Representative of Brain Activity of a Particular Individual According the Method of Some Embodiments of the Present Invention Deconstructing the recorded electrical signal data representative of brain activity of a particular individual: In some embodiments, the recorded electrical signal data representative of brain activity of a particular individual is recorded in real-time over a certain time period. In some embodiments, the electrical signal data representative of brain activity of a particular individual is recorded for up to one hour. In some embodiments, the electrical signal data representative of brain activity of a particular individual is recorded for up to 50 minutes. In some embodiments, the electrical signal data representative of brain activity of a particular individual is recorded for up to 40 minutes. In some embodiments, the electrical signal data representative of brain activity of a particular individual is recorded for up to 30 minutes. In some embodiments, the electrical signal data representative of brain activity of a particular individual is recorded for up to 20 minutes. In some embodiments, the electrical signal data representative of brain activity of a particular individual is recorded for up to 10 minutes.

In some embodiments, the real-time recorded electrical signal data representative of brain activity of a particular individual is deconstructed into a plurality of pre-determined deconstructed wavelet packet atoms, utilizing a pre-determined representative set of wavelet packet atoms. Each individual pre-determined deconstructed wavelet packet atom within the plurality of pre-determined deconstructed wavelet packet atoms corresponds to a brain activity feature ("BAF").

In some embodiments, the a pre-determined representative set of wavelet packet atoms is created from a pre-determined mother wavelet, selected from an wavelet family selected from the group including, but not limited to: Haar, Coiflet Daubehies, and Mayer wavelet families. Other wavelet families suitable for mother wavelets according to some embodiments of the present invention are described in the website located at http://www.mathworks.com/help/wavelet/ref/waveletfamilies.html?refresh=true.

In some embodiments, recorded electrical signal data representative of brain activity of a particular individual is deconstructed into a plurality of pre-determined deconstructed wavelet packet atoms, utilizing a pre-determined representative set of wavelet packet atoms according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Intrator, N, Neural Computation 5, 443-455 (1993), whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Intrator, N, Neural Computation 4, 98-1-7 (1992), whose such specific disclosure is incorporated herein by reference.

Re-Ordering the Plurality of Pre-Determined Deconstructed Wavelet Packet Atoms:

In some embodiments, the plurality of pre-determined wavelet packet atoms is reordered, according to a pre-determined order. In some embodiments, the re-ordered plurality of pre-determined wavelet packet atoms, is normalized, utilizing a pre-determined normalization factor. In some embodiments, the plurality of pre-determined wavelet packet atoms is only normalized.

In some embodiments, utilizing electrical data recorded via standard EEG recording electrodes, the exemplary specifically programmed processor of the present invention is programmed to first normalize each wavelet packet atom, outputted by at least one band-pass filter, separately based on a dataset of collected data from multiple individuals to determine the distribution of the representation values for each of the wavelet packet atoms separately. In some embodiments, the at least one band-pass filter has 2-36 channels. In some embodiments, the at least one band-pass filter has at least 12 channels. In some embodiments, the at least one band-pass filter has at least 16 channels. In some embodiments, the at least one band-pass filter has at least 32 channels.

The Visual Indication of at Least One Personalized Mental State of the Particular Individual:

In some embodiments, the normalized, re-ordered plurality of a statistical measure of projections onto pre-determined wavelet packet atoms is assembled into a visual representation, wherein each individual normalized pre-determined wavelet packet atom in the plurality, corresponds to a BAF, and is arranged in the representation according the pre-determined order. As used herein, a "BAFs representation" refers to a visual representation of the normalized, re-ordered plurality of pre-determined projections onto wavelet packet atoms. An example of a BAFs representation of a subject according to some embodiments of the present invention is shown in FIG. 3.

In some embodiments, the BAFs representation of the particular individual has 121 individual BAFs. Alternatively, in some embodiments, the BAFs representation of the particular individual has up to 200 individual BAFs. Alternatively, in some embodiments, the BAFs representation of the particular individual has from 10 to 200 individual BAFs. Alternatively, in some embodiments, the BAFs representation of the particular individual has from 1 to 1000 individual BAFs. Alternatively, in some embodiments, the BAFs representation of the particular individual has from 30 to 1000 individual BAFs. Alternatively, in some embodiments, the BAFs representation of the particular individual has at least 30 individual BAFs. Alternatively, in some embodiments, the BAFs representation of the particular individual has a number of individual BAFs which is a multiple (e.g., 2×, 3×, 4×, 5×, 6×, etc.) of a number BAFs being recorded.

In some embodiments, the BAFs representation of the subject has 121 individual BAFs. Alternatively, in some embodiments, the BAFs representation of the subject over 200 individual BAFs. Alternatively, in some embodiments, the BAFs representation of the subject has from 10 to 200 individual BAFs. Alternatively, in some embodiments, the BAFs representation of the subject has from 1 to 1000 individual BAFs. Alternatively, in some embodiments, the BAFs representation of the subject has from 30 to 1000 individual BAFs. Alternatively, in some embodiments, the BAFs representation of the subject has at least 30 individual BAFs. Alternatively, in some embodiments, the BAFs representation of the subject has a number of individual BAFs which is a multiple (e.g., 2×, 3×, 4×, 5×, 6×, etc.) of a number of neural networks being analyzed. In some embodiments, the BAFs include traditional EEG recordings.

Figure 3:
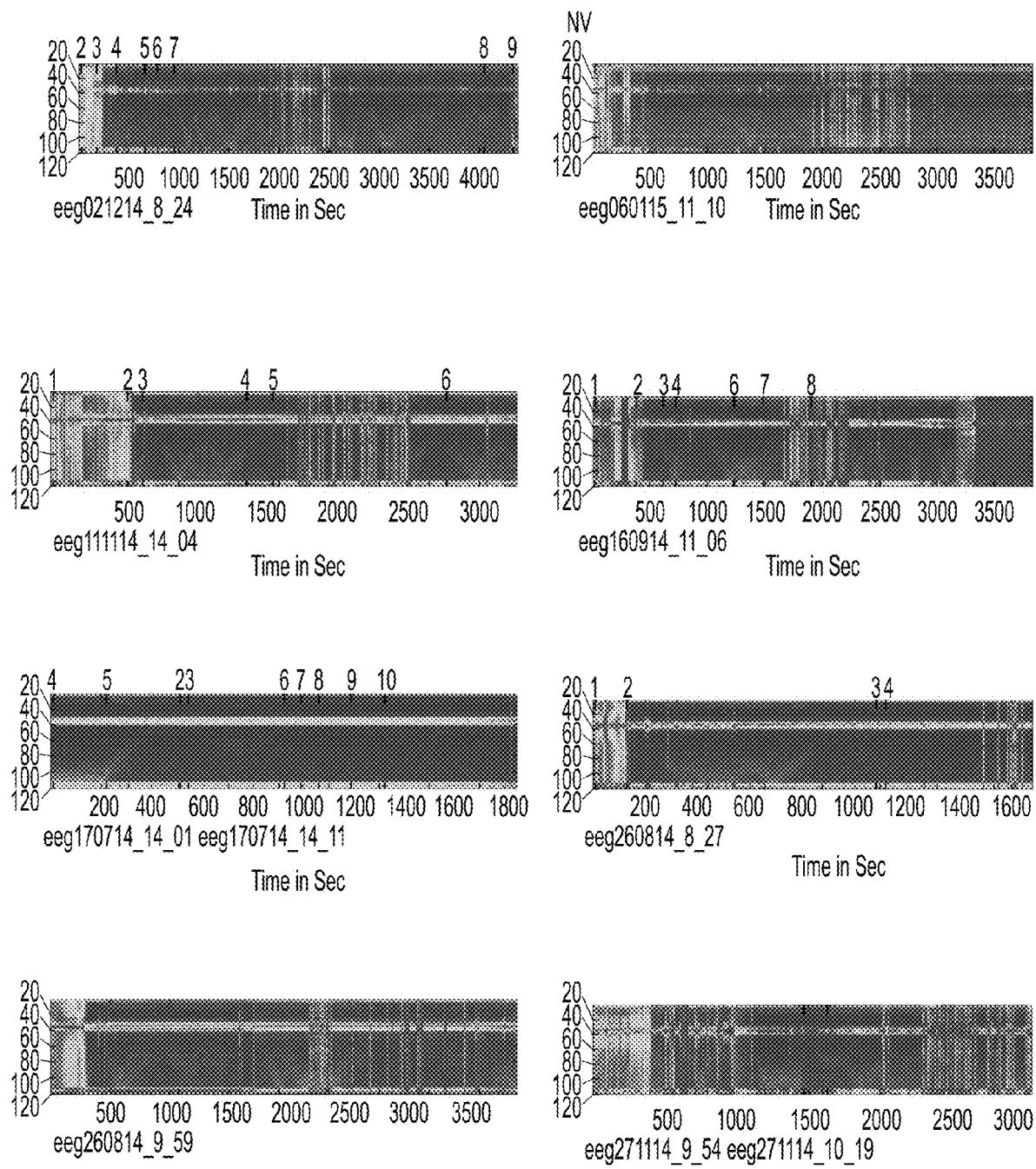
FIG. 3 shows a screenshot of an example of a representation of a recording for a brain activity feature of a subject according to some embodiments of the present invention.

Referring to FIG. 3 as an example, each line perpendicular to the y axis represents an activity of a projection onto a single pre-determined wavelet packet atom, (also referred to herein as a BAF). For example, the activity can be represented via at least one suitable statistical measurement of a projection onto a single wavelet packet atom or a group of wavelet packet atoms, where the suitable statistical measurement can be, but not limited to, mean, standard deviation, and the like. In some embodiments, the BAFs representation can be color coded. For example, as shown in FIG. 3, various activity area(s) on an intensity spectrum can be presented, for example but not limited to, by presenting high activity area(s) as more darkly shaded regions of at least one particular color ("hot") to low activity tends area(s) as more lighted shaded region(s) of the at least one color or at least one other color ("cold"), and any continuous shading in between based on corresponding activity level. Each column perpendicular to the x axis represents a vector of brain activity state (the BAFs representation) at a specific time or specific time period. Thus, the x axis is measured in time (e.g., milliseconds, seconds, minutes, hours, days, etc.). In some embodiments, the image is normalized by a suitable non-linear transformation such as, for example, histogram equalization, prior to the color coding each brain activity (BAF) of the plurality of BAFs.

In some embodiments, the exemplary specifically programmed processor of the present invention is programmed to cluster the electrical signal data representative of brain activity of a particular individual before a pre-determined predictor is determined. For example, the exemplary specifically programmed processor of the present invention is programmed to generate a collection of m-dimensional vectors from projections on m pre-determined deconstructed wavelet packet atoms which can be further clustered into different brain states. In some embodiments, the exemplary specifically programmed processor of the present invention is programmed to determine a number of brain states by using at least one machine learning technique. For example, the exemplary specifically programmed processor of the present invention is programmed to utilize hierarchical clustering to analyze the clustered data and to decide which clusters to group together based on the relative distance between their members.

In some embodiments, the exemplary specifically programmed processor of the present invention is programmed to utilize the cluster membership construct the plurality of pre-determined predictors based, at least in part, on:

1) the distance from a cluster center or from different members of the cluster, and/or
2) a sequence of cluster membership that preceded the current frame.

For example, the exemplary specifically programmed processor of the present invention is programmed to utilize at least one temporal model (e.g., but not limited to, a Markov chain, a hidden Markov model, other similarly suitable models) based on the cluster membership to determine a particular predictor of the library of predictors.

In some embodiments, after the cluster membership is assigned to each window frame, the exemplary specifically programmed processor of the present invention is programmed to generate at least one temporal structure probabilistic model. For example, in text analysis, from the data, the exemplary specifically programmed processor of the present invention is programmed to: construct the vocabulary of letters (specific clusters); identify words based on segmentation of letters, construct the words vocabulary from the identified words, and, interpret particular grammatical rules to create sentences from the words. For example, the first step is to construct a matrix of probability to move from one letter to the other.

In some embodiments, the temporal structure probabilistic model is used to determine the correlation between the at least one stimulus applied and the observed brain activity. In some embodiments, a strong correlation indicates a coherent response to the at least one stimulus.

In some embodiments, the degree of response ("RtS") is used to identify the at least one stimulus that the subject is capable of responding to. By way of illustration, RtS determine whether the subject responds in a consistent way to visual stimuli, auditory stimuli, other sensory stimuli, commands etc.

Identification of an Underlying Mental State, an Underlying Neurological Condition, or a Combination of an Underlying Mental State and Neurological Condition According the Method of Some Embodiments of the Present Invention In some embodiments, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm selected from the group consisting of logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In some embodiments, the exemplary specifically programmed processor of the present invention is programmed to identify an underlying mental state, an underlying neurological condition, or a combination of an underlying mental state and an underlying neurological condition, in the particular individual utilizing at least one machine learning algorithm such as, but not limited to, logistic regression modeling, support vector machine modeling, and a deep learning modeling. Specifically, in some embodiments, the exemplary specifically programmed processor of the present invention is programmed to execute at least the following steps:

1) separating the electrical signal data representative of brain activity of a particular individual into training, validation and test data sets;
2) generating a family of models based on the training set, adjusted based on the validation set;
3) testing the performance of each model on the test set;
4) repeating steps 1-3 for different parameters of a particular AI model (e.g. the regularization parameter in a ridge regression model; the number of hidden units in a feed forward neural network; the weight decay parameter in a feed forward neural network; types and a number of kernels in a kernel model such as support vector machine; a combination of Gaussians and the regularization parameters in a support vector machine; a combination of Gaussians models; etc.); and
5) after a set of model parameters is determined, obtaining prediction results on a new data set and repeat the steps 1-4 for different families of orthogonal decomposition and other model parameters obtained from the recorded electrical signal data representative of brain activity of a particular individual.

In some embodiments, electrical signal data representative of brain activity of a particular individual is recorded when the particular individual has a particular mental state. In some embodiments, the particular mental state is unknown, and the methods according to some embodiments of the present invention are utilized to identify the particular mental state.

Examples of the particular mental state include, but are not limited to, seizure, fear, anxiety, pain, sleep states (e.g. REM sleep), awake, alert, fatigue, anaesthetized, meditation states, stress, other moods, different brain states associated with dementia, a lack of response, or inappropriate response to external stimuli associated with autism, or autism spectrum disorder, and the like. An example of a BAFs representation of a subject having a particular mental state is shown in FIG. 4.

Figure 4A:
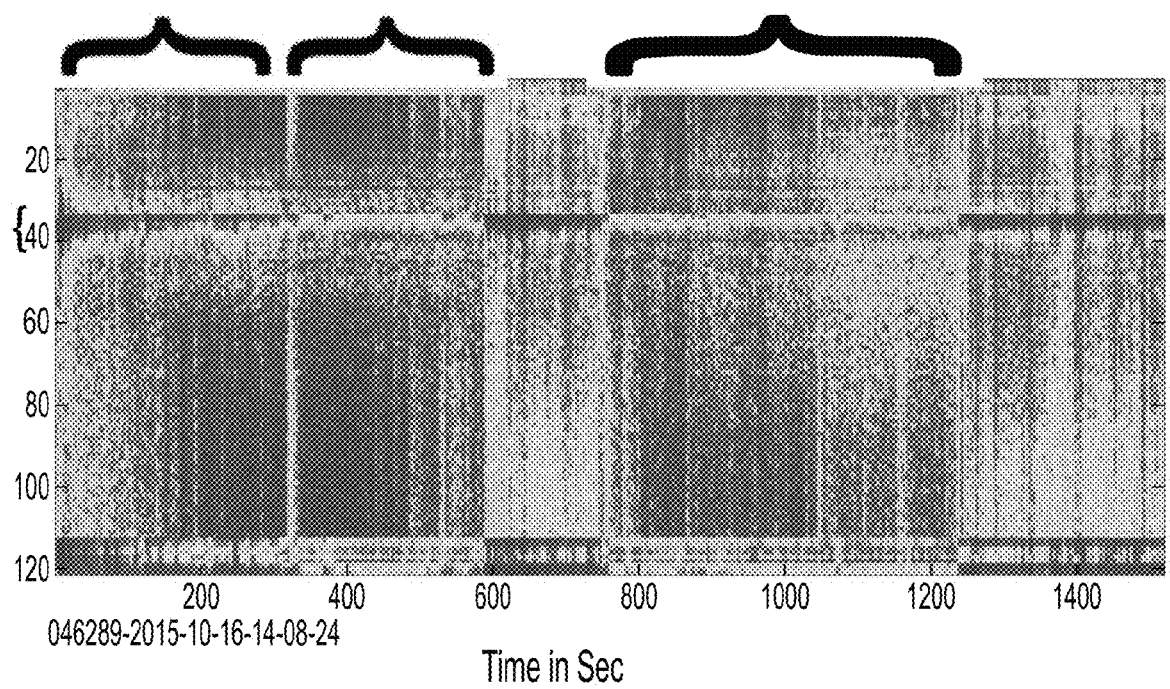
FIG. 4A and FIG. 4B shows a screenshot of examples of representations of recordings for brain activity features of subjects according to some embodiments of the present invention.

Referring to FIG. 4A, shows the brain activity representation of an experienced yogi that is performing three types of meditation (indicated via the horizontal brackets). After the first two meditations and after the third meditation, the yogi explains what he is doing. A range in BAFs is indicated with the vertical brackets. This collection of BAFs is associated with awareness. It is clear that one meditation emphasizes only these awareness channels, and it is evident in the activity when the yogi explains what meditation he is doing.

Figure 4B:
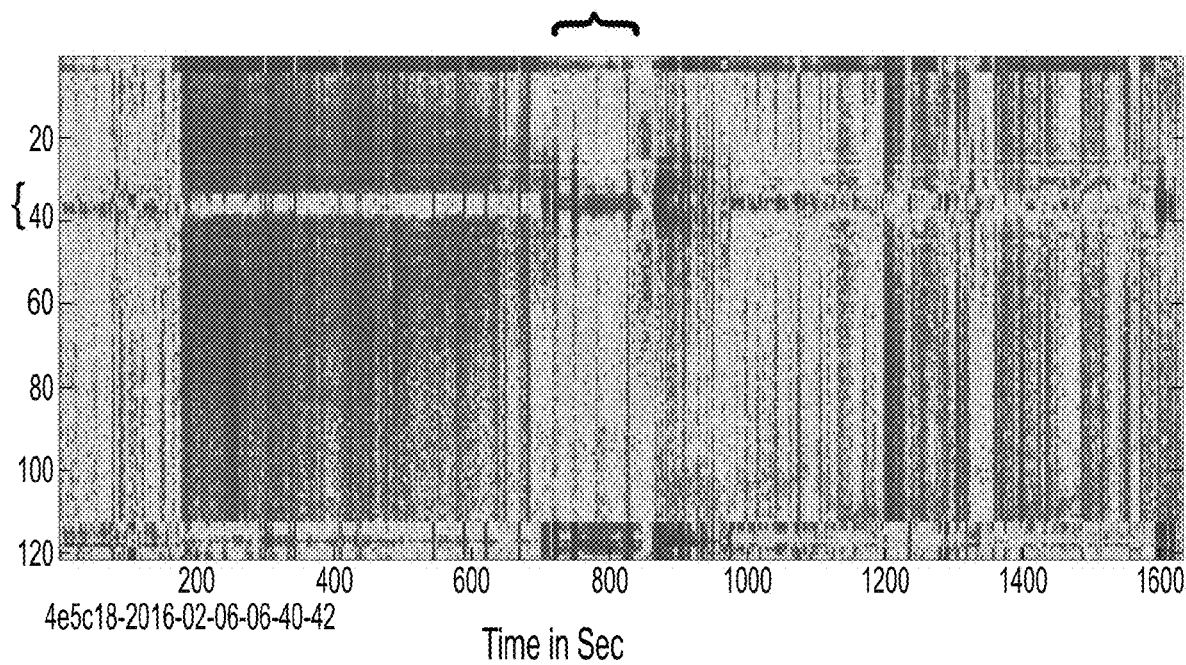

Referring to FIG. 4B, a BAFs representation is shown from an individual in a vegetative state. The BAFs highlights in FIG. 4A are shown, and are not active. However, administration of a medical brain stimulation to the individual was able to activate the BAFs associated with awareness for a short period of time. This provides an example to the ability to determine the effect of medications with the BAF representation.

In some embodiments, the electrical signal data representative of brain activity of a particular individual is recorded when the particular individual is performing a specific cognitive task. In some embodiments, the methods according to some embodiments of the present invention identify an underlying mental state, an underlying neurological condition, or a combination of an underlying mental state and an underlying neurological condition, based, at least in part, on the electrical signal data representative of brain activity of a particular individual recorded while the particular individual is performing the specific cognitive task.

Examples of the specific cognitive task include, but are not limited to, short and long term memory recall, identification of stimuli, meditation, learning, watching a movie, observing images, intense concentration during motor operation, response to a sensory stimulus, and the like. An example of a BAFs representation of a subject performing a specific cognitive task is shown in FIG. 3.

In some embodiments, the sensory stimulus can be auditory, tactile, olfactory, visual, and the like.

In some embodiments, the assignment of at least one specific brain state to the visual indication of at least one personalized mental state of the particular individual identifies an abnormality in at least one neural network in the brain of the particular individual associated with a particular neurological condition.

In some embodiments, the abnormality in at least one neural network in the brain of the particular individual is used to diagnose the particular individual having a neurological condition.

Figure 5:
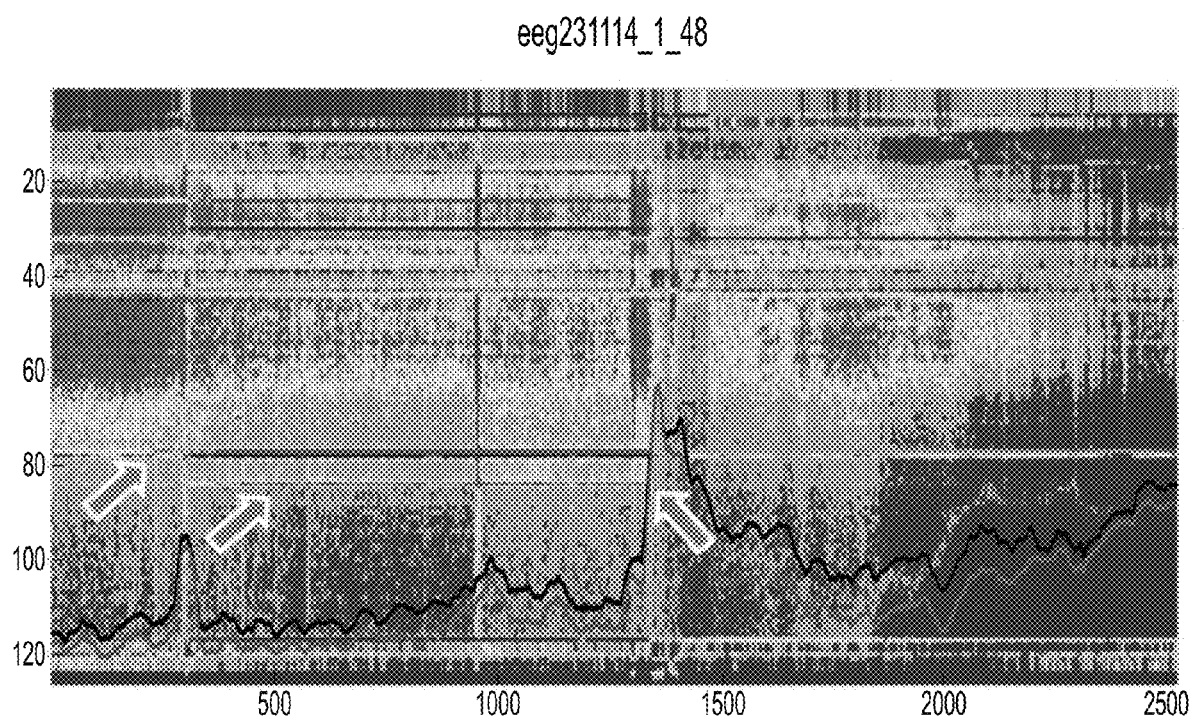
FIG. 5 shows a screenshot of an example of a brain activity features (BAFs) representation of a subject according to some embodiments of the present invention.

In some embodiments, the neurological condition is selected from the group consisting of, Alzheimer's disease, dementia, stress, fatigue, anxiety, epilepsy, traumatic brain injury, PTSD, loss of cognitive function, coma, a lack of response, or inappropriate response to external stimuli associated with autism, or autism spectrum disorders, a lack of concentration, and sleep disorders. An example of a BAFs representation of a subject with a neurological condition is shown in FIG. 5.

In some embodiments, the particular individual's neurological condition is unknown, and the methods according to some embodiments of the present invention identify the neurological condition.

In some embodiments, the at least one specific brain state is used to determine the emotional state of the particular individual.

In some embodiments, the particular individual is receiving a therapy, and the visual indication of at least one personalized mental state of the particular individual is used to determine the effectiveness of the therapy.

For example, by way of illustration, early intervention in autism patients, at around 6 months of age can improve the treatment of autism. In another example, an earlier detection of abnormal activity in at least one neuronal network that is associated with epilepsy in the brain of an individual can improve the treatment of epilepsy, or warn the individual, or the individual's care giver that a seizure is occurring, or will occur. In another example, an earlier detection of abnormal activity in at least one neuronal network that is associated with migraine in the brain of an individual can improve the treatment of migraine, or warn the individual, or the individual's care giver that a migraine is occurring, or will occur. In another example, an earlier detection of abnormal activity in at least one neuronal network that is associated with an ischemic event in the brain of an individual can improve the treatment of ischemic injury, or warn the individual, or the individual's care giver that an ischemic event, such as, for example, a transient ischemic event, or stroke is occurring, will occur, or has occurred. In some embodiments, the brain activity of the particular individual may be recorded whilst the subject is asleep, which, in the case of certain ischemic conditions, is when such conditions are more likely to occur.

In some embodiments, the particular individual is receiving a therapy, and the visual indication of at least one personalized mental state of the particular individual is used to determine the nature of the therapy to be administered.

In some embodiments, the particular individual is receiving a therapy, and the visual indication of at least one personalized mental state of the particular individual is used to determine the duration of the therapy.

In some embodiments, the particular individual is receiving a therapy, and the visual indication of at least one personalized mental state of the particular individual is used to determine the dosing regimen of the therapy.

In some embodiments, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In some embodiments, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In some embodiments, the migraine therapy is a medication. Alternatively, in some embodiments, the migraine therapy is guided imagination. Alternatively, in some embodiments, the migraine therapy is hypnosis. Alternatively, in some embodiments, the migraine therapy is meditation.

In some embodiments, in contrast to the analysis of fetal brain activity using Amplitude Integrated EEG which typically detects the two brain conditions of sleep and awake states, and the dynamics of shift from one state to the other to identify the degree of brain damage, the exemplary specifically programmed processor of the present invention is programmed to perform group analysis on a group of brain states of infants, and determine the brain states of the infant at a certain time.

In another example, in neural marketing, in some embodiments, the exemplary specifically programmed processor of the present invention is programmed to perform group analysis on a group of brain states in individuals receiving a stimulation at each time frame, and to determine the proportions in the group that are in the same brain state at a given window frame. This enables to measure the engagement of the group with the stimulation, as when a larger portion of the group is found in the same brain state, it is likely that this happens due to the stimulation, thus the group is considered to be engaged and reacting to the stimuli. The specific brain state, at which a portion of the group is in, can correspond to the specific reaction to the stimuli, allowing for feedback training.

In some embodiments, the methods of the present invention determine a mental state of a particular individual at a first time point. In some embodiments, brain of the particular individual changes from one mental state to another, but remains in a first mental state for the majority of the time. In some embodiments, the first mental state is not favorable. In some embodiments, the system may supply a stimulus that encourages the brain of the particular individual to enter a second, more favorable mental state, via neural feedback. For example, by way of illustration, the particular individual may be in a coma, and the first mental state may be a state of non-responsiveness. The system may supply a stimulus that encourages the brain of the particular individual to enter a second, more responsive mental state.

In another example, the patient may have an autism spectrum disorder, and the first mental state may be the individual refusing, or being unable to maintain eye contact with another person. The system may supply a stimulus that encourages the brain of the particular individual to enter a second mental state where the individual is more easily capable of maintaining eye contact.

The Plurality of Pre-Determined Predictors

In some embodiments, an individual pre-determined predictor associated with a particular brain state within the plurality of pre-determined predictors is generated by the steps including:
i. obtaining the pre-determined representative set of wavelet packet atoms by:
   a. obtaining from a plurality of individuals, by the specifically programmed processor, at least one plurality of electrical signal data representative of a brain activity of a particular brain state;
   b. selecting a mother wavelet from a plurality of mother wavelets,
      wherein mother wavelet is selected from an wavelet family selected from the group consisting of: Haar, Coiflet Daubehies, and Mayer wavelet families;
   c. causing, by the specifically programmed processor, the at least one plurality of electrical signal data to be deconstructed into a plurality of wavelet packet atoms;
   d. storing the plurality of wavelet packet atoms in at least one computer data object;
   e. determining, an optimal set of wavelet packet atoms, and storing the optimal set of wavelet packet atoms in at least one computer data object,
      wherein the determining is via utilizing a Best Basis algorithm; and
   f. applying, by the specifically programmed processor, wavelet denoising to the number of wavelet packet atoms in the optimal set;
ii. obtaining the pre-determined ordering of wavelet packet atoms by:
   a. projecting, by the specifically programmed processor, the at least one plurality of electrical signal data representative of a brain activity for each 4 second window of the data onto the pre-determined representative set of wavelet packet atoms;
   b. storing the projections in at least one computer data object;
   c. determining, by the specifically programmed processor, the wire length for every data point in the projection by determining the mean absolute distance of the statistical measure of the projections of different channels from their adjacent channels;
   d. storing the wire length data in at least one computer data object; and
   e. optionally re-ordering the stored projections, by the specifically programmed computer to minimize a statistical value of the wire length value across each time window, and across all individuals within the plurality of individuals, and across the projections; and;
iii. obtaining the pre-determined set of normalization factors by:
   a. determining, by the specifically programmed computer, the mean and standard deviation of the values of the stored projections.

To generate a library of a plurality of pre-determined predictors requires an illustrative library of at least one plurality of electrical signal data representative of a brain activity of a particular brain state. Generation of an illustrative library of at least one plurality of electrical signal data representative of a brain activity of a particular brain state requires obtaining a sufficient collection of electrical signal data representative of a brain activity of a particular brain state (e.g., 100 recordings; 1,000 recording; 10,000 recordings; 100,000 recordings; 1,000,000 recordings, etc.) In general, a recording of 3000 seconds of each event, is sufficient for a robust detection of that brain state event. The larger the number of observations, the more robust the detection is. The electrical signal data representative of a brain activity of a particular brain state can be from a sufficient number of individuals (e.g., 100; 1,000; 10,000; 100,000; 1,000,000, etc.) and be recorded during various (e.g., different in kind, different in intensity, etc.) activities, cognitive tasks and neurological conditions, leading to a variety of brain states.

In some embodiments, the library of a plurality of predetermined predictors can be tailored to one or more specific goals. For example, if there is a need to emphasize on detection of a specific brain activity event, for example, detection of abnormalities which exist at a certain cortical location occurring before an epileptic seizure occurs, or at an early stage of migraine, then more emphasis should be put on recording during such times. Such emphasis is given by recording from a single subject at times when such event occurs, or recording from multiple subjects at those times. Another example may be recording from subjects that are performing an attention test such as T.O.V.A. test (The TOVA Company, Los Alamitos, Calif.). Then a recording of a number of subjects performing the same task is obtained, rather than recording from a number of subjects that exhibit a certain brain abnormality such as a certain type of epilepsy. In another example, based on the goal, in some embodiments, a plurality of subjects can be asked to perform a specific cognitive task. Examples of the specific cognitive task include, but are not limited to, memory recall, identification of stimuli, performing an attention task, meditation, learning, watching a movie, observing images, intense concentration during motor operation, and the like.

Deconstructing the at Least One Plurality of Electrical Signal Data:

In some embodiments, the at least one plurality of electrical signal data is recorded over a certain time period. In some embodiments, the at least one plurality of electrical signal data is recorded for up to one hour. In some embodiments, the at least one plurality of electrical signal data is recorded for up to 50 minutes. In some embodiments, the at least one plurality of electrical signal data is recorded for up to 40 minutes. In some embodiments, the at least one plurality of electrical signal data is recorded for up to 30 minutes. In some embodiments, the at least one plurality of electrical signal data is recorded for up to 20 minutes. In some embodiments, the at least one plurality of electrical signal data is recorded for up to 10 minutes.

In some embodiments, the recorded at least one plurality of electrical signal data is deconstructed into a plurality of deconstructed wavelet packet atoms. Each individual deconstructed wavelet packet atom within the plurality of deconstructed wavelet packet atoms corresponds to a brain activity feature ("BAF").

In some embodiments, the exemplary specifically programmed processor of the present invention is programmed deconstruct the at least one plurality of electrical signal data into a plurality of deconstructed wavelet packet atoms, with different mother wavelets, and other orthogonal decompositions such as but not limited to, orthogonal cosine transform and wavelet transform. In some embodiments, the exemplary specifically programmed processor of the present invention is programmed to utilize a particular orthogonal decomposition to minimize the decomposition processing time which is proportional to n log(n) time where n is the number of samples in a window frame.

In some embodiments, the mother wavelet is selected from a wavelet family selected from the group including, but not limited to: Haar, Coiflet Daubehies, and Mayer wavelet families. Other wavelet families suitable for mother wavelets according to some embodiments of the present invention are described in the website located at http://www.mathworks.com/help/wavelet/ref/waveletfamilies.html?refresh=true.

In some embodiments, the mother wavelet is an algorithm of adapting the mother wavelet (not just the decomposing wavelet packet atoms) for a given collection of signals. This is a further modification that can be performed when choosing a mother wavelet. See, for example, N. Neretti and N. Intrator *An Adaptive approach to wavelets filter design. IEEE Proceedings on Neural Networks for Signal Processing* pp. 317-326, September 2002; the entire content of which is incorporated herein by reference.

In some embodiments, the exemplary specifically programmed processor of the present invention is programmed to obtained, based on the orthogonal decomposition algorithm, a collection of n dimensional vectors, where each vector represents one BAF.

In some embodiments, the exemplary specifically programmed processor of the present invention is programmed to perform the decomposition to achieve at least one pre-determined goal. For example, the at least one pre-determined goal can be based on identifying a common Best Basis which achieves a particular discrimination at a particular coefficient distribution (an unsupervised/supervised hybrid goal) and which can be commonly utilized for the data analysis with respect to a group of individuals.

In some embodiments, the exemplary specifically programmed processor of the present invention is programmed to determine projections (convolutions) onto the chosen basis functions or some statistics of these projections to generate output interpretive of particular brain activity(ies) associated with particular BAF(s). For example, the exemplary specifically programmed processor of the present invention is programmed to determine particular BAF(s) based on an activity in each such projection. In some embodiments, the exemplary specifically programmed processor of the present invention is programmed to estimate the energy of each projection (e.g., the variance of the signal), a maximal value or other suitable statistical measurement of the orthogonal distribution, such as, but not limited to, a value of the negative entropy.

In some embodiments, the recorded at least one plurality of electrical signal data is deconstructed into a plurality of deconstructed wavelet packet atoms, according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

Specifically, the exemplary specifically programmed processor of the present invention identifies a smallest-entropy basis to be utilized in orthogonal decomposition of a particular at least one plurality of electrical signal data. In some embodiments, the exemplary specifically programmed processor of the present invention performs the Shannon entropy analysis on an at least one plurality of electrical signal data to obtain the joint best basis. When considering an at least one plurality of electrical signal data to obtain the joint best basis, the in one embodiment of this patent, it is possible to choose a map M to include additional characteristics which emphasize specific properties of the joint at least one plurality of electrical signal data. For example, if M(1) and M(2) satisfy the definition of the map M being the additive information cost functions, leading to an optimal basis which relies on the sum of both functions. In some embodiments, the exemplary specifically programmed processor of the present invention is programmed to add a new additive cost function which measures a distribution of coefficients at each node in a particular wavelet packet tree to identify the functional M which seeks wavelet packet coefficients with minimal Shannon entropy or with the modified additive optimization function (across the wavelet decomposition) on average across all data observations.

In some embodiments, the recorded at least one plurality of electrical signal data is deconstructed into a plurality of deconstructed wavelet packet atoms, according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 5, 443-455 (1993), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 4, 98-1-7 (1992), whose such specific disclosure is incorporated herein by reference.

For example, in some embodiments, the exemplary specifically programmed processor of the present invention is programmed to utilize a moving window frame along the time series to obtain different data observations result. In one example, the exemplary specifically programmed processor of the present invention is programmed to utilize a particular window frame and an overlap for the analysis of data segments. In one example, the exemplary specifically programmed processor of the present invention is programmed to utilize a window frame of 4 seconds with an overlap of 75% between consecutive window frames. In some embodiments, the exemplary specifically programmed processor of the present invention is programmed to utilize the window which has a length that is an exponent of 2, so, for example, if sampling rate is 256 Hz, a 4 second window would result in 1024 samples. In another example, if the sampling frequency of 250 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2).

In another example, the exemplary specifically programmed processor of the present invention is programmed to utilize a window frame which progresses by 1 second between adjacent frames to obtain vector updates every one second, thus generating a projections matrix of size 121×N (the number of seconds in the data)−3 (due to the first frame of 4 seconds and then each frame progresses by 1 second). In some embodiments, the exemplary specifically programmed processor of the present invention is programmed to rescaling the full matrix to obtain the maximal dynamic range of the visual map of the data.

Determination of the optimal set: In some embodiments, the optimal set of wavelet packet atoms is determined according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition In some embodiments, the optimal set of wavelet packet atoms is determined according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the optimal set of wavelet packet atoms is determined according to another suitable Best Basis algorithm disclosed in Intrator, N, Neural Computation 5, 443-455 (1993), whose such specific disclosure is incorporated herein by reference.

In some embodiments, the optimal set of wavelet packet atoms is determined according to another suitable Best Basis algorithm disclosed in Intrator, N, Neural Computation 4, 98-1-7 (1992), whose such specific disclosure is incorporated herein by reference.

In some embodiments, the number of wavelet packet atoms in the optimal set is reduced by application of the wavelet denoising algorithm disclosed in Donoho D. L., IEEE Transactions on Information Theory, 41(3), 613-627 (1995).

In some embodiments, the number of wavelet packet atoms in the optimal set is reduced by application of an L1 denoising method.

In some embodiments, the number of wavelet packet atoms in the optimal set is reduced by application of an L2 denoising method.

In some embodiments, the number of wavelet packet atoms in the optimal set is reduced by application of a hard threshold method.

Re-ordering the plurality of deconstructed wavelet packet atoms: In some embodiments, the denoised optimal set of wavelet packet atoms is reordered, so that more physiologically correlated BAFs, based on analysis of the total signal data, are visually presented to be geographically/spatially closer, as, for example shown in FIG. 6.

In some embodiments, the reordering is optional.

In some embodiments, the denoised optimal set of wavelet packet atoms is reordered by the specifically programmed computer performing the steps consisting of:
1. determining the wire length for every data point in the projection by determining either the mean or sum of absolute distance of the statistical measure of the projections of different channels from their adjacent channels;
2. storing the wire length data in at least one computer data object; and
3. re-ordering the stored projections to minimize a value of wither the mean or sum of the wire lengths across the projections, across each 4 second window, and across all individuals within the plurality of individuals.

In some embodiments, the statistical value for the reordering is selected from the group consisting of: the mean of the sum of the absolute differences of the wavelet packet atoms, and a mean of the sum of (1−correlation) of the wavelet packet atoms.

Obtaining the pre-determined set of normalization factors: In some embodiments, the set of pre-determined set of normalization factors is obtained by determining the mean and standard deviation of the values of the stored projections.

In some embodiments, the brain activity is represented by the energy of the individual BAF. In some embodiments, the energy is determined based on the variance of the signal. In some embodiments, the energy is the maximal value of the energy of the individual BAF. In some embodiments, the energy is the negative entropy of the energy coefficients of the individual BAF as is Coifman and Wickerhauser.

In some embodiments, the BAFs representation of the subject is used to determine the contribution of each BAF to the total energy of the signal being recorded. For example, the BAFs representation of the subject is used to determine the contribution of each BAF to the total energy of the signal being recorded based, at least in part, on:

1) at least one orthogonal condition utilized for the orthogonal decomposition and/or
2) a summation of orthogonal components utilizing the Parseval's equality which holds for the BAFs representation.

In some embodiments, the BAFs representation of the subject is used to obtain the contribution of each BAF to the total length of a virtual wire that is created from obtaining a wire segmentation of the peaks of BAFs; where the virtual wire identifies at least one communication passage being utilized by isolated brain subsystems of the subject to communicate with each other. In some embodiments, the contribution of each BAF to the total length of the virtual wire measures the smoothness of the brain activity in a different, geographically close BAF.

In some embodiments, the contribution of each BAF to the total energy of the signal and the contribution of each BAF to the total length of each virtual wire that is created from obtaining a wire segmentation of the peaks of BAF activity is used to determine which BAF is being presented in the final BAFs representation. In some embodiments, specific BAFs, which are presented in the BAFs representation of the subject, are those BAFs whose contribution to the variance is suitably high and if their contribution to the total virtual wire length is low.

In some embodiments, the present invention provides a system that is capable of an underlying mental state, an underlying neurological condition, or a combination of an underlying mental state and an underlying neurological condition, in the particular individual. In some embodiments, therefore, the system may be used by a physician.

In some embodiments, the apparatus used to record the electrical activity of the brain of a subject may be worn continuously, and is non-invasive, or unobtrusive. Thus, in some embodiments, the identification of the neurological impairment, or determination of the subject's first mental state may be achieved at an earlier time, or may be achieved more efficiently than other methods, because the subject is monitored in a more natural, or less clinical setting. In some embodiments, the system of the present invention enables an earlier detection, identification, or diagnosis of an individual's mental state and/or neurological condition.

In some embodiments, the present invention provides a specifically programmed computer system including:
a. at least one specialized computer machine comprising:
i. a non-transient memory, electronically storing particular computer executable program code; and
ii. at least one computer processor which, when executing the particular program code, becomes a specifically programmed computer processor configured to perform at least the following operations:

1. obtaining, in real-time, by a specifically programmed processor, electrical signal data representative of brain activity of a particular individual;
2. processing, in real-time the electrical signal data representative of brain activity of a particular individual based upon an individual pre-determined predictor associated with a particular brain state, selected from a library of predictors containing a plurality of pre-determined predictors, wherein each individual pre-determined predictor is associated with a unique brain state,
wherein the pre-determined predictor associated with a particular brain state comprises:
i. a pre-determined mother wavelet,
ii. a pre-determined representative set of wavelet packet atoms,
iii. a pre-determined ordering of wavelet packet atoms, created from the pre-determined mother wavelet, and
iv. a pre-determined set of normalization factors, wherein the processing comprises:
i. causing, by the specifically programmed processor, the electrical signal data to be deconstructed into a plurality of pre-determined deconstructed wavelet packet atoms, utilizing the pre-determined representative set of wavelet packet atoms,
wherein time windows of the electrical signal data are projected onto the pre-determined representative set of wavelet packet atoms
wherein the projection is via convolution or inner product, and
wherein each pre-determined representative wavelet packet atom corresponds to a particular pre-determined brain activity feature from a library of a plurality of pre-determined brain activity features;
ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and
3. outputting, a visual indication of at least one personalized mental state of the particular individual, at least one personalized neurological condition of the particular individual, or both, based on the processing,
wherein an individual pre-determined predictor associated with a particular brain state within the plurality of pre-determined predictors is generated by the steps consisting of:
ii. obtaining the pre-determined representative set of wavelet packet atoms by:
1. obtaining from a plurality of individuals, by the specifically programmed processor, at least one plurality of electrical signal data representative of a brain activity of a particular brain state;
2. selecting a mother wavelet from a plurality of mother wavelets,
wherein mother wavelet is selected from an wavelet family selected from the group consisting of: Haar, Coiflet Daubehies, and Mayer wavelet families;
3. causing, by the specifically programmed processor, the at least one plurality electrical signal data to be deconstructed into a plurality of wavelet packet atoms, using the selected mother wavelet;
4. storing the plurality of wavelet packet atoms in at least one computer data object;
5. determining, an optimal set of wavelet packet atoms using the pre-determined mother wavelet, and storing the optimal set of wavelet packet atoms in at least one computer data object,
wherein the determining is via utilizing a Best Basis algorithm; and
6. applying, by the specifically programmed processor, wavelet denoising to the number of wavelet packet atoms in the optimal set;
ii. obtaining the pre-determined ordering of wavelet packet atoms by:
1. projecting, by the specifically programmed processor, the at least one plurality of electrical signal data representative of a brain activity for each 4 second window of the data onto the pre-determined representative set of wavelet packet atoms;
2. storing the projections in at least one computer data object;
3. determining, by the specifically programmed processor, the wire length for every data point in the projection by determining the mean absolute distance of the statistical measure of the projections of different channels from their adjacent channels;
4. storing the wire length data in at least one computer data object; and
5. re-ordering the stored projections, by the specifically programmed computer to minimize a statistical value of the wire length value across each time window, and across all individuals within the plurality of individuals, and across the projections; and
iii. obtaining the pre-determined set of normalization factors by:
1. determining, by the specifically programmed computer, the mean and standard deviation of the values of the stored projections.

In one embodiment, the specifically programmed computer system further includes:
a. at least one specialized computer machine including:
i. a non-transient memory, electronically storing particular computer executable program code; and
ii. at least one computer processor which, when executing the particular program code, becomes a specifically programmed computer processor configured to perform at least the following operations:
1. obtaining, in real-time, by a specifically programmed processor, data representative of (i) at least one physiological parameter of the individual, selected from the group consisting of: heart rate, blood oxygen and/or carbon dioxide levels, body temperature, respiration rate, skin temperature, skin conductivity, and movement, and (ii) at least one environmental parameter; and
2. determining a relationship between the obtained data and the visual indication of at least one personalized mental state of the particular individual, at least one personalized neurological condition of the particular individual, or both.

Methods of Inducing Changes in the Mental State, the Neurological Condition, or Both, in a Subject In some embodiments, the present invention provides a system, comprising:
a. an apparatus configured to apply at least one stimulus to a subject;
b. an apparatus configured to record the electrical activity of the subject's brain and determine the mental state, neurological condition, or both, of the subject, and to record the response the subject has to the at least one stimulus.

In some embodiments, the system further comprises a neural feedback mechanism that is configured to:
a. determine the stimulus that the subject is capable of responding to;
b. alter the nature, magnitude, or duration of the response; or
c. both a and b.

In some embodiments, the response may be a cognitive response. Alternatively, in some embodiments, the response may be an emotional response.

In some embodiments, the system is portable. In some embodiments, the system is configured to provide a real-time interpretation of the activity of the subject's brain.

In some embodiments, the at least one stimulus is selected from the group consisting of: an auditory stimulus, a tactile stimulus, an olfactory stimulus, a visual stimulus, or any combination thereof. Any device configured to provide a stimulus may be used. Examples include, but are not limited to, a speaker, a toy, a game, a projector, a computer screen, and the like.

In some embodiments, the device configured to provide the at least one stimulus is operated remotely from the subject.

In some embodiments, the subject may be monitored remotely, such as, for example, by a caregiver, or a family member.

For example, by way of illustration, the device configured to provide a stimulus may be a bi-directionally operated toy, wherein the toy is configured to attract the attention of an infant. The toy may be manipulated remotely (such as, for example, via Bluetooth), to move and/or change colors. The colors may represent the emotional state of the infant and the movement may represent specific cognitive or emotional state change.

In some embodiments, the device configured to provide the at least one stimulus is the interactive toy disclosed in U.S. Pat. No. 6,773,344.

In some embodiments, the system is further configured to monitor and record the subject's response to the at least one stimulus over time, and determine if the response to the at least one stimulus changes over time. In some embodiments, the system is configured to issue an alert if the response to the at least one stimulus changes.

In some embodiments, the subject is an infant. Without intending to be limited to any particular theory, in the first few months of a child's development there are several key brain developments, which influence the child for life. These developments include, for example, but are not limited to:

1. Development of motor and other cortical activity, such as, for example, catching an object by closing the first, eye movement control and two hands coordination;
2. Development of sensory perception;
3. The co-processing of sensor inputs, such as, for example, visually seeing a word spoken, and hearing the word spoken;
4. Development of decision abilities, such as, for example which toy to look at, which toy to catch, and the like; and/or
5. Development of speech and sound preprocessing.

The developments listed above can be influenced by a variety of factors, including, for example, the subject's health, the environment, nutrition, familial interaction, enrichment, play, stimulation, sleep, neurological disorders, and the like.

By way of illustration, if an infant is not exposed to faces at an early age (or is deliberately not looking at faces), the facial expression analysis will not develop and consequently, the infant may lose to a certain degree the ability to understand facial expressions, one of the key tools of social communication, this can later affect social skills in general, as the developing infant and later child, will not be looking at the face of the other person during social interaction, causing social stress to the second person and consequently reducing social interaction.

Additionally, if the infant is not watching people uttering phonemes and then words during the development of speech recognition and production, the infant's ability to produce accurate sounds may be affected, to a point where the utterance is illegible.

The earlier the detection of a change in the developmental path the easier it is to bring back the development onto the right path with minimal or no damage.

Without intending to be limited to any particular theory, the methods and systems according to some embodiments of the present invention are able to (i) detect abnormalities in the development of an infant, by obtaining a visual representation of the mental state of the infant, which is then used to identify an underlying mental state, an underlying neurological condition, or a combination of an underlying mental state and an underlying neurological condition in the infant; (ii) apply stimuli to the infant, using a stimulating apparatus which creates different stimuli attempting to detect the infant's attention and sustained attention to each stimulus, and the response time to each stimulus; (iii) obtaining a visual representation of the mental state of the infant following the stimuli, which is then used to quantify the infant's response to the stimuli, and (iv) a neural feedback mechanism, which is used to treat the abnormalities in the development of an infant.

In some embodiments, the infant may be rewarded, or encouraged to elicit an improved, or normal developmental task.

In some embodiments, an infant is attached to an EEG monitor while auditory stimulation is played in the background. The infant is free to move around and play with toys. A certain tonal music is being repeated between other pieces of music. The EEG data recording and processing system is controlling the music stimulation as well (from the cloud) by streaming the music to the music player. The specific pattern of response to the specific music piece is collected and analyzed together. This enables to detect whether there are similarities in the response pattern of the BAF (described in detail in main technology patent).

In some embodiments, as the different BAF channels are ordered based on their correlation (on a large data set of recordings), similarity of sub parts (different small groups of consecutive BAF channels) from the full BAF vector is sought. By performing clustering of a certain collection of BAF channels across the entire recording, it is possible to determine whether responses to the music actually form or are a part of the same cluster. Furthermore, it is possible to determine whether the early response is different than response to the same music piece after few repetitions, indicating potential familiarity or habituation to the specific music piece. By performing the same analysis many times and on different pieces of music, it becomes possible to determine whether there is a similar pattern of changing response to a music piece that was played several times, whether the response is the same to "complex" music pieces vs. "simple" ones and whether this changes as the infant develops. By repeating the same music piece few hours later or few days later, it is then possible to examine the short and long term memory consolidation abilities of the infant as a function of age, see the degree of complexity of the music pieces to which the infant responds to in a similar manner and determine the babies memory, attention and comparison abilities. Furthermore, by changing one or more notes in the music piece it is possible to determine whether the infant notices the change, by noticing a difference in brain activity response as is measured with the BAFs.

Different complexity of musical and other stimuli can be provided to babies at different ages. Using said inference, one may determine at what age an infant starts responding to the different stimuli and this can be used to quantify infant's development. For example, it is possible to determine whether an infant responds to faces, to familiar faces, to facial expressions, to faces correlated with sounds and so forth.

In some embodiments, the mood of the subject (such as, for example, a developing infant) may be inferred. For example, by way of illustration, in some embodiments, mood is inferred from channels related to stress and happiness in the BAF representation. In some embodiments, channels related to stress are 1-4 negatively correlated and 34-37, 113-114, 119-121 positively correlated. In some embodiment, increased activity in those channels may indicate stress, anxiety or pain suffering. Caregiver intervention may differentiate between these possibilities.

In some embodiments, a mood disorder may be detected. For example, by way of illustration, in some embodiments, channels correlated with positive mood are 34-38 and 113-114 and another set is 119-121. In some embodiments, the first is more related to positive mood as a result of external stimuli, such as seeing a happy movie, while the latter is more related to an inner feeling such as a personal achievement that causes happiness. Lack of activity in these channels may indicate depression.

In some embodiments, attention disorder may be correlated with lack of attention to the stimuli, in this case, there will be times where the same stimuli will cause the desired response, for example indication of familiarity with the stimulation, while in others, the infant may be occupied by other distractors and the same stimulus will not produce the same response.

In some embodiments, OCD may be indicated by some repeated brain activity which can be inferred via the said inference mechanism, but may not be found to be correlated to external stimuli, but rather to internal brain activity.

In some embodiments, memory consolidation or lack thereof as measured by lack of response to familiar stimuli may be an indication to attention deficiencies or other brain developmental disorders which can be further discerned by a developmental expert. Early detection and intervention is key to quickly alleviating the problem.

In some embodiments, response to familiar faces or to facial expression or lack thereof may be an indication of a behavior that is on the autistic spectrum.

In some embodiments, the setup of producing different stimuli can be used to enhance and improve brain development. This can be achieved by providing more often stimuli that the infant seems to have difficulty in recognizing, thus developing the infant's ability to analyze and recognize such stimuli. Also positive reinforcement (by words, sound, or color) can increase infant's attention span and motivate the infant to be attentive and respond.

In some embodiments, the system provides cognitive and emotional stimulation and feedback. In some embodiments, the system provides statistics to caregivers about the brain states of the subject (such as, for example, the percentage of time the subject is focused, happy, stressed, conscious, etc.). In some embodiments, the system provides a tool to teach a child to control his different emotions, and different cognitive actions.

In some embodiments, the system is further configured to assess the subject's cognitive, development abilities, or both. For example, in the case where the subject is an infant, the system is configured to monitor the development of the subject, and determine when, and if the infant achieves certain developmental milestones.

In another example, where the subject is an individual in a minimal conscious state, the system is configured to monitor the brain activity of the subject and determine if the subject reaches a higher level of consciousness.

In some embodiments, the system is configured to monitor and encourage the creation of healthy habits (such as, but not limited to sleeping, playing, and eating). By way of illustration the system can monitor times when the subject is asleep, or the quality of sleep, sleep depth, the time taken to fall asleep, the time taken to wake up, or any combination thereof. The system utilizes the recorded parameters, and can provide the subject (e.g. an infant) with auditory feedback that encourage relaxation, and accelerate sleep. In additional embodiments, during sleep, the music can be changed to enable deeper and better relaxation.

In some embodiments, the system can monitor stress and relaxation levels. In some embodiments, the system can issue an alert when the subject (e.g. an infant) feels uncomfortable or stressed, and provides self-adjusted relaxing sounds, vibrates or displayed pictures and lights.

In some embodiments, the system monitors self-quieting activities by an infant, or, how frequently, or quickly the infant is capable of calming itself, and assisting the infant in the relaxation process by playing self-adjusted relaxing sounds, vibrations or displaying pictures and lights.

In some embodiments, the system is configured to monitor a subject's (e.g. an infant's) learning capacities, or the ability of the subject to learn new categories. In some embodiments, the system produces rows of stimuli that relate in the same category, and attach to the row a single stimuli from an unrelated category (possible category types: musical stimuli from the same category, semantical stimuli from the same category, subject related categories such colors, animals, words and numbers, or any other type of category). The system analyzes the subject's reaction to the unrelated stimulus by measuring attention levels, reaction time and the number of times stimulus should be presented in order to facilitate learning of the category. The system provides a reward if the subject succeeds to discriminate the unrelated stimulus. The category may become more and more complex as the subject demonstrates the ability discriminate simple differences.

For example, the system may monitor an infant's reaction toward human vs. non-human sounds. In some embodiments, the system produces sounds of human singing and humming, and the sounds of its correlated tonal melodies. The system analyzes the levels of excitement and attention. If the infant not prefer human voice the system binds the human singing and humming sounds to more engaging stimuli, that is self-adjusted to the individual infants preference—for example—flickering light that are presented on a display.

In another example, the system may monitor reaction toward social stimuli, such as, for example, the infant's own name, faces, or laughter. In some embodiments, the system produces the infant's name by both the caregiver voice and a stranger's voice. The system analyzes the levels of excitement and the infant's reaction time. If the infant does not react, the system binds the name to more engaging stimuli, that is self-adjusted to the individual infants preference—for example—flickering light that are presented on a display.

In another example, the system can monitor learning capacities, such as, for example, response toward a familiar stimulation vs. unfamiliar, or the ability to inhibit and dis-inhibit information. In some embodiments, the system produces a long and persistent stimulus that changes after amount of time. The system analyzes the infant's reaction times, attention levels, and the ability to inhibit and dis-inhibit the stimulus. If the infant fails to inhibit the stimulus it would fade out gradually, and the process will repeat itself. If the infant fails to dis inhibit it a new stimulus will be performed and for a shorter duration.

In some embodiments, the system can monitor the learning of language prosody. In some embodiments, the system produces sounds with different acoustic intonation that can differ in pitch, height, range/variability and melodic contour. The system analyzes the infant's duration to react, level of attention, and time to disengage. If the infant reaction is slow, or not attentive to the sounds the system will provide more instance intonation.

Figure 18:
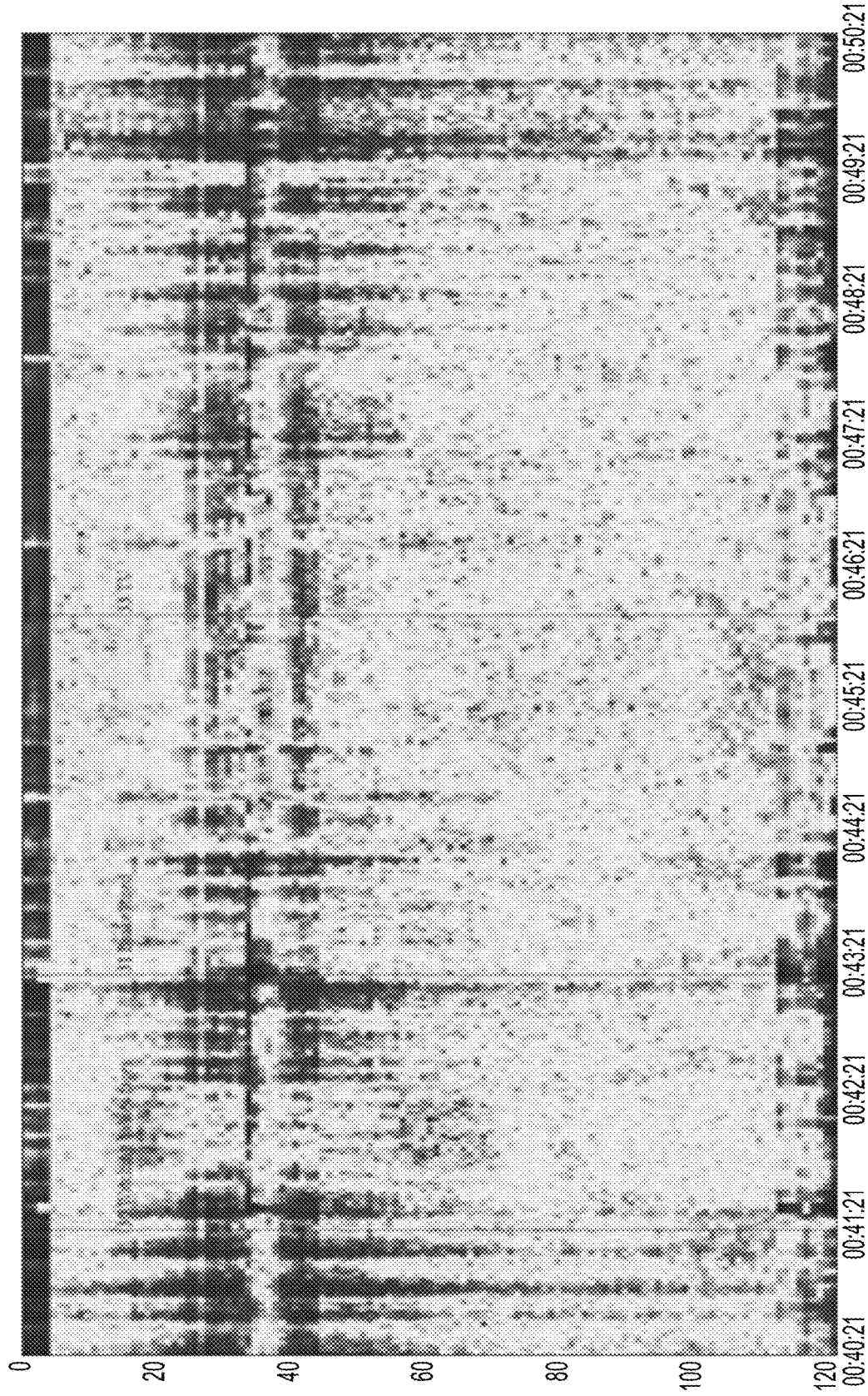
FIG. 18 shows a screenshot of an example of a brain activity features (BAFs) representation of an infant responding to different musical stimuli.

Referring to FIG. 18, in some embodiments, the system can monitor musical discrimination. In some embodiments, the system produce sounds of differentiate musical instruments and timbers, play it in pairs that constructed due to their acoustic differences. The system analyzes the subject's discrimination capability and reaction to the change, and if the subject is able to discriminate between the pair of stimuli, the subject gets a feedback in the shape of self-adjusted musical reward. The set of stimuli can differ more and more as the subject is capable of discriminating more complicated differences.

In some embodiments, the system can monitor learning capacities; quality of engagement with a complex stimuli as a function of its complexity. In some embodiments, the system produces both simple and complex musical and visual stimuli, and analyze the infant's changes in excitement and attention levels, the duration to engage with each stimulus, and the number of times each complex stimulus should be presented until it became trivial to the infant. The system can provide more and more complex stimuli, until the infant will no longer be attentive. Rows of stimuli can start with more complex once as the infant sharpen his discrimination skills.

In some embodiments, the system is employed in a method comprising:
a. recording electrical or magnetic brain activity using at least one modality such as EEG, MEG, or depth electrodes;
b. obtaining Brain Activity Features (BAF) in an unsupervised or semi-supervised manner. This relies on finding useful signal decompositions using decomposition methods like harmonic analysis, which are more refined methods to principal or independent components analysis.
c. obtaining a predictor for a specific brain state using a machine learning algorithm from the given set of observations as represented by the said BAF.
d. the predictor can then be found from the clustered brain states using machine learning algorithms.
e. from the clusters of step 3, it is possible to obtain temporal dependency between cluster memberships, so that each cluster can be labeled by a letter. Then, "words" which are composed of these letters can be obtained, and segmentation as well as text analysis techniques can be applied to the new collection of letters.

In some embodiments, step 3 can be replaced by a clustering which reduces the dimensionality of the BAF into a number of brain states.

In some embodiments, the present invention provides a method, wherein the method induces a change in the mental state, neurological condition, or both, of a subject from a first mental state, first neurological condition, or both, to a second mental state, a second neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. comparing the first visual indication of a first mental state, first neurological condition, or both, of the subject to the second visual indication of a second mental state, second neurological condition, or both, of the subject;
d. based on the comparison, determining if the second mental state, second neurological condition, or both, of the subject is different from the first mental state first neurological condition, or both, and, if the second mental state, second neurological condition, or both, of the subject is not different from the first mental state, first neurological condition, or both;
e. iteratively
 i. applying at least one subsequent stimulus to the subject,
  wherein each at least one subsequent stimulus is different from the preceding at least one stimulus;
 ii. obtaining a subsequent visual indication of a mental state, neurological condition, or both of the subject;
 iii. comparing the first visual indication of a first mental state, first neurological condition, or both, of the subject to the subsequent visual indication of a mental state, neurological condition, or both, of the subject;
 iv. based on the comparison, determining if the mental state, neurological condition, or both of the subject is different from the first mental state, first neurological condition, or both,
  wherein steps i to iv are performed until the mental state, neurological condition, or both, is different from the first mental state, first neurological condition, or both.

In some embodiments, the present invention provides a method, wherein the method induces a change in the mental state, neurological condition, or both of a subject from a first mental state, first neurological condition, or both, to a desired mental state, desired neurological condition, or both, the method comprising:
a. obtaining a first visual indication of a first mental state, first neurological condition, or both, of a subject;
b. applying at least one first stimulus to the subject and obtaining a second visual indication of a second mental state, second neurological condition, or both, of the subject;
c. determining if the second visual indication of a second mental state, second neurological condition, or both, of the subject is indicative of the desired mental state, second neurological condition, or both, and if not;
d. iteratively,
 i. applying at least one subsequent stimulus to the subject,
  wherein each at least one subsequent stimulus is different from the preceding at least one stimulus;
 ii. obtaining a subsequent visual indication of a mental state, neurological condition, or both, of the subject;
 iii. determining if the subsequent visual indication of the mental state, neurological condition, or both, of the subject is indicative of the desired mental state, desired neurological condition, or both,
  wherein steps i to iii are performed until the desired mental state, desired neurological condition, or both, is obtained.

In some embodiments, the present invention provides a method, wherein the method induces a change in the mental state, neurological condition, or both, of a subject from a first mental state, first neurological condition, or both, to a desired mental state, desired neurological condition, or both, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and if not;
d. iteratively,
 i. comparing the first visual indication of a first mental state, first neurological condition, or both of the subject to the second visual indication of a second mental state, second neurological condition, or both of the subject;
 ii. based on the comparison, selecting a subsequent stimulus and applying the selected subsequent stimulus to the subject,
  wherein each at least one subsequent selected stimulus is different from the preceding at least one stimulus;
 iii. obtaining a subsequent visual indication of a mental state, neurological condition, or both of the subject;
 iv. determining if the subsequent visual indication of the mental state, neurological condition, or both of the subject is indicative of the desired mental state, desired neurological condition, or both,
wherein steps i to iv are performed until the desired mental state, desired neurological condition, or both, is obtained.

In some embodiments, the present invention provides a method, wherein the method provides a reward if a subject elicits a desired mental state, desired neurological condition, or both, in response to an at least one first stimulus, the method comprising:
a. obtaining a first visual indication of a first mental state, first neurological condition, or both of a subject;
b. applying at least one first stimulus to the subject and obtaining a second visual indication of a second mental state, second neurological condition, or both of the subject;
c. determining if the second visual indication of a second mental state, second neurological condition, or both of the subject is indicative of the desired mental state, desired neurological condition, or both, and providing a reward;
d. if, however, the second visual indication of a second mental state, second neurological condition, or both of the subject is not indicative of the desired mental state, desired neurological condition, or both;
e. iteratively,
  i. comparing the first visual indication of a first mental state, first neurological condition, or both of the subject to the second visual indication of a second mental state, second neurological condition, or both of the subject;
  ii. based on the comparison, selecting a subsequent stimulus and applying the selected subsequent stimulus to the subject,
     wherein each at least one subsequent selected stimulus is different from the preceding at least one stimulus;
  iii. obtaining a subsequent visual indication of a mental state, neurological condition, or both of the subject;
  iv. determining if the subsequent visual indication of the mental state, neurological condition, or both of the subject is indicative of the desired mental state, desired neurological condition, or both,
     wherein steps i to iv are performed until the desired mental state, desired neurological condition, or both, is obtained.

In some embodiments, the present invention provides a method, wherein the method identifies a stimulus that a subject is capable of responding to, the method comprising:
a. obtaining a first visual indication of a first mental state, a first neurological condition, or both, of a subject;
b. applying at least one first stimulus to the subject and obtaining a second visual indication of a second mental state, a second neurological condition, or both, of the subject;
c. comparing the first visual indication of the first mental state, the first neurological condition, or both, of the subject to the second visual indication of a second mental state, second neurological condition, or both, of the subject;
d. based on the comparison, determining
  i. if the second mental state, second neurological condition, or both, of the subject is different from the first mental state, the first neurological condition, or both, and, if the second mental state, the second neurological condition, or both, of the subject is different from the first mental state, first neurological condition, or both,
  ii. determining if the difference between the second mental state, the second neurological condition, or both, and the first mental state, the first neurological condition, or both, is a coherent response to the at least one first stimulus;
and if the difference between the second mental state, the second neurological condition, or both, and the first mental state, the first neurological condition, or both, is not a coherent response to the at least one first stimulus;
e. iteratively
  i. applying at least one subsequent stimulus to the subject, wherein each at least one subsequent stimulus is different from the preceding at least one stimulus;
  ii. obtaining a subsequent visual indication of a mental state, neurological condition, or both of the subject;
  iii. comparing the first visual indication of the first mental state, the first neurological condition, or both, of the subject to the subsequent visual indication of a mental state, neurological condition, or both, of the subject;
  iv. based on the comparison, determining if the subsequent mental state, neurological condition, or both of the subject is
    1. different from the first mental state, the first neurological condition, or both, and
    2. the difference between the second mental state, the second neurological condition, or both, and the first mental state first neurological condition, or both, is a coherent response to the at least one first stimulus,
     wherein steps i to iv are performed until the subsequent mental state, the neurological condition, or both, of the subject is different from the first mental state, first neurological condition, or both, and the difference between the second mental state, the second neurological condition, or both, and the first mental state, the first neurological condition, or both, is a coherent response to the at least one first stimulus.

In some embodiments, a temporal structure probabilistic model is applied to the BAF's to determine the correlation between the at least one stimulus applied and the observed brain activity. In some embodiments, a strong correlation indicates a coherent response to the at least one stimulus.

In some embodiments, the degree of response ("RtS") is used to identify the at least one stimulus that the subject is capable of responding to.

In some embodiments, the method further comprises the step of issuing an alert if the at least one first stimulus causes a change in the subject's mental state, neurological condition, or both.

In some embodiments, the method further comprises the step of issuing an alert if the at least one second stimulus causes a change in the subject's mental state, neurological condition, or both.

In some embodiments, the at least one first stimulus is selected from the group consisting of: an auditory stimulus, a tactile stimulus, an olfactory stimulus, a visual stimulus, or any combination thereof.

In some embodiments, the at least one subsequent stimulus is selected from the group consisting of: an auditory stimulus, a tactile stimulus, an olfactory stimulus, a visual stimulus, or any combination thereof.

In some embodiments, the at least one subsequent stimulus is different from the at least one first stimulus.

In some embodiments, the methods and systems according to some embodiments of the present invention are able to identify stimuli that a subject that is in a minimally conscious state (MCS) can respond to.

In some embodiments, RtS can indicate the type of stimuli that a person that is in a Minimal Conscious State (MCS) responds to. For example, it can help determine whether the person responds in a consistent way to visual stimuli, auditory stimuli, other sensory stimuli, commands, and the like.

In some embodiments, the identification of stimuli that the subject can respond to can optimize medical intervention that aims to increase response to various stimuli. In the case of a subject in MCS, for example, a physician, or care giver, can look at the entropy of the alphabet and produce a single number which determines the total entropy of the alphabet (just based on letters or also based on more sophisticated grammatical rules that are inferred and length of words that are inferred.

In one specific embodiment, the said alphabet can be used to create music. In some embodiments, the music can enable a MCS subject to produce some means of communication and to obtain neural feedback on the subject's brain activity.

In some embodiments, different letters can produce different musical notes with different musical instruments or can be used to change tempo and other musical parameters. The result would be a melody that is produced from an MCS subject's brain and can provide a means of communication. For example, by way of illustration, an MCS subject may learn to operate external devices once a control on the production of these letters is achieved.

In some embodiments, using the musical feedback, subjects can be trained to produce the desired response.

In some embodiment, the group of channels 34-38 in BAF's which have been found to be missing in MCS can be used as a neural feedback to encourage MCS subjects to increase the activity of these channels.

Referring to FIG. 19, showing a screenshot of an example of a brain activity features (BAFs) representation of a minimally conscious subject, obtained over 4 days, where the medications administered to the patient were changed. The recordings are reordered based on channels 34-38. These channels appear to be more active for conscious subjects than for minimal conscious subjects. It is evident that on the first day (top) and the third day (third from top) those channels were more active than on the other days. The summary statistics at the bottom provides such information. The first numbers indicate the total time of recording on that day. The second number Exec indicates the percent of activity of said channels. On the first day, the Exec value was 51% and in the third day is was 38%, and in other days it was much less (17% and 9%.) Other channels related to cognitive activity are SupCog and SemCog, Emo relates to emotional activity, slp relates to sleep-like activity and strs indicates potential pain.

Figure 20:
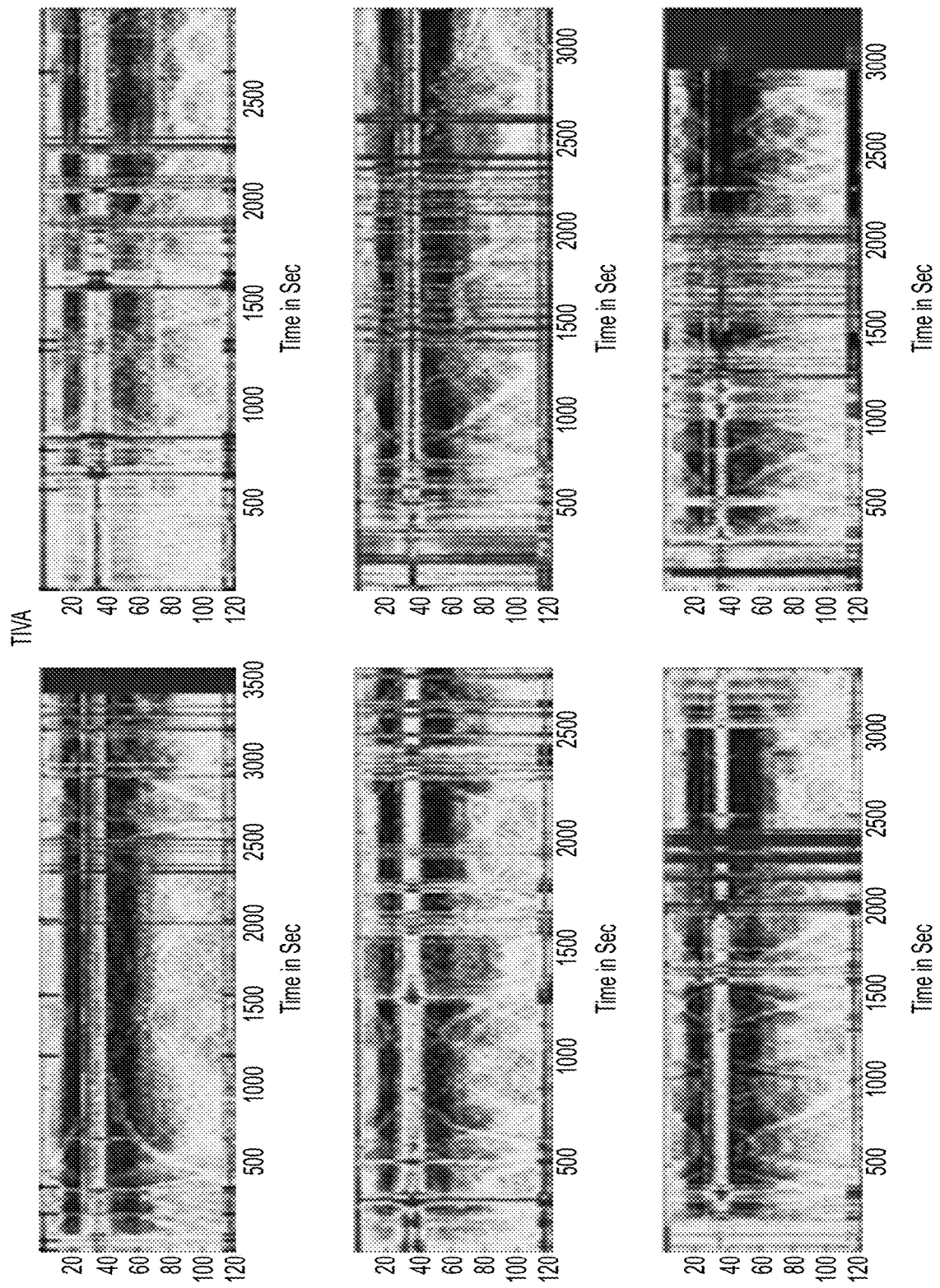
FIG. 20 shows a screenshot of an example of a brain activity features (BAFs) representation of a subject rendered unconscious by total IV anesthesia.
Figure 21:
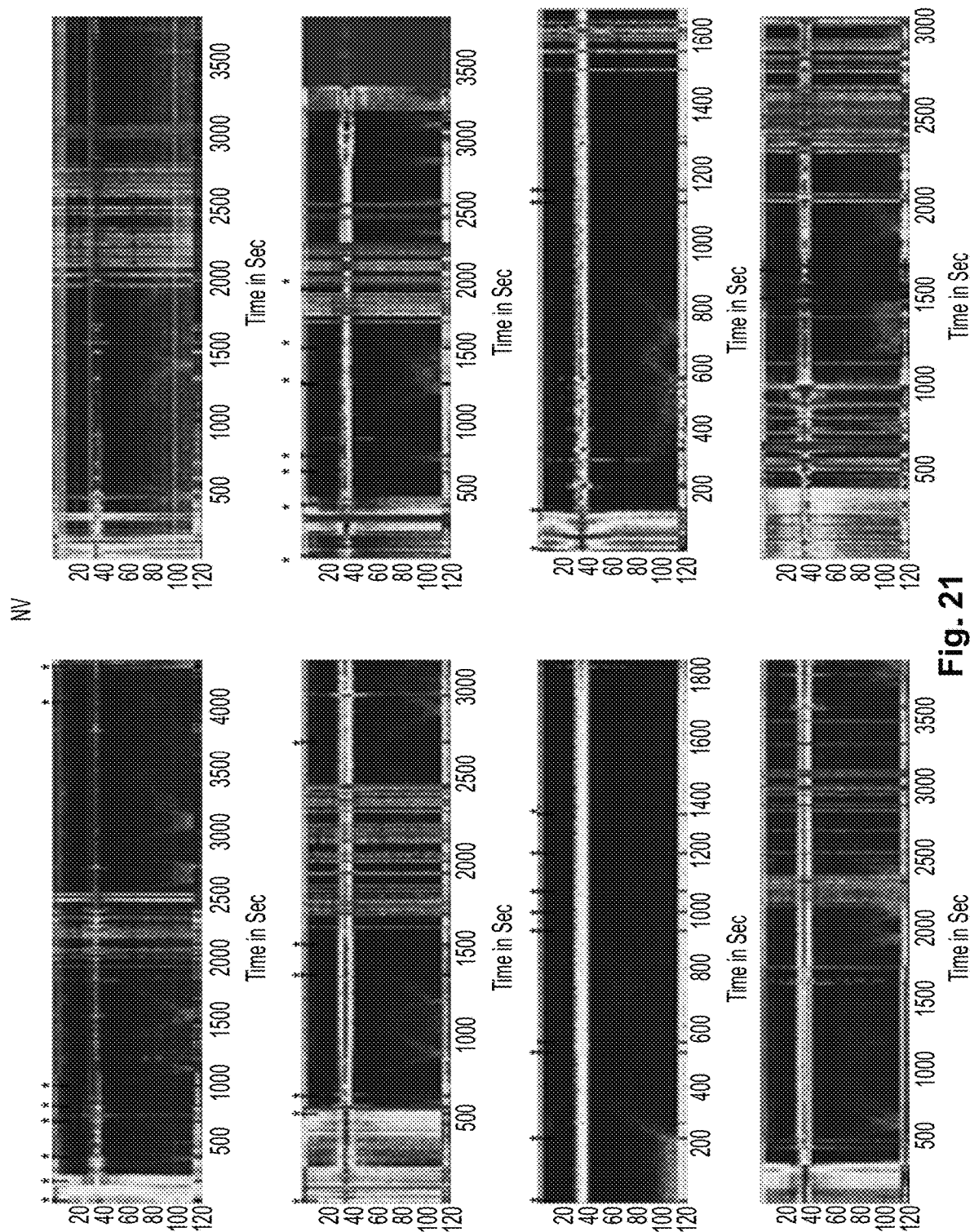
FIG. 21 shows a screenshot of an example of a brain activity features (BAFs) representation of a subject rendered unconscious by inhalant anesthetic.

Referring to FIGS. 20 and 21, showing a screenshot of an example of a subject rendered unconscious by total IV anesthesia (TIVA—FIG. 20), or inhalant anesthetic (NV—FIG. 21), a marked reduction in bran activity is observed in subjects rendered unconscious by inhalant anesthetic, compared to total IV anesthesia. The reduced brain activity may be a factor associated with increased complications resulting from the use of inhalant anesthetics.

Reference is now made to the following examples, which together with the above descriptions illustrate some embodiments of the invention in a non-limiting fashion.

ILLUSTRATIVE EXAMPLES IN ACCORDANCE WITH AT LEAST SOME EMBODIMENTS OF THE PRESENT INVENTION

Figure 6:
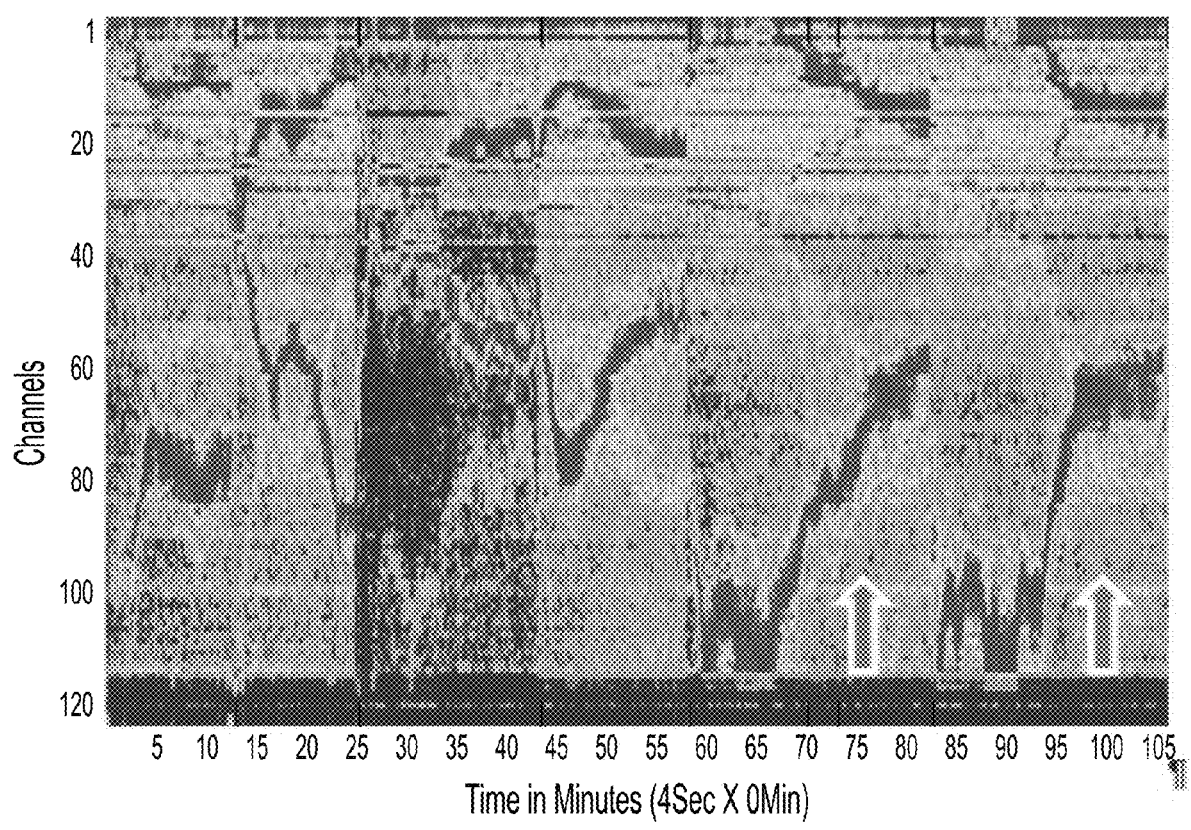
FIG. 6 shows a screenshot of an example of a BAFs representation of a subject according to some embodiments of the present invention.

Example 1: BAF Representations Obtained from Multiple Subjects Performing Specific Cognitive Tasks FIG. 6 shows a BAF representation from 7 subjects. Each raw (Y axis) represents the activity of a single BAF. The color coding is ("hot") indicating that high activity tends towards red and low activity tends towards blue. Each column (X axis) represents a vector of activity at a specific time frame. Thus, the X axis is measured in time (minutes or seconds). FIG. 6 is measured in minutes. The specific figure represents activity of 6 subjects during a cognitive task. Thus, it is possible to concatenate EEG of different recordings together so that one figure (or matrix of BAF) represents activity of different tasks, or different subjects performing (different) tasks. In this specific figure, the arrows indicate two subjects that have a relatively similar pattern of activity during the task. Thus, this figure represents different cognitive strategies performed during the same cognitive task, performed by different subjects.

Figure 7:
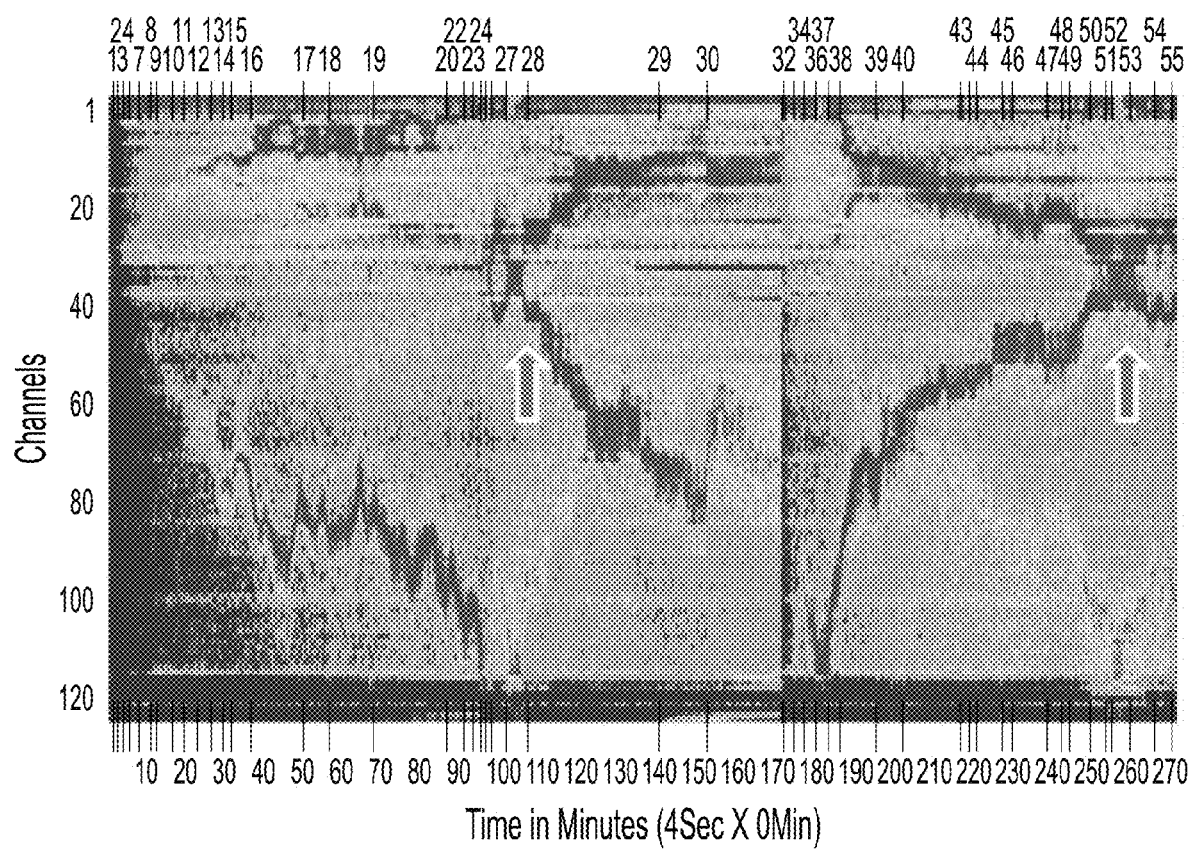
FIG. 7 shows a screenshot of an example of a BAFs representation of a subject according to some embodiments of the present invention.

Example 2: BAF Representations Obtained from a Subject Watching Three Movies that Elicit Different Emotional Responses Brain activity (BAF) during three movies (each recorded at a different time). Referring to FIG. 7, it can be seen that the activity of the second and third movie is more similar in terms of the BAFs that are active, compared with those active in the first movie. The first movie (Derailed) includes violence and horror, while the other two movies (Stolen Life and Skin) are more associated with sadness and warm feelings. The arrows mark the time of strong positive emotional feelings in the two movies. It is evident that the BAFs active at that time are the same. They are also active in FIG. 8 below during meditation.

Figure 8:
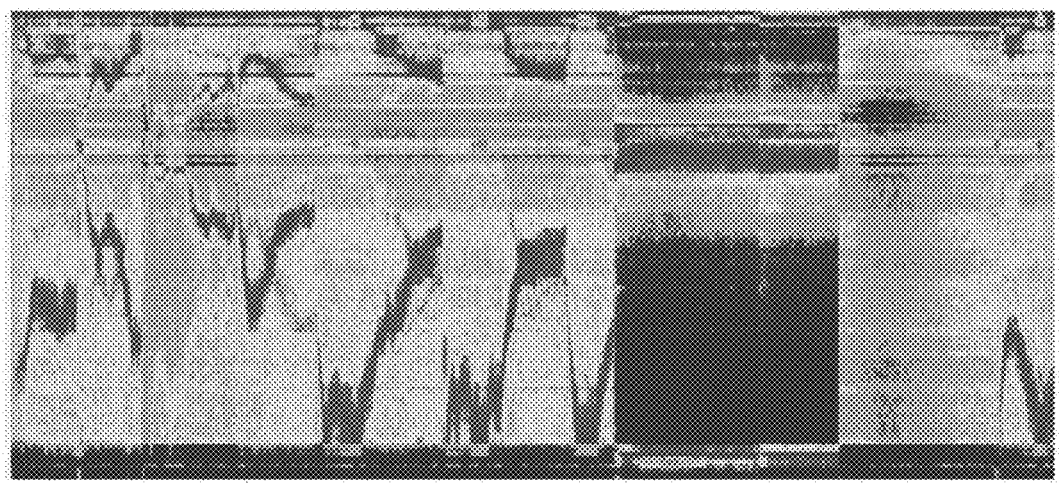
FIG. 8 shows a screenshot of an example of a BAFs representation of a subject according to some embodiments of the present invention.

Example 3: BAF Representations Obtained from Seven Subjects Performing E-Learning Tasks EEG recordings were obtained from 7 subjects, according to some embodiments of the present invention, whilst the subjects were performing specific e-learning tasks. The BAF representations are shown in FIG. 8. The task included information gathering and then answering questions at two levels of difficulty (this was the same representation from FIG. 6). This was followed by two experienced meditators performing Gayatri Meditation and an inexperienced person performing Japa meditation immediately followed by music listening. The active BAFs during the Gayatri meditation were similar to those that are active during the positive emotional parts in the movies (FIG. 7). There is evidence that experienced meditators demonstrate increased co activation of mPFC, insula, and temporal lobes while reducing the activity of the default mode network. There is also evidence of a sense of happiness.

Figure 9:
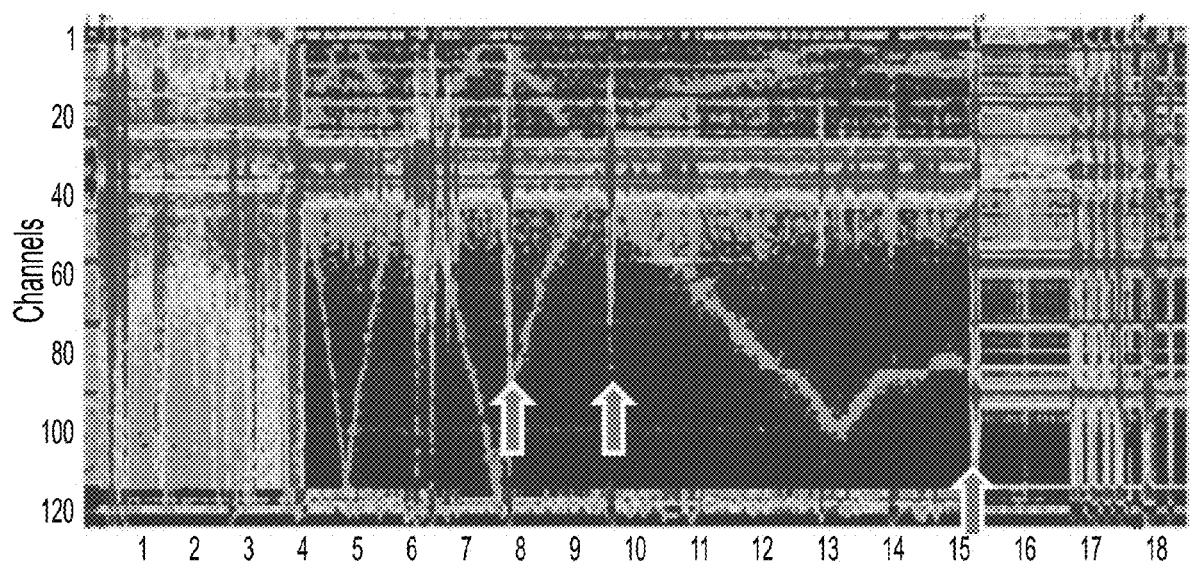
FIG. 9 shows a screenshot of an example of a BAFs representation of a subject according to some embodiments of the present invention.

Example 4: BAF Representations Obtained from Subject Receiving a Painful Stimulus, Before and after Receiving an Anesthetic Referring to FIG. 9, the figure represents the brain activity after receiving anesthesia. The Anesthesia is induced where the picture becomes mainly blue. It is seen that a region of activity (the same region in BAF space that was active during meditation) remains active. This does not happen to all patients. The two arrows (on the left) indicate time when pain is induced during the surgery. It is clear that there is a reactive brain activity to this induced pain. The arrow on the right represents the beginning of use of a laser surgical tool, which creates a large electric noise, thus, the recording from that point is less clear. One observation in this subject is that once the laser knife starts its action (stronger pain) the activity in the region that was active during meditation stops.

Figure 10:
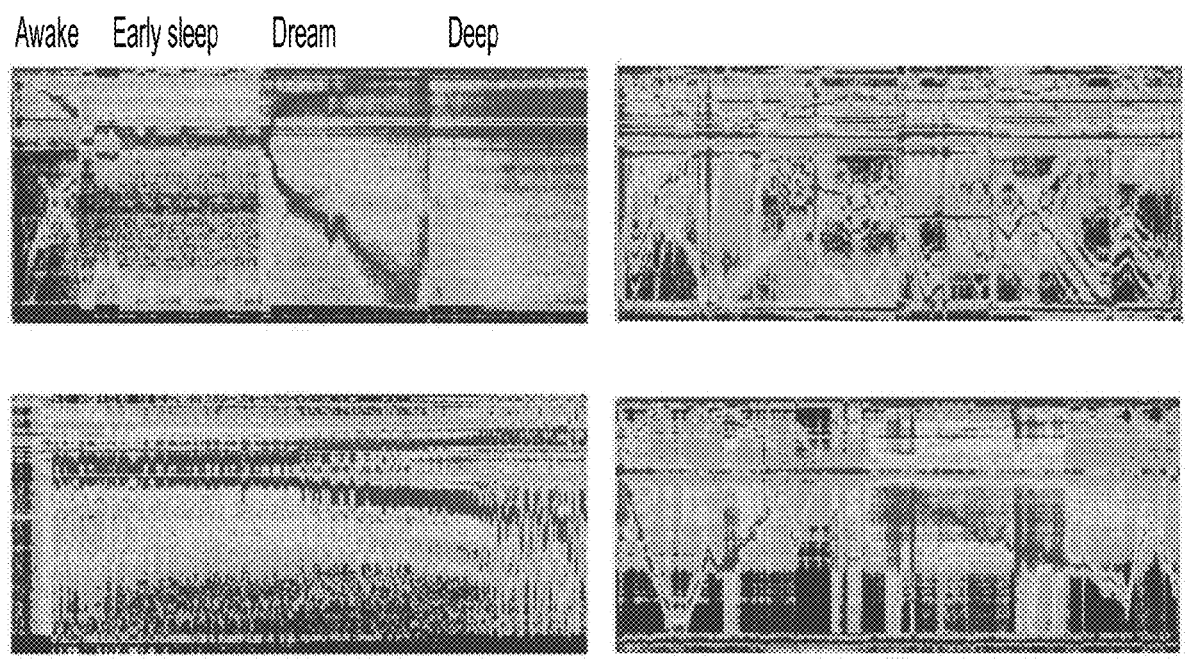
FIG. 10 shows a screenshot of an example of a BAFs representation of a subject according to some embodiments of the present invention.

Example 5: BAF Representations Obtained from Subjects During a Sleep-Wake Cycle Sleep monitoring is crucial for the early detection of physical and mental health problems; diagnosis and treatment of insomnia; and diagnosis and monitoring of dementia. Fatigue monitoring is crucial when the brain is engaged in tasks that require fast thinking and response, especially in roles where alertness is essential to performance and safety (e.g. a pilot). FIG. 10 indicates the amount of information that can be obtained using the said BAF. The upper left panel depicts three sleep stages, in which brain activity is vastly different. The activity was recorded from a single person during a single night's sleep. The bottom left panel concentrates on the early sleep stage, demonstrating a different shift from that stage (which is similar to meditation) into the REM or dream stage. The top right panel demonstrates an intense dream and cognitive activity during sleep, looking very similar to the kind of activity that occurs while being awake, e.g. while watching a movie. The bottom right panel indicates the strength of BAF for fatigue monitoring: it depicts the brain activity of a subject briefly falling asleep while watching a movie. The engagement with the movie is clear even when the subject is partially falling asleep, as the line of strong activity behind the (snow-like noise).

Figure 11:
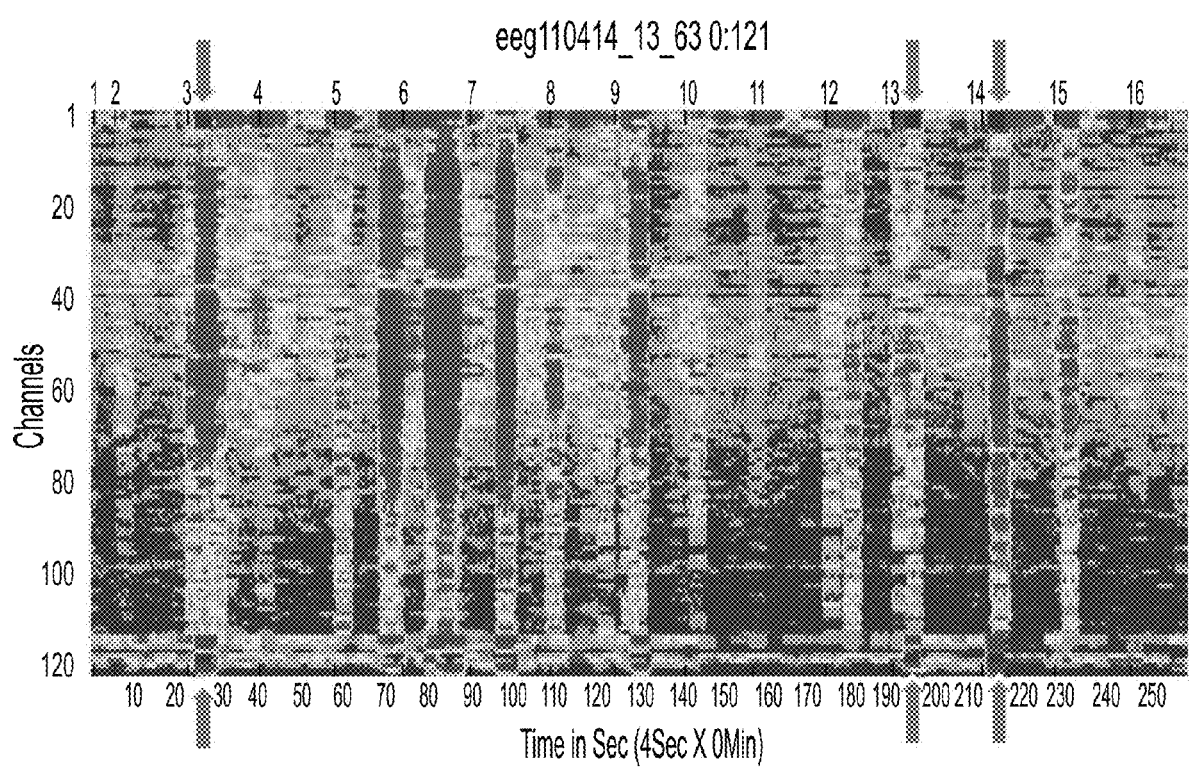
FIG. 11 shows a screenshot of an example of a BAFs representation of a subject according to some embodiments of the present invention.

Example 6: BAF Representations Obtained from Subjects During a Memory Recall Task and Stress Detection The activity depicted in FIG. 11 is typical during a session of questions and answers, or during stimulus identification. The length and strength of the lines is indicative of the amount of cognitive effort. It is also possible to see stress at the regions pointed to by the arrows. The recording was taken during a company interview. The representation indicates questions which required more cognitive load to respond to (memory or concentration) and in particular show questions which elicited stress in the subject.

Such representation can be useful for lie/stress detection and for automatic (machine induced interrogation). It can also be used for massive teaching such as Coursera, where it is important to observe that the subject is concentrated and focused on the questions. The pattern would look different if the subject had the answer on a piece of paper or contacted a friend to obtain the answer.

If detailed BAF representation is specific to a subject, it may possible to determine the identity of the subject from the specific BAFs. This can be used for authentication and identity management as well as for competency monitoring indicating when the subject is capable of performing the required task: is concentrated, not stressed or otherwise emotionally distracted, is not under the influence of drugs or under threat.

Example 7: BAF Representations Obtained from Subjects Having Abnormal Brain Activity Associated with a Seizure The arrows in FIG. 5 indicate a constant activity of a certain BAF which may be indicative of a constant activity of a certain brain network or region. Such constant activity is not normal and appears to be associated with pre-seizure activity. The two bottom arrows indicate the beginning and end of the abnormal activity of a certain BAF. Using such representation it may be possible to better quantify and study the factors and stimulations which increase the likelihood of such abnormal activity and those which reduce it. This can be useful for intervention, either by suggesting a lifestyle change (relaxation, turning light off, consuming sugar, coffee etc., or meditation, exercise and other state change. It can also suggest better disease management via medications.

Referring to FIG. 4A, an experienced yogi is performing three types of meditation (indicated via the horizontal brackets). After the first two meditations and after the third meditation, the yogi explains what he is doing. A range in BAFs is indicated with the vertical brackets. This collection of BAFs is of associated with awareness. It is clear that one meditation emphasizes only these awareness channels, and it is evident in the activity when the yogi explains what meditation he is doing.

Referring to FIG. 4B, a BAFs representation is shown from an individual in a vegetative state. The BAFs highlights in FIG. 4A are shown, and are not active. However, administration of a stimulus to the individual was able to activate the BAFs associated with awareness for a short period of time.

Figure 12:
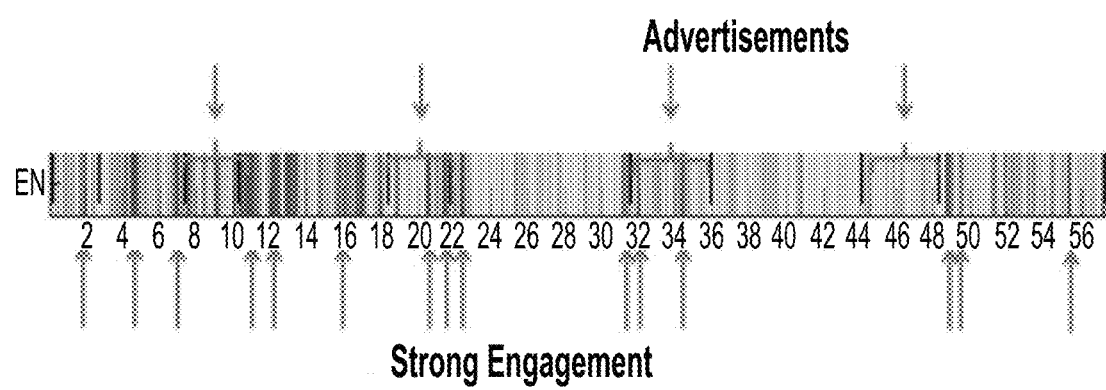
FIG. 12 shows a screenshot of an example of a representation of recording for a brain activity feature of a subject according to some embodiments of the present invention.

Example 8: BAF Representations Obtained from Subjects Observing an Advertisement In FIG. 12, the summary statistics of a large cohort of subjects is shown. Brain activity of the group was recorded while they were exposed to a TV show (57 minutes) which had several commercial breaks marked by the arrows at the top. In a preferred embodiment, the brain activity as interpreted by the said BAFs and was then clustered into eight clusters of brain activity. The vertical colored lines represent the proportion of subjects which happened to be in the same cluster of brain activity in a specific second of the TV show. The values can change every second. The red lines indicate that the majority of subjects were found to be in the same brain activity cluster at that second. This indicates engagement with the show or the advertisements. Using such representation can be useful for determining the more engaging parts of the show and the advertisements. When such recording is done in a distributed manner in many houses of TV viewers, one can obtain a real time engagement score which can then be used for advertising effectiveness and other media explorations.

Figure 13:
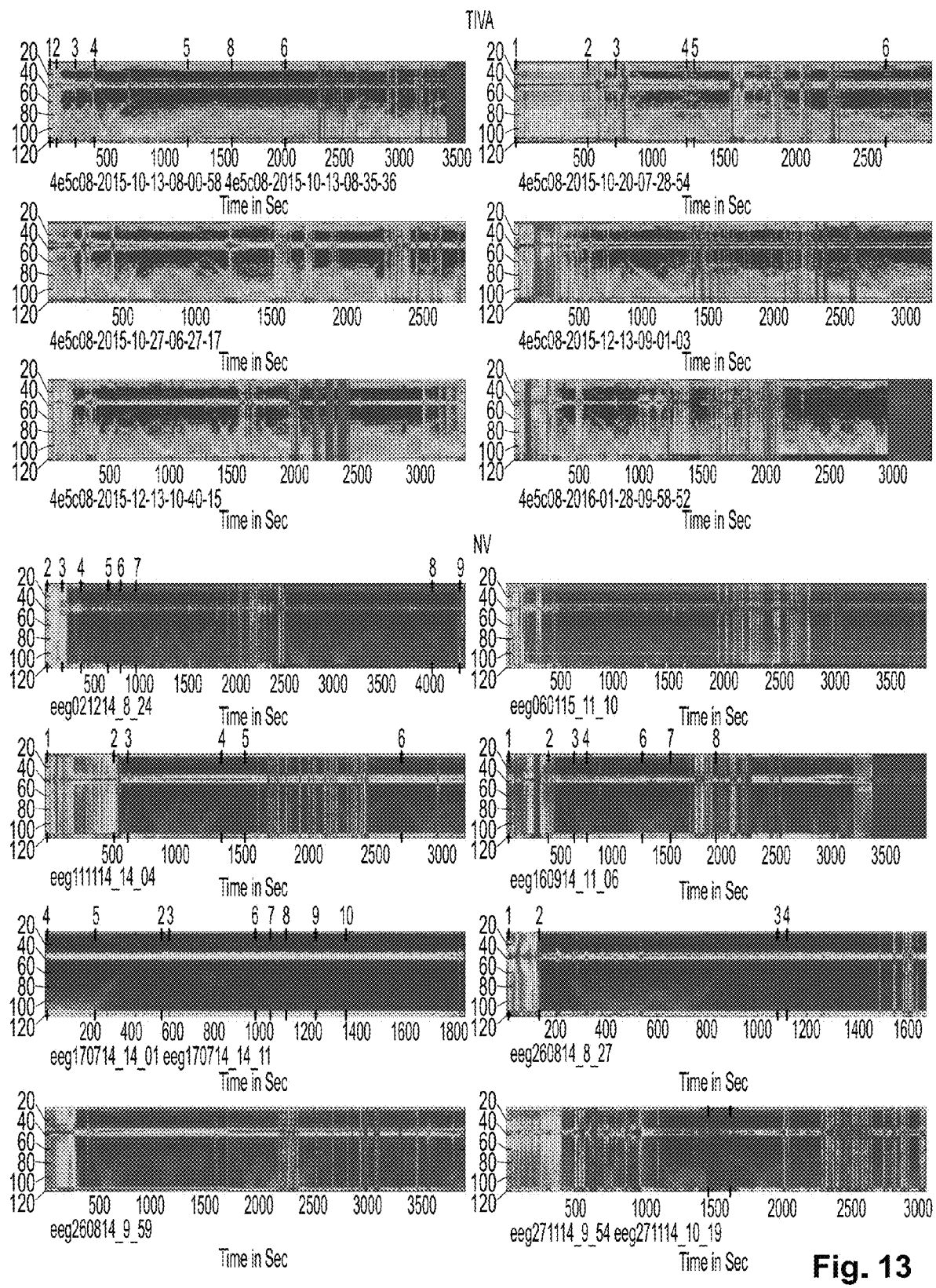
FIG. 13 shows a screenshot of an example of multiple representations of recording for a brain activity feature of a subject according to some embodiments of the present invention.

In FIG. 13, a collection of recordings from two types of anesthesia medications are presented. It is evident that the top 6 recordings represent a very different brain activity as compared to the bottom 8 recordings. This indicates the power of the technique to separate between two anesthesia methods, Total IV vs. Gas.

Example 9: BAF Representations BAFs Obtained in Real Time

FIGS. 3 and 13 illustrate brain activity images constructed based on the real-time processing of the EEG signal based on the full matrix and without the re-scaling. It represents difference in brain activity between two different anesthetic techniques. The first one is called TIVA which is Total IV Anesthesia vs. NV which is inhalation (gas) anesthesia. Both are considered safe and are supposed to provide full anesthesia, however, NV is significantly less costly. The figures demonstrate a strong difference in brain activity between the two anesthesia methods, a difference that would not be seen using the Bispectral index (BIS) monitor.

Example 10: Brain Computer Interface

Figure 14:
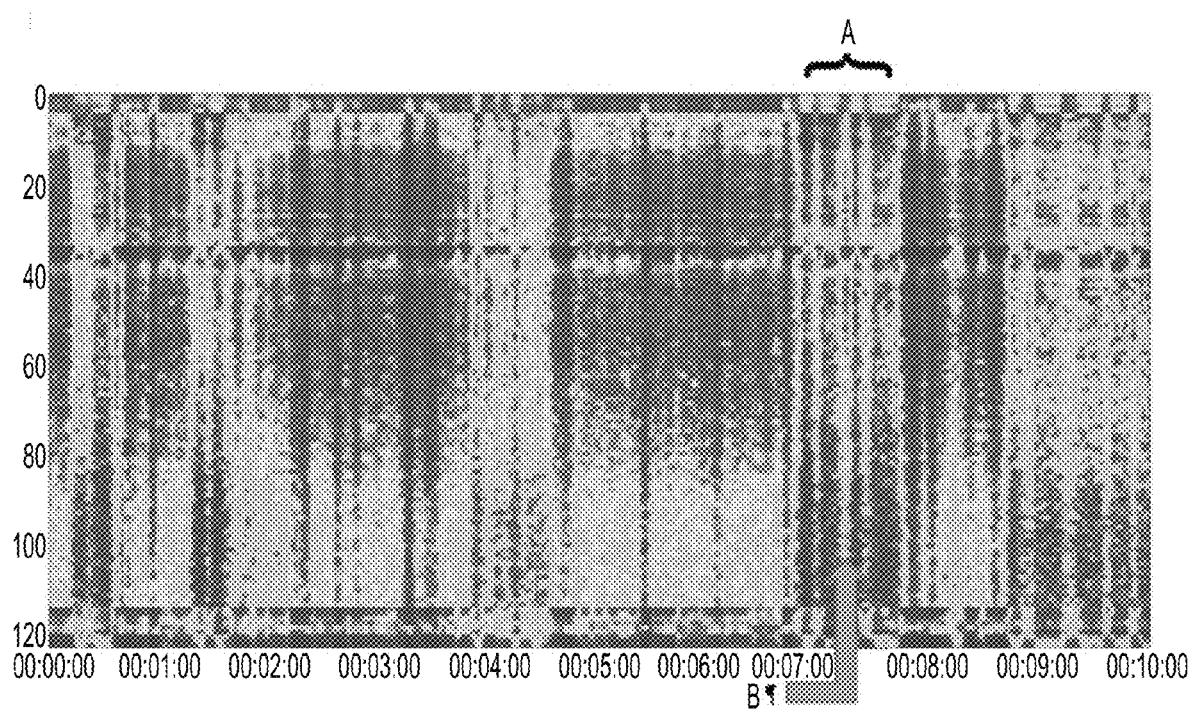
FIG. 14 shows a screenshot of an example of a BAFs representation of a subject according to some embodiments of the present invention.

FIG. 14 shows a BAFs representation from individual entering into a meditative state (as indicated by the horizontal bracket A), and leaves the meditated state. In the Example shown, the brain state in the time period indicated by the horizontal bracket A is associated with the meditative state. The system of the present invention analyzes the specific parameters of the BAFs within the BAFs representation, and applies a machine learning algorithm to detect a brain state associated with the meditative state. The system can then issue a specific command to the individual, once the brain state associated with the meditative state is detected. For example, the individual has ALS, and lacks motor control. The individual enters the meditative state, and the system issues a command for the individual to imagine shooting a ball into a hoop during the meditative state. All activity is performed with the eyes open, so as to make sure that the effects seen are not due to eye movement or being closed. All activity is also performed with background noise (family members speaking and watching the activity) so as to demonstrate the ability to disregard the environment and be fully concentrated in the activity.

Taken together, the data presented in Examples 1-10 show specific predictors for a specific brain state that were present in the BAF representations of human subjects. Further, the predictors for a specific brain state that were present in the BAF representations of human subjects were associated to brain states described in each of these embodiments. Automatic analysis of such BAF representations, to determine specific features related to brain activity which include but are not limited to abnormality, stress, and engagement can be done using state of the art techniques in machine learning and computer vision.

In some embodiments, the inventive specifically programmed computer processors and systems of the present invention can include the use of electronic mobile devices (e.g., smartphones, etc.) in the distributed network environment, communicating over a suitable data communication network (e.g., the Internet, etc.) and utilizing at least one suitable data communication protocol (e.g., IPX/SPX, X.25, AX.25, AppleTalk, TCP/IP (e.g., HTTP), etc.).

Figure 15:
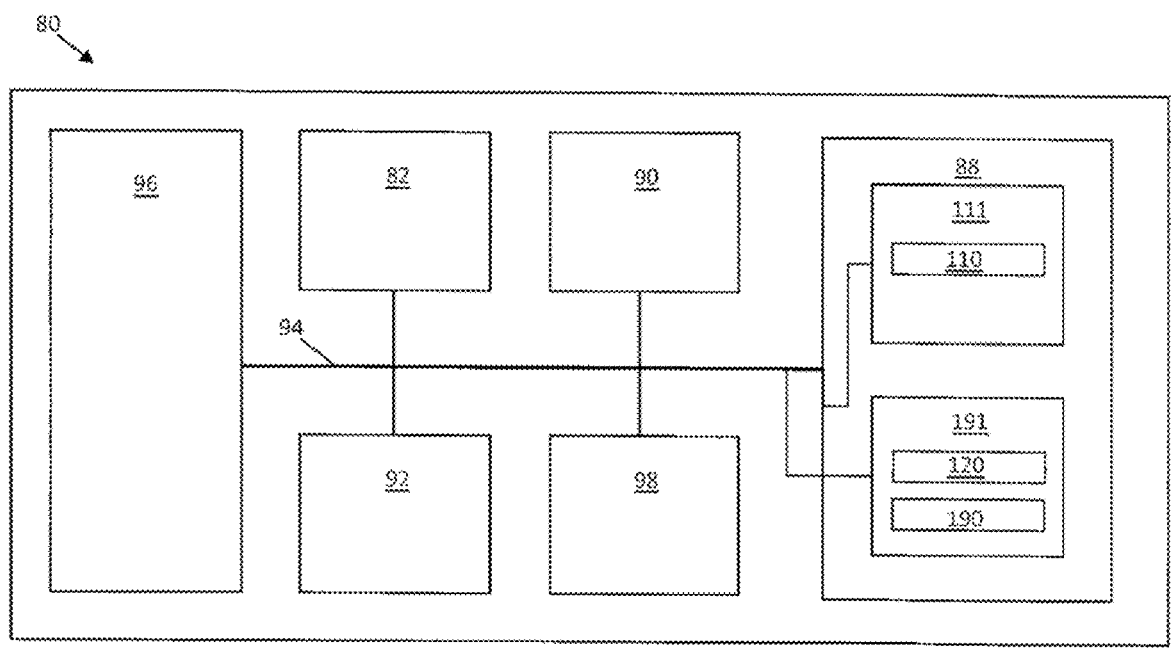
FIG. 15 shows a screenshot of an example of a computer architecture which is specifically programmed according to some embodiments of the present invention.

An exemplary block diagram of a computer system 80 which can be specifically programmed in accordance with the present invention is shown in FIG. 15. Computer system 80 includes a processor 82, such as a central processing unit, an input/output interface 90 and support circuitry 92. In certain embodiments, where the computer 80 requires a direct human interface, a display 96 and an input device 98 such as a keyboard, mouse or pointer are also provided. The display 96, input device 98, processor 82, and support circuitry 92 are shown connected to a bus 94 which also connects to a memory 88. Memory 88 includes program storage memory 111 and data storage memory 191. Note that while computer 80 is depicted with direct human interface components display 96 and input device 98, programming of modules and exportation of data can alternatively be accomplished over the interface 90, for instance, where the computer 80 is connected to a network and the programming and display operations occur on another associated computer, or via a detachable input device as is known with respect to interfacing programmable logic controllers.

Program storage memory 111 and data storage memory 191 can each comprise volatile (RAM) and non-volatile (ROM) memory units and can also comprise hard disk and backup storage capacity, and both program storage memory 111 and data storage memory 191 can be embodied in a single memory device or separated in plural memory devices. Program storage memory 111 stores software program modules and associated data, and in particular stores one or more modules 110. Data storage memory 191 stores the data sets representative of the signal data and various software objects utilized in accordance with the present invention.

It is to be appreciated that the computer system 80 can be any computer such as a personal computer, minicomputer, workstation, mainframe, a dedicated controller such as a programmable logic controller, or a combination thereof. While the computer system 80 is shown, for illustration purposes, as a single computer unit, the system can comprise a group/farm of computers which can be scaled depending on the processing load and database size. In certain embodiments, the system and method herein can be operate on a user's computer, for instance, in a user's browser, querying among schedule data that resides on the user's machine, after having been downloaded without query from a networked server computer. However, not all of these components may be required to practice the invention, and variations in the arrangement and type of the components may be made without departing from the spirit or scope of the invention. In some embodiments, the inventive system and method may include a large number of users and/or concurrent transactions. In other embodiments, the instant inventive systems are based on a scalable computer and network architecture that incorporates various strategies for assessing the data, caching, searching, and database connection pooling. An example of the scalable architecture is an architecture that is capable of operating multiple servers that are in real-time communicating with numerous electronic devices of users (e.g., smartphones). In some embodiment, the inventive systems of present invention can host a large number of electronic devices of users (e.g., at least 100; at least 1,000, at least 10,000; at least 100,000; at least 1,000, 000; at least 1,000,000,000, etc.) and/or perform a large number of concurrent actions/transactions (e.g., at least 1,000; at least 10,000; at least 100,000; at least 1,000,000, at least 1,000,000,000, etc.).

The computing device 80 preferably supports an operating system, for example stored in program storage memory 111 and executed by the processor 82 from volatile memory. According to an embodiment of the invention, the operating system contains instructions for executing software routines programmed in accordance with the present invention.

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

Figure 16:
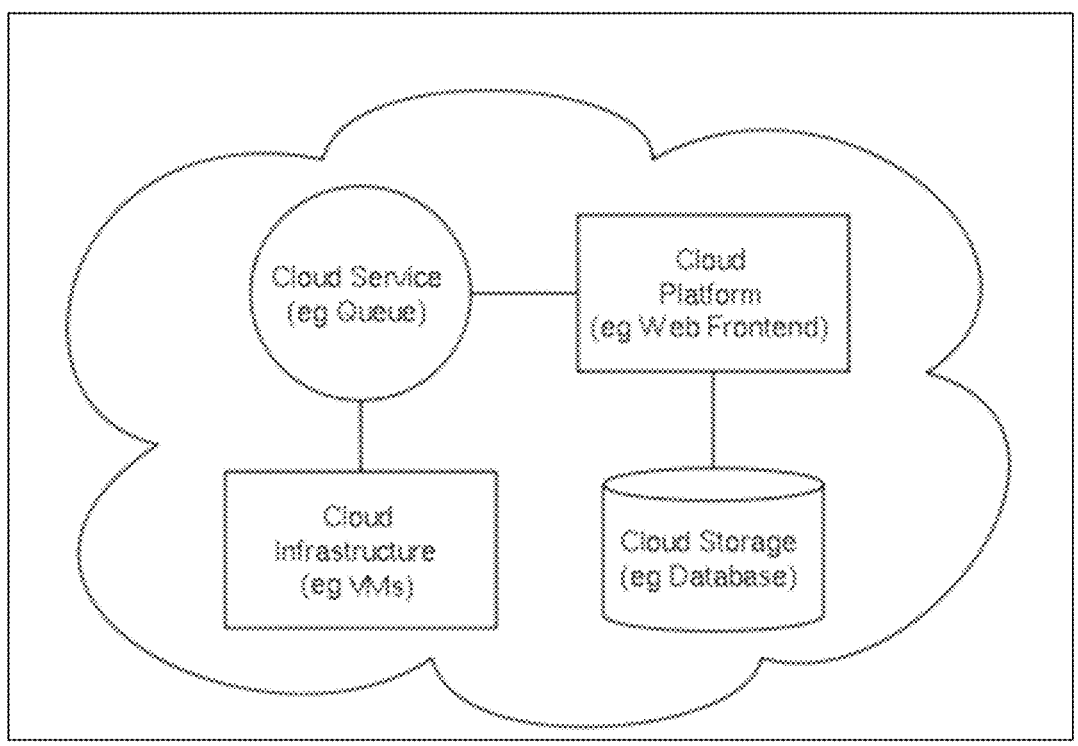
FIG. 16 shows a screenshot of an example of a computer architecture which is specifically programmed according to some embodiments of the present invention.
Figure 17:
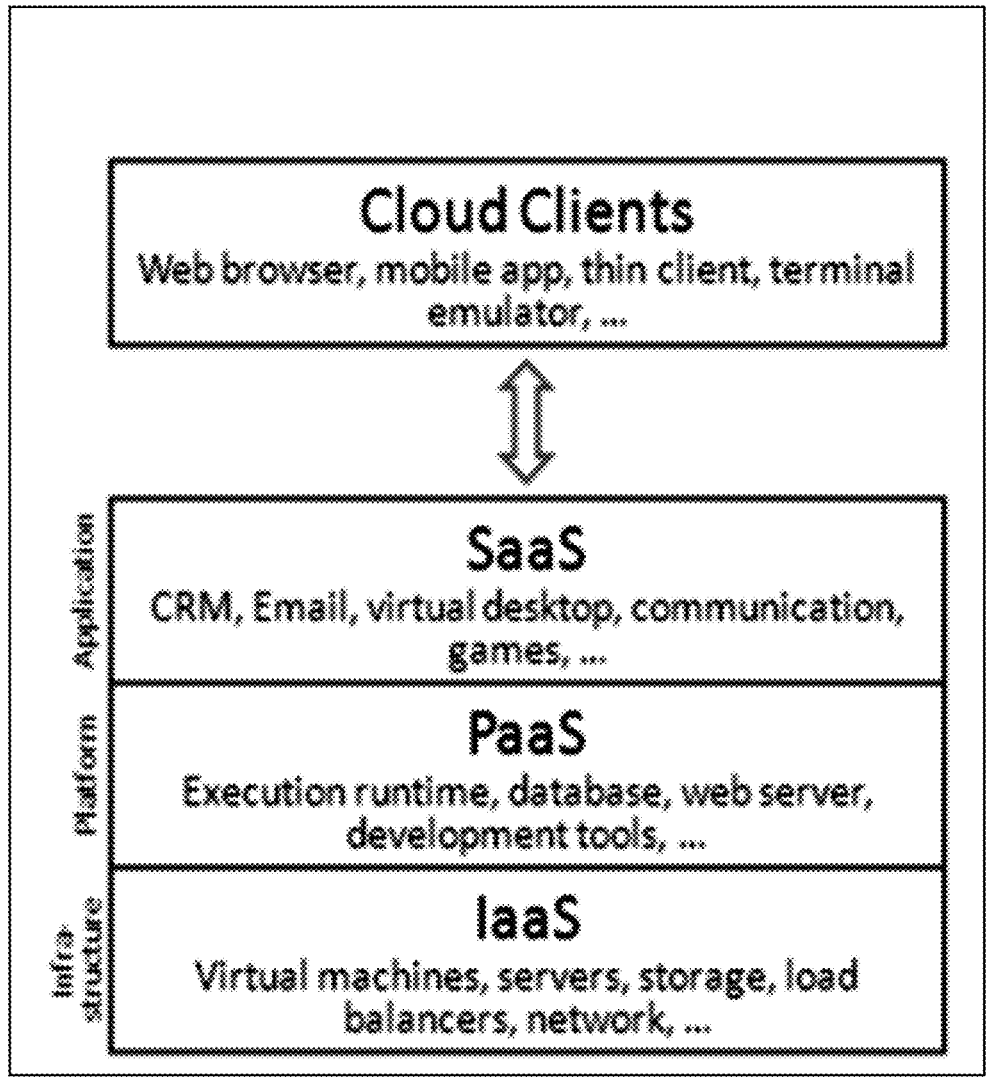
FIG. 17 shows a screenshot of an example of a computer architecture which is specifically programmed according to some embodiments of the present invention.

For purposes of the instant description, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the inventive game-operating system offers/manages the cloud computing/architecture as, but not limiting to: infrastructure a service (IaaS), platform as a service (PaaS), and software as a service (SaaS). FIGS. 16 and 17 illustrate schematics of exemplary implementations of the cloud computing/architecture. In some embodiments, the exemplary specifically programmed processor of the present invention is programmed as a cloud-based server which receives, over a computer network, a remotely acquired signal data to analyze such data in accordance with the principles of the present invention and to remotely communicate results of such analysis.

Example 11: Exemplary Stimuli for Infant Subjects at Various Developmental Stages Below are illustrative examples of applications that at least some embodiments of the present invention can be utilized to affect cognitive, linguistics, social and/or musical skills, such as, but not limited to:
1. Learning—attention span
    a. Age 1-6 months
        i. Inhibition dis-inhibition—a recording of different melodies, musical tones, white noise, or any other sound will be played by the system. At a specific time, the tones will be changed, and brain response will be tested using the methods according to some embodiments of the present invention. The system will test whether a different response is obtained when the sound changes and if the infant detects the change.
        ii. Reaction to unexpected sound—A recording of different loud or quiet sounds will be played by the system. At a specific time, the device will play the sounds, and brain response will be tested using the methods according to some embodiments of the present invention. The system will test whether a different response is obtained when the sound is played, if the infant detects it, and the character of his reaction (stress, attention or withdrawnness).
        iii. Minimal stimulation—A recording of adaptive musical sounds will be played by the system. Those sounds will begin as a minimalist sounds and gradually become richer. The brain response will be tested using the methods according to some embodiments of the present invention, and the complexity level of the music will be adapted to the infant's attention span.
        iv. Attention to talking faces—A visual representation or a recording of human talking faces and the correlated auditory sound of speech. The brain will be tasted while engaging with the talking faces using the methods according to some embodiments of the present invention. The duration and the levels of engagement and attention will be tasted. This can be applicable for ages 0-12 months.
    b. Age 7-12 months
        i. Anticipation test—A recording of known musical sounds or songs sang in human voice will be played by the system. At a specific time, an unexpected change in the known sound will occur. The brain response will be tested using the methods according to some embodiments of the present invention, and the attention level will be detected.
        ii. Turn-taking—the infant will be engaged in a game (peekaboo for example) that will be displayed by a toy/robot/phone/tablet. The game makes a move, and in order to continue playing the infant will be needed to engage in a specific brain states (increase his attention for example). The brain response will be tested using the methods according to some embodiments of the present invention, and the game will continue only when the child will be engaged (take his turn). This can be applicable for all ages—depend on the game's shape.
    c. Age 12-18 months
        i. Minimal vs complex stimulation—the infant will be engaged in a game that will be displayed by a toy/robot/phone/tablet and present multi-sensory experience that may include different colors sounds and shapes. Those experiences will begin as minimalist, and gradually become richer. The brain response will be tested using the methods according to some embodiments of the present invention, and the complexity level of the experience will be adapted to the infant's attention span.
        ii. Minimal vs complex stimulation—the infant will be engaged in a game that will be displayed by a toy/robot/phone/tablet and present multi-sensory experience that may include different colors sounds and shapes. In every round of the game, a very simple stimulus will appear, and the infant would have to engage with a specific brain state (need to expand his attention span) in order to trigger the game. The brain response will be tested using the methods according to some embodiments of the present invention, and when the infant succeed to engage in the chosen brains state the presented stimuli will become more complex.
    d. Age 18-24 monthes
        i. Inhibiting non related stimulation—The child will be engaged with an interesting game that will be displayed by a toy/robot/phone/tablet. Along with the game, non-related sounds and visuals will appear, and the child need to ignore them in order to continue playing. Distractions from the game will be detected using the methods according to some embodiments of the present invention and will operate a specific sounds played by the toy/robot/phone/tablet. This can also apply to 2-5 year old.
  e. Age2-5 years
    i. Keep interest in long activities—The child will be engaged with a game that contain a longitudinal task and displayed by a toy/robot/phone/tablet. Attention to the game will be detected using the methods according to some embodiments of the present invention. Distractions from the game will be detected, and operate a specific stimulus that contain auxiliary signs that direct the child back to the task and will be played by the toy/robot/phone/tablet.
2. Gaining Healthy Habits
  a. Age 1-6 months
    i. Gaining healthy sleeping habits—Using the methods according to some embodiments of the present invention, the system can monitor times when asleep, quality of sleep, sleep depth, duration to fall asleep and wake up. Utilizing those readouts and the hour of the day, the system can provide the infant with auditory feedback that encourage relaxation, and accelerate sleep. Also, during sleep, the music can be change individually to enable deeper and better relaxation.
    ii. Over Passivity/activity—Using the methods according to some embodiments of the present invention, the system can monitor lack of interest in surroundings, or excessive-activity, hyperactive patterns, and lack of focused attention. The system then provides self-adjusted sounds, vibrations or displayed pictures and lights that aim to attract focused attention and train and regulate their attention habits.
    iii. Stress and calming down—Using the methods according to some embodiments of the present invention, the system can monitor stress levels. It alerts when the baby feels uncomfortable or stressed and provides self-adjusted relaxing sounds, vibrations or displayed pictures and lights.
  b. Age 6-12
    i. Stress and calming down—Using the methods according to some embodiments of the present invention, the system can monitor stress and relaxation levels, and monitor self-quieting activities by the infants; how often and how quickly he quiet himself. The system assist him in the relaxation process by playing self-adjusted relaxing sounds, vibrations or displayed pictures and lights.
  c. Age 2-5 years
    i. Schedules, inhibiting non related stimulation—The child will be engaged with a Table daily assignments, and will be asked to put the assignments in the right order and in the right time of the day. His brain activity and his response to questions such "what should you do now" will be tested using the methods according to some embodiments of the present invention. The difficulty level will be adjust to the child's performances and gradually increase the difficulty level. In a different set, the daily schedule should be interrupted or altered and, the system will monitor child's tendency to stay focused and keep high performances.
3. Social skills—Attention to human gestures and Reaction toward social stimuli.
  a. Age 1-6 months
    i. Reaction toward infant's own name—A recording of the infant's name using the voice of the mother/father will be in the system, as well as infant's name produced by the AI device. At specific times, the device will call the child's name and test for brain response. The response will be tested using the methods according to some embodiments of the present invention. The system will test whether a different response is obtained when the child hears the name in the mother's voice and when it is heard in a stranger's voice. This can be applicable for all ages.
    ii. Infant's reactions toward human vs. non-human sounds—A recording of instrumental melodies and the same melodies sang or hummed by humans will be in played by the system. The system will test whether a different response is obtained, by listening to the same melody in the instrumental version vs. the human one, and if there is preferences to human voice by detecting excitement and attention levels using the methods according to some embodiments of the present invention.
    iii. Infant's reactions toward direct eye contact with people—A visual representation or a recording of human talking faces and the correlated auditory sound of speech. Using both the methods according to some embodiments of the present invention and eye tracker, the system will test whether the infant is paying a direct attention to the eye area of the face, to other part of the face, or not paying attention to the face at all. In case he doesn't paying attention, the recording will be adapted and try to attract his attention using facial expirations and sounds. This can be applicable for ages 0-12 months.
    iv. Reaction toward talk and laugh sounds—A recording of laugh and talking sounds using the voice of the mother/father will be in the system, as well as laugh and talking sounds that produced by the AI device. At specific times, the device will play those sounds and test for brain response. The response will be tested using the methods according to some embodiments of the present invention. The system will test whether a different response is obtained when the infant hears such social sounds.
  b. Age 7-12 months
    i. Initiating social interaction—A visual representation or a recording of human faces will be displayed by the system. Using the methods according to some embodiments of the present invention and a camera and a face recognition algorithm, the system will test whether the infant is trying to socially engage the presented face. An acts of social interaction can be detected by brain states that is specific to social interacrion combined with visual singes like smiling, cooing. If the infant try to socially engage, the system will present a social gesture (smile, wave, send kiss, talk . . . ). This can be applicable for all ages (e.g., 7 month-2 years). This can be applicable for older children—depending on the complexity of the feedback.

ii. Preference for caregiver voice—A recording of songs, lullabies, and short stories using the voice of the caregiver, as well as songs, lullabies, and short stories produced by the Artificial Intelligence (AI) device, will be in played by the system. At specific times, the device will switch the voice AI device and the caregiver, and test for brain response. The response will be tested using the methods according to some embodiments of the present invention. The system will test whether a different response is obtained when the child hears the caregiver voice and when he hears a stranger's voice. This can also be applicable for ages 7 months-2 years.

c. Age 12-24 months
  i. Understanding of gestures—The child will be engaged with a game that "Point on what it is labeling", using embedded auxiliary signs. For example, the game mark a specific face/shape and name it. Than the game will ask question ("dose the boy named Yossi?") and the brain activity will be tested using the methods according to some embodiments of the present invention. If the child can't understand the gesture, it will presented again more explicit. This can also be applicable for older children—depending on the stimuli and the questions difficulty.

4. Social skills—language development
  a. Age 1-6 months
    i. Sort out the phoneme that compose words—A recording of words and non-words will be in the system. The device will play those words one after the other and test for brain response using the methods according to some embodiments of the present invention. The system will test whether the infant can differentiate between the words and non-words and reword by playing happy sound if he does prefer the words. This can also be applicable for 0-12 month children.
    ii. Slow down the talker affect—A visual representation or a recording of human talking faces and the correlated auditory sound of speech, songs, lullabies, and short stories will be produced by the system. Using both eye tracker and the methods according to some embodiments of the present invention, the system will test whether the infant can track the story, and slow down the rhythm of the facial expressions and audio. This can also be applicable for 0-18 month children.
    iii. Learning of language prosody—Recorded stories with sentences that contain exaggerated intonations will be in the system. The device will play the stories and test for brain response using the methods according to some embodiments of the present invention. The system will detect whether the infant notice the exaggerated intonations, and test his emotional reaction. The system repeat the intonation in several variations as long as the infant keep response positively toward it. This can also be applicable for 0-24 month children.
  b. Age 6-12 months
    i. Learning of language prosody—A recording of sounds with different acoustic Intonations that differ in pitch, height, range/variability and melodic contour, will be in the system. The device will play those sounds one after the other and test for brain response using the methods according to some embodiments of the present invention. The system will test whether the infant can differentiate between the sounds and reword by playing happy sound if he does. The system continue playing sound combinations that can be more alike or differ one another—depends on the infants reaction. This can also be applicable for 6-24 months children.
  c. Age 12-24 months
    i. Learning of language prosody—Recorded stories with sentences that can be correct or incorrect in the intonations, will be in the system. The device will play the stories and test for brain response using the methods according to some embodiments of the present invention. The system will detect whether the infant notice unusual intonations. This can also be applicable for 0-24 month children.
    ii. Label words and their meaning—The infant will be engaged with a game that reads out words and sounds and present a visual representations of objects, shapes, colors, body parts and others. Each time two stimuli will be presented—word and visual. The stimuli can be related in meaning/category or not. Brain activity will be tested using the methods according to some embodiments of the present invention, and if the infant recognize two related stimuli correctly, the system can produce a happy rewarding sound. This can also be applicable for 6 months to 3 years children.
    iii. Understanding requests—The system produce simple questions and requests (e.g. "Come here" or "Want more?") via the loudspeakers on the toy/robot/phone/tablet. Those questions and request will be asked during and as part of larger game/activity (that is also produced by the system). Using the methods according to some embodiments of the present invention, and parameters such as attention, the system will determine whether the request is understood. (can fit to 2 years old using more complex requests with more words—"Roll the ball" "Kiss the baby" "Where's your shoe?" "Go bye-bye?" "What's that?")
  d. Age 2-5 years
    i. Understand complete sentences—The system produce sentences at varying difficulty in terms of grammar and vocabulary and test whether attention is preserved whether mood of the sentence is understood (happy sad, fearful). Production of the test is via the loudspeakers on the toy/robot/phone/tablet receiving information from the cloud (e.g., IBM's Watson like AI machine).
    ii. Reading skills—The system presents visual and auditory representations of letters and vowels, and then combine them in words in a correct or incorrect way. Using the methods according to some embodiments of the present invention, the system can test the cognitive response and attention, and decide if the child detected a mistake, reward him, and show him how to fix the mistake.
    iii. Second language—The system cam present visual and auditory representations of letters and vowels, words and sentences in different languages. Using the methods according to some embodiments of the present invention, the system can test the cognitive response and attention, and use variety of techniques to tech him the fundamentals of new languages.
    iv. Naming objects—The child will be engaged with a game that reads out words and sounds and be presented with visual representations of objects, shapes, colors, body parts and others. Each time a visual will be presented and the brain activity will be tested using the methods according to some embodiments of the present invention. If the infant familiar with the word, the system will reward him with a happy stimulus, if he doesn't, the system will read and teach him the new word.
5. Musical skills
  a. Age 1-6 months
    i. Introduction to quality musical literature—A recording of different melodies, and musical pieces will be played by the system at specific times. Those times will be determent by the brain response, using the methods according to some embodiments of the present invention. The system will test when the infant is focused and concentrate, and also his mood, and decide what type of music to play.
    ii. Notice music and its spatial origin—A recording of different musical tones or any other sound will be in system, and speakers will be located in different areas of the child play zone. At a specific time, the sound will be played, and brain response and the head turn will be tested. Brain response using the methods according to some embodiments of the present invention and head turn via accelerometer. The system will test whether a specific response is obtained when the sound played and if the infant detects it correctly in the space.
  b. Age 12-18 months
    i. Recognizing different musical patterns—a recording of different melodies and musical notes will be played by the system. The same musical melody will be played repeatedly, and will changed in a specific time to a similar but different melody/musical notes (for example increasing vs decreasing notes, couture changes, length of the notes and any other musical construction changes). Brain response will be tasted using the methods according to some embodiments of the present invention. The system will test when the infant is detected the change and reward him with happy stimulus.
    ii. Musical discrimination—The system produce sounds of differentiate musical instruments and timbers, play it in pairs that constructed due to their acoustic differences. The system analyzes the infant discrimination capability via the methods according to some embodiments of the present invention. If the infant was able to discriminate between the pair of stimuli, he gets a feedback in the shape of self-adjusted musical reword. The set of stimuli can differ more and more as the infant succeed to discriminate. (This can also be applicable for 12 months to 5 years children.
  c. Age 2-5 years
    i. Logical rules of music—The system produce music at different bitrates (for example, but not limited to, 80 bpm), preferably in a minimal music (simple with few instruments and vocals). At a specific time and for a small period the bitrate will be changed. Brain response to the change in rhythm will be tested using the methods according to some embodiments of the present invention, and will be rewarded by presentation of happy stimulus.
    ii. Logical rules of music—The system produce music at different time signatures (e.g., ¾). At a specific time and for a small period the amount of beats per bar will be changed. Brain response to the change in time signature will be tested using the methods according to some embodiments of the present invention, and will be rewarded by presentation of happy stimulus.
    iii. Logical rules of music—The system produce music at different scales (for example pentatonic scale) up and down a few times. At a specific time and for a small period the scale will be deviated from the correct note. Brain response to the incorrect scale will be tested using the methods according to some embodiments of the present invention, and will be rewarded by presentation of happy stimulus.
6. Learning and semantic memory development
  a. Ability to learn new categories; for example, the system produces rows of stimuli that relate in the same category, and attach to the row a single stimuli from an unrelated category (possible category types: musical stimuli from the same category, semantical stimuli from the same category, subject related categories such colors, animals, words and numbers, or any other type of category). The system analyze the infants reaction to the unrelated stimulus by measuring attention levels, reaction time and the number of times stimulus should be presented in order to facilitate learning of the category. The system will provide musical reword if the infant succeed to discriminate the unrelated stimulus. The category may become more and more complex as the infant show the ability discriminate simple once.
  b. Monitoring learning capacities; quality of engagement with complex stimuli as a function of its complexity. The system produces both simple and complex musical and visual stimuli, and analyzes the infant's changes in excitement and attention levels, the duration to engage with each stimulus, and the number of times each complex stimulus should be presented until it became trivial to the infant. The system will provide more and more complex stimuli, until the infant will no longer be attentive. Rows of stimuli can start with more complex once as the infant sharpen his discrimination skills.

Example 12: Exemplary Method According to Some Embodiments of the Present Invention In some embodiments, BAF representations are further analyzed to identify features that are repeatedly observed in a subject's visual representation of brain activity in response to an at least one stimulus. The method is as follows:

Let $B(j,t)$ be a matrix of BAF where the rows j go from 1 to 121 in case of 121 BAFs, and the columns t represent time with steps of one second, namely the BAF vectors is being updated every 1 sec. In some embodiments, the rows are more correlated as they are closer to one another, so the brain activity values in row j are more correlated to those in row j+1 than to those in row j+2, under some measure of correlation over a large data set that was used to determine the BAFs.

There is also a labeling L(t) which labels what happened during the recording of each time column. Thus, it is possible to build predictors to specific events that occurred during the time the BAF data was collected, and it is possible to cluster the columns of the matrix in a supervised (looking at the labels) or unsupervised way, like in k-means clustering. Furthermore, it is possible to cluster only part of the matrix namely only several of the BAFs. This enables to find those channels that produce a more coherent set of clusters from the data, namely they produce a set of cluster centers where the activity in a specific set of channels often falls into one of the cluster centers, namely the actual activity is not far (by some measure such as Euclidian distance) from the activity represented by the cluster center.

In some embodiments, the clusters are named, to indicate the BAF channels where they came from, and the actual cluster center that was found in those channel: for example, one feature, by way of illustration can be named 1320_15, to indicate that the cluster corresponds to channels 13 to 20 and it is ordinal cluster 15 that was found in that set of BAFs. This actual name can be considered a certain letter in a novel alphabet that can be found in brain activity after the interpretation into BAFs.

Given this alphabet, one can then look at letters which are highly correlated, namely clusters from different channels which co-occur at high probability. Then such letters can be combined into a single letter. This is done after building a covariance matrix of all letters found, and then based on then combining letters with a correlation above a preset threshold.

Once a minimal alphabet was found (after combining letters) one can look at words that are being formed, namely a collection of several letters that occur together. Also grammatical rules can be inferred using Markov modeling, namely inference of letters/words which occur in a sequence at high probability.

All said inference can now be used together with the labeling to determine a correlation of the inferenced brain response and he events that occurred while the BAFs were recorded. Once such correlation is found, we assume that there was a coherent brain response to the stimulus and can then record the stimuli which produced a coherent brain response.

Based on the coherent response, we can determine the degree of responses to the stimuli which we term RtS.

In one specific embodiment, RtS can help indicate the type of stimuli that a person that is in a Minimal Conscious State (MCS) responds to. For example, it can help determine whether the person responds in a consistent way to visual stimuli, auditory stimuli, other sensory stimuli, commands etc.

In some embodiments, RtS can indicate the degree of minimal consciousness the person is in, can help optimize medical intervention that aims to increase response to various stimuli. In the case of a person in MCS, in some embodiments, one can look at the entropy of the said alphabet and produce a single number which determines the total entropy of the alphabet (just based on letters or also based on more sophisticated grammatical rules that are inferred and length of words that are inferred.

In one specific embodiment, the said alphabet can be used to create music. This is to enable a MCS subject to produce some means of communication and to obtain neural feedback on its brain activity. Specifically, different letters can produce different musical notes with different musical instruments or can be used to change tempo and other musical parameters. The result would be a melody that is produced from an MCS or a baby's brain and can provide a means of communication. A MCS subject can learn to operate external devices once a control on the production of these letters is achieved. Using the musical feedback, subjects can train to produce the desired response. A reduced version of this, for example, to subjects who have difficulty hearing, or when in a place with a lot of noise, is a Bluetooth operated ball that can move in the XY direction and can also change its colors. These parameters can be tied to some of the BAF, or channels as described below in the caption of FIG. 19.

In a specific embodiment, the group of channels 34-38 which have been found to be missing in MCS can be used as a neural feedback to encourage MCS subjects to increase the activity of these channels.

In another embodiment, such entropy inference and the creation of alphabet can be done in a totally unlabeled (unsupervised) manner. This can be useful when determining the degree of brain damage, such as, for example, of a baby that was born during an ischemic episode, namely a baby that was born while the mother suffered a transient ischemic attack.

In one specific embodiment, a simpler statistical inference can be performed: as several channels were already found to correspond to some general brain activity, for example, there are channels that are associated with emotion brain activity and executive brain activity and are depicted in FIG. 19.

Example 13: Nocturnal Patient Monitoring

Nighttime can be a very dangerous period for elderly people. By way of illustration only, the danger can be attributed to several factors:

Cardiac—By way of illustration, individuals who suffer from cardiac malfunction such as congestive heart failure, need to sleep on an elevated pillow, so that their chest is higher than the legs. When that does not happen, or when they have forgotten to take their diuretic medication, there may be excessive amount of fluids in the body, and at night, the lungs can fill up with fluids very quickly, and lead to a life-threatening situation during few hours of sleep.

The poor heart activity together with fluids building in the lungs lead to reduced oxygenated blood flow. When the brain receives less oxygenated blood than needed, the processes which occur during sleep of removal of toxins from the brain as well as memory consolidation and other processes that we know little about may be affected, leading to the development of brain damage. In severe cases of flow reduction, small or large cerebrovascular accident (CVA, stroke) may occur. All these processes can be seen as abnormal brain activity in comparison to regular brain activity which occurs during nights when blood flow is normal.

Falling at night—Elderly tend to get up at night and go to the bathroom. At such times, they are at a higher risk of falling, due to darkness and potential confusion from waking up during a deep sleep stage.

Apnea and COPD—Elderly often suffer from some chronic obstruction of their lungs like COPD, and receive poor ventilation during sleep, leading to poor sleep.

Epileptic activity—At night, some epileptic activity or status epilepticus is more common, again leading to poor night sleep with bad consequences for the following day.

Changes in sleep patterns—When monitoring regularly brain activity during sleep, it is possible to detect changes in activity, which may be indicative of developing situations.

These include but are not limited to:

Trauma or the development of post traumatic syndrome PTSD

Minor or major stroke, development of dementia, Alzheimer or Parkinson.

Depression, or bipolar condition

Concussion and TBI

Swelling in the brain or tumor

Change in dream patterns due to stress, lack of nutrition and vitamins.

Thus, is it may be very beneficial to monitor elderly at sleep and be able to alert them and the caregiver, should adverse medical conditions develop. If we add to this the fact that the evening may be a difficult time period of the day due to loneliness and fatigue, it may be beneficial to start the monitoring at the evening before going to sleep. Furthermore, it is beneficial to monitor both the physiological components of blood flow and normal cardiac activity together with cognitive and emotional functioning to get a holistic view of the patient.

It is possible to combine brain activity monitoring with the measurement of physiological parameters. Using galvanic skin response (GSR) as an example, skin conductivity can provide full indication of unexplained sweat or temperature change which will then be correlated with brain activity and cardio/respiratory activity to obtain more accurate indication about stress (physiological or mental).

Monitoring Awake Individuals:

For monitoring of cognitive and emotional activity, the subject would wear the apparatus right after dinner, during the time of social activity or other recreational activity which may include: playing (computer) games, social interaction, watching TV or other multimedia, reading, playing a musical instrument and so forth.

During the time of such activity, the cognitive performance as well as emotional states are being recorded and interpreted. See, for example, U.S. patent application Ser. No. 15/045,089. Such measurements will be compared to similar measurements of the same individual, taken in previous days, weeks, months, while performing similar activity. That means that if Wednesday evening is a chess playing evening and Thursday is a TV watching evening, then comparison will be to the right similar activity. What is expected is changes from high concentration to low concentration and specifically, changes of individual cognitive parameters such as those associated with deduction, short and long term memory and comprehension. Such changes are normal, and the cycle of the changes can indicate normal or abnormal behavior. For example, if concentration levels remain very high for a long time, that can indicate stress, or a high dose of brain stimulant such as caffeine. If the levels of concentration remain constant at a very low level, that may indicate fatigue, sleepiness, lack of a regular medication and boredom.

Similar considerations hold with emotional parameters. Stress can have positive and negative aspects. When the level of stress goes up with attention and cognitive activity, this is natural and expected to address a high degree of cognitive load, e.g. in a demanding computer game. However, when the level of attention is high while cognitive activity is low, this is an indication of stress. Indication of happiness and lack thereof, which may indicate sadness should also fluctuate and not stay at one level. It is clear that if a subject is watching a movie, then, during sad parts of the movie, sadness will prevail and vice versa. What is of importance then, is the variability in mood, concentration, attention, load and stress.

Importantly, it is not essential to know exactly what the person is doing, or what movie the subject is watching, although knowing that would enable optimization of the multimedia and other stimuli to brain activation.

Monitoring Sleeping Individuals:

Sleep patterns are described in U.S. patent application Ser. No. 15/045,089. In particular, there were deep sleeping patterns which resembled brain activity during anesthesia of IV and the milder sleep pattern which resembled brain activity during anesthesia induced by gas. Other sleep patterns resembled meditation of various sorts. Thus, it is possible to establish an individual baseline sleeping pattern and then notice changes from the baseline which may provide alerts to caregivers or to the patient.

Fall Prevention:

As seniors tend to get up at night and go to the bathroom, it is important that they will get out of bad only if their brain is function well enough, as otherwise, they are more likely to fall. Thus, the sensor can provide a real-time alert when not to get out of bed based on real-time interpretation of brain activity. Furthermore, the apparatus may include a system to wake up the senior at times close to the times the senior usually goes to the bathroom, but when sleep is milder and thus it is easier to fully wake up.

Example 14: The Apparatus According to Some Embodiments of the Present Invention The brain is active at all times and is often performing many tasks at once. Failure of the brain to perform some of its tasks may put us in immediate danger, or may start a vicious circle of mental and cognitive deterioration. Such deterioration, if not detected early enough, may be more difficult to halt or even revert. This suggests that subjects with a high risk of brain malfunction or subjects which perform tasks where brain malfunction may create a big risk may benefit from brain activity monitoring that can detect the development of irregular brain activity as early as possible.

In a similar manner, patients with hemodynamic problems such as those with cardiac problems, blood pressure issues, respiratory or sleep disorders, or frail patients in general, can all benefit from the vital signs monitor.

Continuous brain status monitoring may be required for one or more of the following reasons.

Chronic Disease Management:

This can include epilepsy, depression, Alzheimer's, Parkinson, OCD, PTSD, ADD and mental illness. In each of these cases, it is important to detect real-time changes which require intervention. The intervention can be in the form of (deep) brain stimulation, release of medication, neural feedback, social activity, physical therapy and more.

Brain Injury Such as Hemorrhage, Concussion or Stroke:

In this case, the patient is hospitalized with some form of injury which reduces cognitive functioning and alertness, possibly to the level of being unconscious. It is then important to be able to quickly respond to physiological changes such as hemorrhage and to be able to monitor the consciousness level, the sleeping patterns and the level of cognitive alertness, to better assess the brain injury, the response to mental stimulation and medications.

Brain Stimulation:

Brain stimulation (BS) is a relatively new form of remedy and its full consequences are still under investigation. In particular, it is important to assess the effect of BS on cognitive functioning, mood swings and sleep quality in addition to the specific brain malfunction it is provided for.

Neural Feedback:

Neural feedback requires continuous monitoring to quantify the effect of the feedback immediately following the neural training, but also to quantify the aftereffect, which may alter cognitive functioning, sleep patterns and mood.

Elderly at Home:

Elderly people living by themselves, especially those who lost their longtime partner, are at high risk for dementia. The reduction in cognitive stimulation together with post-trauma depression, and the negative effect on healthy food and lifestyle habits, may cause quick physical, cognitive and mental deterioration, leading to frailty within a short time of weeks to few months. Keeping these elderly living independently in their homes for as long as possible is desirable for two main reasons: i) it is the natural environment for the elderly person, where she feels safe and comfortable and ii) the cost of any alternative care is far higher. It is therefore important to monitor such patients so as to intervene when necessary to avoid deterioration. Monitoring can include, for example:

Monitoring security and special units' personnel for stress and well-being during critical actions.

General brain machine interface for operation of games and other machines, utilizing their vital signs as additional information.

Monitoring preferences and desires of subjects such as for the purpose of advertisement analysis or purchase desires.

The brain activity monitor will then connect to the sensory environment monitor, which includes auditory and visual sensory input that is concurrently available to the subject, together with other sensory inputs which include but are not limited to temperature, pressure and humidity. Part of the sensory environment monitor may be a device such as Google Glass, which includes a camera and microphone and an object recognition as well as speech recognition tools to create a labeled sensory environment.

The connection is aimed at creating an input output relationship between the concurrent sensory input and resulting brain activity. Once a set of relationship has been formed, using a single subject or multiple subjects, brain monitoring can be performed by monitoring the relationship between the sensory input and the related brain activity. The monitoring examines the level of difference between the expected or previously modeled relationship and the observed relationship.

A common problem with EEG sensing is the high sensitivity to background noise of the system, especially at 50 or 60 Hz. This may cause saturation of the initial amplifiers and thus limits the amplification of the system. It also requires the use of notch filters to remove the noise which increase electronic components, computation power and removes part of the contents of the signal as part of the notch.

In particular embodiments, the present inventors are looking at the difference between the two frontal electrodes Fp1 and Fp2. Given that the focus is only directed to this difference in this embodiment, it is possible to create a symmetrical design where the electronics are located in the middle between the two electrodes and are receiving the signal in a symmetric way so that the surrounding noise which is common to both inputs is fully cancelled.

Figure 22:
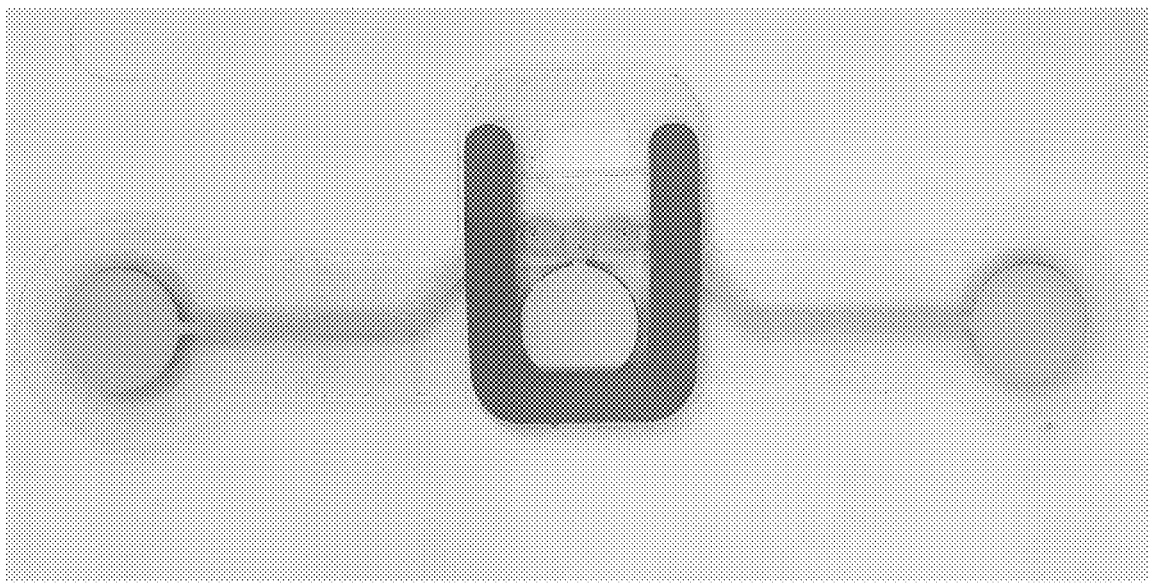
FIG. 22 shows an embodiment of an exemplary sensor as described herein.

FIG. 22 illustrates the aforementioned embodiment, wherein the three connections at the center provide a symmetrical input of the two electrodes and a reference electrode at the center.

Anesthesia and EMG and/or EOG

The signal which is sensed at the electrodes which reside on the forehead, contains three types of biomedical signals: a. EMG which is the muscle activity and is a strong signal with respect to the EEG; b. EOG which is the eye movement activity. This signal is an indication of eye movement. It appears that the sensitive electronics described herein produce a clear eye movement signal, thus facilitate a further examination of human subject's response and another means for a brain computer interface; and c. EEG which is the weakest signal and the only one related to brain activity.

When measuring the level of anesthesia or unconsciousness, one is only interested in the level of brain activity. In such a case, the muscle activity may produce noise which contaminates the EEG signal. Fortunately, there is a difference in the statistical properties between EMG and EEG which enables the present harmonic-analysis-based system to differentiate between these signals. This is in contrast to more conventional methods that call for analyzing the signal, for example the Bi spectral index or BIS, which is the common method for measuring anesthesia levels. The outcome is that the present method is less sensitive to muscle activity and in this way, measures the level of unconsciousness more accurately.

Lie Detection and Stress

Example 6 describes methods for stress detection and provides indicators as to how stress can be determined automatically from the processed data. In that stress may be associated with lie detection when a person is being interrogated, all of the guidance presented in Example 6 may be implemented with respect to stress induced during the course of an interrogation session wherein elevated stress levels may be used as a positive indicator of lying on the part of the subject being interrogated.

In some embodiments, the present invention provides an exemplary inventive system that includes at least the following components: an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; a specifically programmed computer system; where the specifically programmed computer system includes: i) a non-transient memory, electronically storing particular computer executable program code; and ii) at least one computer processor which, when executing the particular program code, becomes a specifically programmed computer processor configured to perform at least the following operations: continuously obtaining a recording of electrical signal data representative of the individual's brain electrical activity; continuously projecting, in real time, the obtained recording of electrical signal data onto a pre-determined ordering of a denoised optimal set wavelet packet atoms, to obtain a particular set of projections of the individual; continuously normalizing, in real time, the particular set of projections of the individual using a pre-determined set of normalization factors to form a set of normalized projections of the individual; continuously determining, in real time, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition; continuously determining a relationship between: i) the at least one physiological parameter, ii) the at least one environmental parameter, and iii) the at least one personalized mental state; continuously generating, in real time, an output, including: 1) a visual indication, where the visual indication is representative of the at least one personalized mental state, and 2) a feedback output which is configured to affect, based on the relationship, the at least one personalized mental state of the individual.

In some embodiments, the feedback output is selected from the group consisting of: an audible signal, a visual signal, a physically-sensed signal, and any combination thereof.

In some embodiments, the physically-sensed signal is a vibration that is physically sensed by the individual.

In some embodiments, the generating of the feedback output includes: determining a change beyond a pre-determined threshold in at least one of: i) the at least one physiological parameter, ii) the at least one environmental parameter, and iii) the at least one personalized mental state.

In some embodiments, the specifically programmed computer processor is further configured to determine the pre-determined ordering of the denoised optimal set wavelet packet atoms based on: obtaining from a plurality of individuals at least 100 recordings of electrical signal data representative of brain activity; obtaining an optimal set of wavelet packet atoms from the recorded electrical signal data from the recordings from the plurality of individuals, by: 1) selecting a mother wavelet selected from the group consisting of: Haar, Coiflet Daubehies, and Meyer wavelet families; 2) determining, by the specifically programmed processor, an optimal set of wavelet packet atoms, by: a) causing the at least one plurality of electrical signal data to be deconstructed into a plurality of wavelet packet atoms, using the selected mother wavelet; b) storing the plurality of wavelet packet atoms in at least one first computer data object; c) determining the optimal set of wavelet packet atoms using the pre-determined mother wavelet, and storing the optimal set of wavelet packet atoms in at least one second computer data object, where the determining is via utilizing a Coifman-Wickerhauser Best Basis algorithm; i) denoising the obtained optimal set of wavelet packet atoms from the recordings from the plurality of individuals; ii) reordering, the denoised optimal set of wavelet packet atoms from the recorded electrical signal data from the recordings from the plurality of individuals, to obtain a pre-determined ordering of the denoised optimal set of wavelet packet atoms from the recordings from the plurality of the individuals, by determining a minimum path, by: 1) projecting the at least one plurality of electrical signal data on to the denoised optimal set of wavelet packet atoms, to obtain a set of projections, where a projection is a result of a convolution of an electrical signal in each time window of the signal and a wavelet packet atom; 2) determining a collection of wire lengths for every data point within the set of projections, where each wire length is determined by a correlation of every two projections; 3) storing the collection of wire lengths for the set of projections in at least one third computer data object; 4) iteratively, determining, by the specifically programmed processor, a plurality of (i) orders of projections, and (ii) respective wire lengths, by i) determining the wire length for every data point in the projection by determining either the mean or sum of absolute distance of the statistical measure of the projections of different channels from their adjacent channels; and ii) storing the wire length data in at least one fourth computer data object; 5) determining, from the plurality of respective wire lengths, a particular order of projections that minimizes either the mean or sum of the wire lengths across the projections, across each 4 second window, and across all individuals within the plurality of individuals so as to identify the pre-determined ordered denoised optimal set of wavelet packet atoms; and creating the set of pre-determined normalization factors, and storing the pre-determined normalization factors in at least one fifth computer data object.

In some embodiments, the visual indication includes a visual map, generated by: calculating a standard deviation of a time window of each normalized projection of the particular set of normalized projections of the particular individual, and assigning a color to each normalized projection of the particular set of normalized projections of the particular individual, based on the standard deviation of the time window of the respective projection.

In some embodiments, the correlation of every two projections is selected from the group consisting of: the mean of the sum of the absolute differences of the wavelet packet atoms, and a mean of the sum of (1−correlation) of the wavelet packet atoms.

In some embodiments, the apparatus includes two electrodes configured to record the electrical signal data representative of the individual's brain activity.

In some embodiments, when the individual is a child between years of 0 and 12; the at least one personalized mental state is representative of a response of the child to at least one first musical stimulus; and the feedback output is at least one second musical stimulus.

In some embodiments, when the individual is a minimally conscious subject; the at least one personalized mental state is representative of a response of the minimally conscious subject to at least one stimulus; and the feedback output is at least one second stimulus configured to affect the minimally conscious subject.

In some embodiments, the least one environmental parameter is selected from the group consisting of: temperature, humidity, pressure, allergen level, and any combination thereof.

In some embodiments, the at least one machine learning algorithm is one of: logistic regression modeling algorithm, support vector machine modeling algorithm, and a deep learning modeling algorithm.

In some embodiments, the specifically programmed computer processor is further configured to perform at least the following operations: a) determining a first personalized mental state of the individual; b) generating a first visual indication, where the first visual indication is representative of the first personalized mental state; c) generating a first feedback output which is configured to affect, based on a first relationship, the first personalized mental state of the individual; where the first relationship is determined based on: i) at least one first physiological parameter, ii) at least one first environmental parameter, and iii) a first personalized mental state; d) determining, after subjecting the individual to the first feedback output, a second personalized mental state of the individual; e) generating a second visual indication, where the second visual indication is representative of the second personalized mental state; f) comparing the first visual indication and the second visual indication; g) generating a second feedback output which is configured to affect, based on a second relationship and a result of the comparing step, the second personalized mental state of the individual; where the second relationship is determined based on: i) at least one second physiological parameter, ii) at least one second environmental parameter, and iii) a second personalized mental state; repeating the steps a-g until at least one of: 1) a desired personalized mental state is obtained, 2) a first coherent response to the first feedback output is obtained, 3) a second coherent response to the second feedback output is obtained; and 4) any combination thereof.

In some embodiments, the first feedback output is at least one first reward.

In some embodiments, the second feedback output is at least one second reward.

In some embodiments, the present invention provides an exemplary inventive method that includes at least the following steps of: continuously obtaining, by a specifically programmed computer processor, a recording of electrical signal data representative of an individual's brain electrical activity; where the recording the electrical signal data representative of individual's brain electrical activity is received from an apparatus configured to be worn on an individual's head, and record: i) the individual's brain electrical activity, ii) at least one physiological parameter of the individual, selected from the group consisting of: heart rate, blood oxygen levels, body temperature, respiration rate, skin temperature, skin conductivity, and movement, and iii) at least one environmental parameter; continuously projecting, in real time, by the specifically programmed computer processor, the obtained recording of electrical signal data onto a pre-determined ordering of a denoised optimal set wavelet packet atoms, to obtain a particular set of projections of the individual; continuously normalizing, in real time, by the specifically programmed computer processor, the particular set of projections of the individual using a pre-determined set of normalization factors to form a set of normalized projections of the individual; continuously determining, in real time, by the specifically programmed computer processor, at least one personalized mental state of the individual by assigning at least one specific brain state to the individual based on applying at least one machine learning algorithm to the set of normalized projections of the individual, where the at least one specific brain state is associated with a mental state, a neurological condition, or a combination of the mental state and the neurological condition;

continuously determining, by the specifically programmed computer processor, a relationship between: i) the at least one physiological parameter, ii) the at least one environmental parameter, and iii) the at least one personalized mental state; continuously generating, in real time, by the specifically programmed computer processor, an output, including: 1) a visual indication, where the visual indication is representative of the at least one personalized mental state, and 2) a feedback output which is configured to affect, based on the relationship, the at least one personalized mental state of the individual.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A system, comprising:
   an apparatus configured to be worn on an individual's head, and record the individual's brain electrical activity, at least one physiological parameter of the individual, and at least one environmental parameter;
   a processor configured to:
      obtain a recording of electrical signal data representative of the individual's brain electrical activity;
      project, in real time, the obtained recording of electrical signal data onto an optimal set of wavelet packet atoms, to obtain a particular set of projections of the individual, wherein the optimal set of wavelet packet atoms is determined based on electrical signal data that is representative of general brain activity of a plurality of individuals;
      determine, in real time, at least one mental state of the individual by assigning at least one specific brain state to the individual based on applying at least one machine learning algorithm to the particular set of projections of the individual, wherein the at least one specific brain state is associated with a mental state, a neurological condition, or a combination of a mental state and a neurological condition;
      determine a relationship between:
         the at least one physiological parameter,
         the at least one environmental parameter, and
         the at least one specific brain state; and
      generate, in real time, an output
         representative of the at least one specific brain state of the individual,
         or expected to affect, based on the relationship, the at least one specific brain state of the individual.

2. The system of claim 1, wherein the output is selected from the group consisting of: an audible signal, a visual signal, a physically-sensed signal, and any combination thereof.

3. The system of claim 2, wherein the physically-sensed signal is a vibration that is physically sensed by the individual.

4. The system of claim 1, wherein the generating of the output comprises:
   determining a change beyond a pre-determined threshold in at least one of:
      the at least one physiological parameter, and
      the at least one environmental parameter.

5. The system of claim 1, wherein the apparatus comprises two electrodes configured to record the electrical signal data representative of the individual's brain activity.

6. The system of claim 1,
   wherein the individual is a child between years of 0 and 12;
   wherein the at least one specific brain state is representative of a response of the child to at least one first musical stimulus; and
   wherein the output is at least one second musical stimulus.

7. The system of claim 1,
   wherein the individual is a minimally conscious subject;
   wherein the at least one specific brain state is representative of a response of the minimally conscious subject to at least one stimulus; and
   wherein the output is at least one second stimulus expected to affect the minimally conscious subject.

8. The system of claim 1, wherein the at least one environmental parameter is selected from the group consisting of: temperature, humidity, pressure, allergen level, and any combination thereof.

9. The system of claim 1, wherein the at least one machine learning algorithm is one of: a logistic regression modeling algorithm, a support vector machine modeling algorithm, and a deep learning modeling algorithm.

10. The system of claim 1, wherein the processor is further configured to:
  a) determine a first mental state of the individual;
  b) generate a first visual indication, wherein the first visual indication is representative of the first mental state;
  c) generate a first feedback output expected to affect, based on a first relationship, the first mental state of the individual;
    wherein the first relationship is determined based on:
      at least one first physiological parameter,
      at least one first environmental parameter, and
      the first mental state;
  d) determine, after subjecting the individual to the first feedback output, a second mental state of the individual;
  e) generate a second visual indication, wherein the second visual indication is representative of the second mental state;
  f) compare the first visual indication and the second visual indication;
  g) generate a second feedback output expected to affect, based on a second relationship and a result of comparing the first visual indication and the second visual indication, the second mental state of the individual;
    wherein the second relationship is determined based on:
      at least one second physiological parameter,
      at least one second environmental parameter, and
      the second mental state;
  repeating the steps a-g until at least one of:
    1) a desired mental state is obtained,
    2) a first coherent response to the first feedback output is obtained,
    3) a second coherent response to the second feedback output is obtained; and
    4) any combination thereof.

11. The system of claim 10, wherein the first feedback output is at least one first reward.

12. The system of claim 10, wherein the second feedback output is at least one second reward.

13. The system of claim 1, wherein the at least one physiological parameter of the individual is selected from the group consisting of: heart rate, blood oxygen levels, body temperature, respiration rate, skin temperature, skin conductivity, and movement.

14. A method, comprising a processor configured to:
  receive electrical signal data representative of an individual's brain electrical activity;
  receive at least one physiological parameter of the individual;
  receive at least one environmental parameter;
  project, in real time, the received electrical signal data onto an optimal set of wavelet packet atoms, to obtain a particular set of projections of the individual, wherein the optimal set of wavelet packet atoms is determined based on electrical signal data that is representative of general brain activity of a plurality of individuals;
  determine, in real time, at least one mental state of the individual by assigning at least one specific brain state to the individual based on applying at least one machine learning algorithm to the particular set of projections of the individual, wherein the at least one specific brain state is associated with a mental state, a neurological condition, or a combination of a mental state and a neurological condition;
  determine a relationship between:
    the at least one physiological parameter,
    the at least one environmental parameter, and
    the at least one specific brain state; and
  generate, in real time, an output comprising:
    a visual indication representative of the at least one specific brain state of the individual, and
    a feedback output expected to affect, based on the relationship, the at least one specific brain state of the individual.

15. The method of claim 14, wherein the feedback output is selected from the group consisting of: an audible signal, a visual signal, a physically-sensed signal, and any combination thereof.

16. The method of claim 15, wherein the physically-sensed signal is a vibration that is physically sensed by the individual.

17. The method of claim 14, wherein the generating of the feedback output comprises:
  determining a change beyond a pre-determined threshold in at least one of:
    the at least one physiological parameter, and
    the at least one environmental parameter.

18. The method of claim 14, wherein the visual indication comprises a visual map.

19. The method of claim 14, wherein receiving electrical signal data representative of the individual's brain electrical activity comprises receiving the electrical signal data representative of the individual's brain electrical activity with an apparatus comprising two electrodes configured to record the electrical signal data representative of the individual's brain activity.

20. The method of claim 14,
  wherein the individual is a child between years of 0 and 12;
  wherein the at least one specific brain state is representative of a response of the child to at least one first musical stimulus; and
  wherein the feedback output is at least one second musical stimulus.

21. The method of claim 14,
  wherein the individual is a minimally conscious subject;
  wherein the at least one specific brain state is representative of a response of the minimally conscious subject to at least one stimulus; and
  wherein the feedback output is at least one second stimulus expected to affect the minimally conscious subject.

22. The method of claim 14, wherein the at least one environmental parameter is selected from the group consisting of: temperature, humidity, pressure, allergen level, and any combination thereof.

23. The method of claim 14, wherein the at least one machine learning algorithm is one of: a logistic regression modeling algorithm, a support vector machine modeling algorithm, and a deep learning modeling algorithm.

24. The method of claim 14, further comprising:
  a) determining a first mental state of the individual;
  b) generating a first visual indication representative of the first mental state;

c) generating a first feedback output expected to affect, based on a first relationship, the first mental state of the individual;
   wherein the first relationship is determined based on:
      at least one first physiological parameter,
      at least one first environmental parameter, and
      the first mental state;
d) determining, after subjecting the individual to the first feedback output, a second mental state of the individual;
e) generating a second visual indication representative of the second mental state;
f) comparing the first visual indication and the second visual indication;
g) generating a second feedback output expected to affect, based on a second relationship and a result of the comparing step, the second mental state of the individual;
wherein the second relationship is determined based on:
   at least one second physiological parameter,
   at least one second environmental parameter, and
   the second mental state;
repeating the steps a-g until at least one of:
   a desired mental state is obtained,
   a first coherent response to the first feedback output is obtained,
   a second coherent response to the second feedback output is obtained; and
   any combination thereof.

25. The method of claim 24, wherein the first feedback output is at least one first reward.

26. The method of claim 24, wherein the second feedback output is at least one second reward.

27. The method of claim 14, wherein the at least one physiological parameter of the individual is selected from the group consisting of: heart rate, blood oxygen levels, body temperature, respiration rate, skin temperature, skin conductivity, and movement.

* * * * *